United States Patent [19]

Russell et al.

[11] Patent Number: 6,077,948

[45] Date of Patent: *Jun. 20, 2000

[54] MEDIATORS OF CHRONIC ALLOGRAFT REJECTION (AIF-1) AND DNA ENCODING THEM

[75] Inventors: Mary E. Russell, Carlisle, Mass.; Ulrike Utans, Grenzach-Wyhlen, Germany

[73] Assignee: President and Fellows of Harvard College, Cambridge, Mass.

[ * ] Notice: This patent is subject to a terminal disclaimer.

[21] Appl. No.: 08/361,441

[22] Filed: Dec. 21, 1994

Related U.S. Application Data

[63] Continuation-in-part of application No. 08/171,385, Dec. 21, 1993, Pat. No. 5,527,884.

[51] Int. Cl.$^7$ .......................... C12N 15/12; C07K 14/435
[52] U.S. Cl. ........................ 536/23.5; 435/69.1; 530/350; 536/24.3
[58] Field of Search ................................ 536/23.5, 24.3; 530/350; 435/69.1

[56] References Cited

U.S. PATENT DOCUMENTS 5,527,884   6/1996   Russell et al. ........................... 530/350

FOREIGN PATENT DOCUMENTS

WO 90/04180   4/1990   WIPO .
WO 95/17425   6/1995   WIPO .

OTHER PUBLICATIONS

Shinjo et al., "Molecular Cloning of the Gene for the Human Placental GTP–Binding Protein G$_p$ (G25K): Identification of this GTP–Binding Protein as the Human Homolog of the Yeast Cell–Division–Cycle Protein CDC 42", *Proc. Natl. Acad. Sci. USA*, 87:9853–9857, Dec., 1990.

Papp et al., "Evidence for Functional Heterogeneity of Rat CD4$^+$ T Cells In Vivo: Differential Expression of IL–2 and IL–4 mRNA in Recipients of Cardiac Allografts", 1992, *J. Immunology*, 148:1308–14.

Utans, et al., "Chronic Cardiac Rejection: Identification of Five Upregulated Genes in Transplanted Hearts by Differential mRNA Display", 1994, *Proc. Natl. Acad. Sci. USA*, 91:6463–67.

International Search Report, PCT/US94/14724, filed Dec. 21, 1994.

Koller, M., et al., "Functional Analysis of the Promoters of the Human CaMIII Calmodulin Gene and of the Intronless Gene Coding for a Calmodulin–like Protein", 1993, *Biochimica et Biophysica Acta.*, 1163:1–9.

Lerman, A., et al., "Plasma Endothelin Concentrations in Humans With End–Stage Heart Failure and After Heart Transplantation", 1992, *J. Amer. College of Cardiology*, 1992, 20:849–53.

Lin, H., et al., "Comparable Proximal and Distal Severity of Intimal Thickening and Size of Epicardial Coronary Arteries in Transplant Arteriopathy of Human Cardiac Allografts", 1994, *J. Heart and Lung Trans.*, 13:824–33.

Parmacek, M., et al., "The Structure and Regulation of Expression of the Murine Fast Skeletal Troponin C Gene", 1990, *J. Biologic. Chem.*, 265:15970–76.

Russell, M., et al., "Structural Integrity of the Glycoprotein IIb and IIIa Genes in Glanzmann Thrombasthenia Patients from Israel", 1988, *Blood*, 72:1833–36.

Russell, M., et al., "Identification and Upregulation of Galactose/N–acetylgalactosamine Macrophage Lectin in Rat Cardiac Allografts with Arteriosclerosis", 1994, *J. Clin. Invest.*, 94:722–30.

Sayegh, M.H., et al., "Blocking the CD28–B7 Costimulatory T Cell Activation Pathway with CTLA41g Prevents Chronic Rejection in the LEW to F344 Vascularized Rat Cardiac Allograft Model", 1994, *J. Amer. Society Nephrology*, 5(3):989, Abstract 41P.

Strynadka, N., et al., "Crystal Structures of the Helix–Loop–Helix Calcium–Binding Proteins", 1989, *Annu. Rev. Biochem.*, 58:951–98.

Sharples, L.D., et al., "Risk Factor Analysis for the Major Hazards Following Heart Transplantation–Rejection, Infection, and Coronary Occlusive Disease", 1991, *Transplantation*, vol. 52, No. 2, pp. 244–252.

Cramer, D.V., et al., "Lymphocytic Subsets and Histopathologic Changes Associated with the Development of Heart Transplant Arteriosclerosis", 1992, *J. Heart Lung Transplant.*, vol. 11, No. 3, pp. 458–466.

Adams, D.H., et al., "Experimental Graft Arteriosclerosis", 1992, *Transplantation*, vol. 53, No. 5, pp. 1115–1119.

Adams, D.H., et al., "Experimental Graft Arteriosclerosis", 1993, *Transplantation*, vol. 56, No. 4, pp. 794–799.

Russell, M.E., et al., "Early and Persistent Induction of Monocyte Chemoattractant Protein 1 in Rat Cardiac Allografts", 1993, *Proc. Natl. Acad. Sci. USA*, vol. 90, pp. 6086–6090.

Liang, P., et al., "Differential Display of Eukaryotic Messenger RNA by Means of the Polymerase Chain Reaction", 1992, *Science*, vol. 257, pp. 967–971.

Steinbeck, M.J., et al., "Extracellular Production of Singlet Oxygen by Stimulated Macrophages Quantified Using 9, 10–Diphenylanthracene and Perylene in a Polystryrene Film", 1993, *J. Biologic. Chem.*, vol. 268, No. 21, pp. 15649–15654.

Arceci, R., et al., "Mouse GATA–4: a Retinoic Acid–Inducible GATA–Binding Transcription Factor Expressed in Endodermally Derived Tissues and Heart", 1993, *Mol. and Cell. Biol.*, vol. 13, No. , pp. 2235–2246.

Ii, M., et al., "Molecular Cloning and Sequence Analysis of cDNA Encoding the Macrophage Lectin Specific for Galactose and N–Acetylgalsactosamine", 1990, *J. Biol. Chem.*, vol. 265, No. 19, p. 11295–11298.

Oda, S., et al., "Purification and Characterization of a Lectin–Like Molecule Specific for Galactose/N–Acetyl–Galactosamine from Tumoricidal Macrophages", 1988, *J. Biochem.*, vol. 104, pp. 600–605.

(List continued on next page.)

*Primary Examiner*—Garnette D. Draper
*Attorney, Agent, or Firm*—Fish & Richardson P.C.

[57] ABSTRACT

Differentially expressed allograft genes, methods of screening therefor, and methods of diagnosing and treating allograft rejection and other conditions related to vascular inflammation, such as atherosclerosis.

8 Claims, 21 Drawing Sheets

OTHER PUBLICATIONS

Oda, S., et al., "Binding of Activated Macrophages to Tumor Cells Through a Macrophage Lectin and Its Role in Macrophage Tumoricidal Activity", 1989, *J. Biochem.*, vol. 105, pp. 105, pp. 1040–1043.

Sharon, N., et al., "Lectins as Cell Recognition Molecules", 1989, *Science*, vol. 246, pp. 227–234.

Kawasaki, T., et al., "Isolation and Characterization of a Receptor Lectin Specific for Galactose/n–Acetylgalactosamine From Macrophages", 1986, *Carbohydr. Res.*, vol. 151, pp. 197–206.

Ii, M., et al., "Structural Similarity Between the Macrophage Lectin Specific for Galactose/N–Acetylgalactosamine and the Hepatic Asialogylcoprotein Binding Protein", 1998, *Biochem. Biophys. Res. Commun.*, vol. 155, No. 2, pp. 720–725.

Ozaki, K., et al., "Expression of a Functional Asialoglycoprotein Receptor Through Transfection of a Cloned cDNA that Encodes a Macrophage Lectin", 1992, *J. Biologic. Chem.*, vol. 267, No. 13, pp. 9229–9235.

Valente, A.J., et al., "Mechanism in Intimal Monocyte–Macrophage Recuitment: A Special Role for Monocyte Chemotactic Protein–1", 1992, *Supplement III, Circulation*, vol. 86, No. 6, pp. III–20–III–25.

Auger, M.J., et al., *In* the Macrophage, C.E. Lewis and J. O'D. McGee, "Macrophage Surface Receptors", 1992, *IRL Press, Oxford*, Ch. 8, pp. 16–25.

Welsh, J., et al., "Arbitrarily Primed PCR Fingerprinting of RNA", 1992, *Nucl. Acids Res.*, vol. 20, No. 19, pp. 4965–4970.

Fyfe, A., et al., "Coronary Sinus Sampling of Cytokines After Heart Transplantation: Evidence for Macrophage Activation and Interleukin–4 Production Within the Graft", 1993, *J. Am. Coll. Cardiol.*, vol. 21, No. 1, pp. 171–176.

Laborda, J., "36B4 cDNA Used as an Estradiol–Independent mRNA Control is the cDNA for Human Acidic Ribosomal Phosphoprotein PO", 1991, *Nucl. Acids Res.*, vol. 19, No. 14, pp. 3998.

Liang, P., et al., "Distribution and Cloning of Eukaryotic mRNAs by Means of Differential Display: Refinements and Optimization", 1993, *Nucl. Acids. Res.*, vol. 21, No. 14, pp. 3269–3275.

Kumar, S., et al., "Identification of a Set of Genes With Developmentally Down–Regulated Expression in the Mouse Brain", 1992, *Biochem. Biophys. Res. Commun.*, vol. 185, No. 3, pp. 1155–1161.

Thommes, P., et al., "Properties of the Nuclear P1 Protein, a Mammalian Homologue of the Yeast Mcm3 Replication Protein", 1992, *Nucl. Acids Res.*, vol. 20, No. 5, pp. 1069–1074.

Liang, P., et al., "Differential Display and Cloning of Messenger RNAs from Human Breast Cancer versus Mammary Epithelial Cells", 1992, vol.52, pp. 6966–6968.

Sager, R., et al., "Identification by Differential Display of Alpha 6 Integrin as a Candidate Tumor Suppressor Gene", 1993, *FASEB J.*, vol. 7, No. 10, pp. 964–970.

Liaw, L., et al., "Comparison of Gene Expression in Bovine Aortic Endothelium In Vivo Versus In Vitro: Differences in Growth Regulatory Molecules", 1993, *Arterioscler. Thromb.*, vol. 13, No. 7, pp. 985–993.

Hershko, A., et al., "The Ubiquitin System for Protein Degradation", 1992, *Annu. Rev. Biochem.*, vol. 61 pp. 761–807.

Mayer, R.J., et al., "Ubiquitin in Health and Disease", 1991, *Biochimica et Biophys. Acta.*, vol. 1089, pp. 141–157.

Iris, F.J.M., et al., "Dense Alu Clustering and a Potential New Member of the NFκB Family Within a 90 Kilobase HLA Class III Segment", 1993, *Nature Genetics*, vol. 3, pp. 137–145.

Sargent, C.A., et al., "Identification of Multiple HTF–Island Associated Genes in the Human Major Histo–compatibility Complex Class III Region", 1989, *EMBO J.*, vol. 8, No. 8, pp. 2305–2312.

Stamper, H.B., et al., "An In Vitro Model of Lymphocyte Homing, I. Characterization of the Interaction between Thoracic Duct Lymphocytes and Specialized High–Endothelial Venules of Lymph Nodes", 1977, *J. Immunol.*, vol. 119, No. 2, pp. 772–780.

Butcher, E.C., et al., "Lymphocyte Adherence to High Endothelial Venules: Characterization of a Modified in Vitro Assay, and Examination of the Binding of Syngeneic and Allogeneic Lymphocyte Populations", 1979, *J. Immunol.*, vol. 123, No. 5, pp. 1996–2003.

Gessl, A., et al., "Expression of a Binding Structure for Sialic Acid Containing Glycoconjugates on Rat Bone Marrow–Derived Macrophages and its Modulaton by IFN, TNF–α, and Dexamethasone", 1989, *J. Immunol.*, vol. 142, No. 12, pp. 4372–4377.

Northern Analysis
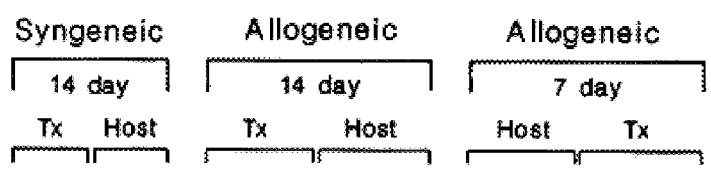
FIG. 2A
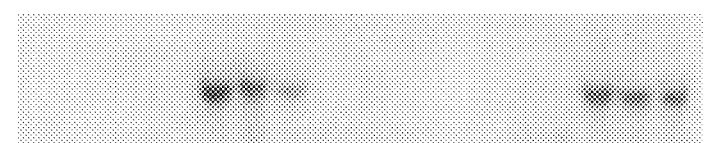
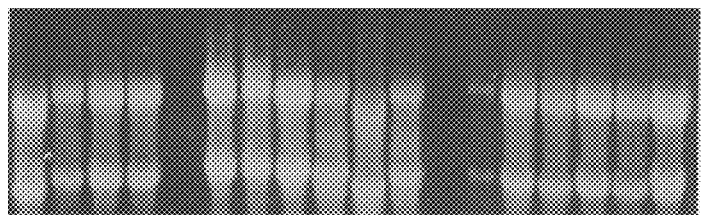
FIG. 2B

Differential mRNA Display

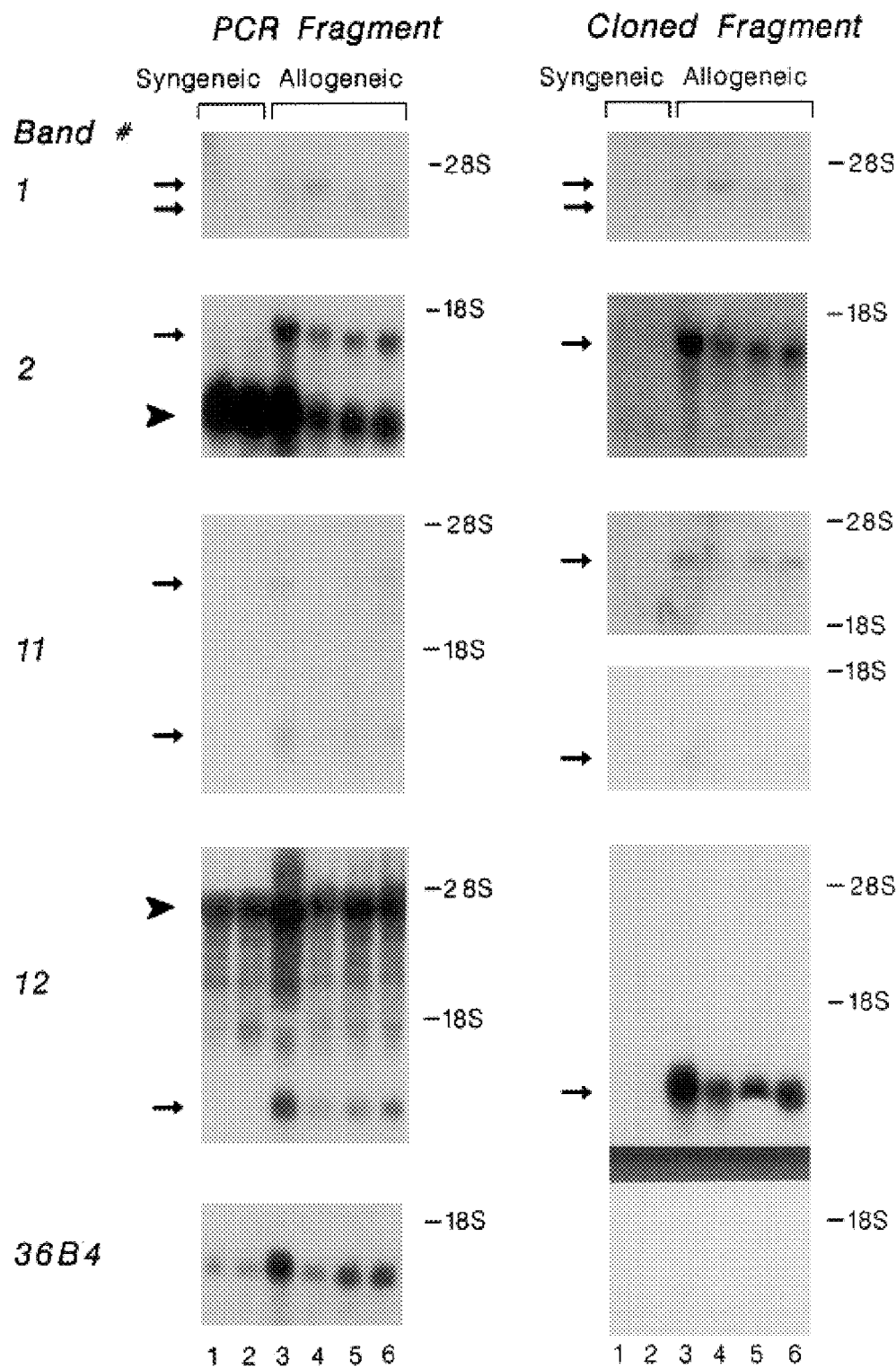

```
GAGGAGCCAGCCAACACACTGCAGCCTCATCTCCCCACCTAAGGCCACCAGCGT      60
CTGAGGAGCTATGAGCCAGGATTTGCAGGGAGGAAAAGCTTTGGACTGCTGAA     120
          M  S  Q  D  L  Q  G  G  K  A  F  G  L  L  K
AGCCCAGCAGAAGAGAGGTTGGATGGGATCAACAAGCACTTCCTGATCCAAGTA     180
 A  Q  Q  E  E  R  L  D  G  I  N  K  H  F  L  D  D  P  K  Y
CAGCAGTGATGAGGATCTGCAGTCCAAACTGGAGGCCCTTCAAGACGAAGTACATGGAGTT     240
 S  S  D  E  D  L  Q  S  K  L  E │ A  F  K  T  K  Y  M  E  F │
TGATCTGAATGGCAATGGAGATATCGATATTATGTCCTGAAGGAATGCTGGAGAAACT     300
│ D  L  N  G  N  G  D  I  D  I  M  S │ L  K  R  M  L  E  K  L
TGGGGTTCCCAAGACCCATCTAGAGCTGAAGAAATTAAGAGAGGTGTCCAGTGGCTC     360
 G  V  P  K  T  H  L  E  L  K  K  L  I  R  E  V  S  S  G  S
CGAGGAGACGTTCAGTTACTCTGACTTTCTCAGAATGATGCTGGGCAAGAGATCTGCCAT     420
 E  E  T  F  S  Y  S  D  F  L  R  M  M  L  G  K  R  S  A  I
CTTGAGAATGATTCTGATGTATGAGGAGAAAAACAAGAAGCCAACTGGTCC     480
 L  R  M  I  L  M  Y  E  E  K  N  K  E  H  Q  K  P  T  G  P
CCCAGCCAAGAAAGCTATTTCTGAGTTGCCCTAATTGGAGGTGGATATAACACGGTGGA     540
 P  A  K  K  A  I  S  E  L  P
CCGAGGACCTTCTAATGACAGCAGCATGGGAAAAGAAGCAGTTGTGAGCCAGAGTCA     600
AACTAAATAATGCTCCCTAGTGC

SEQ ID NO: 4
```

Northern Analysis

FIG. 15A
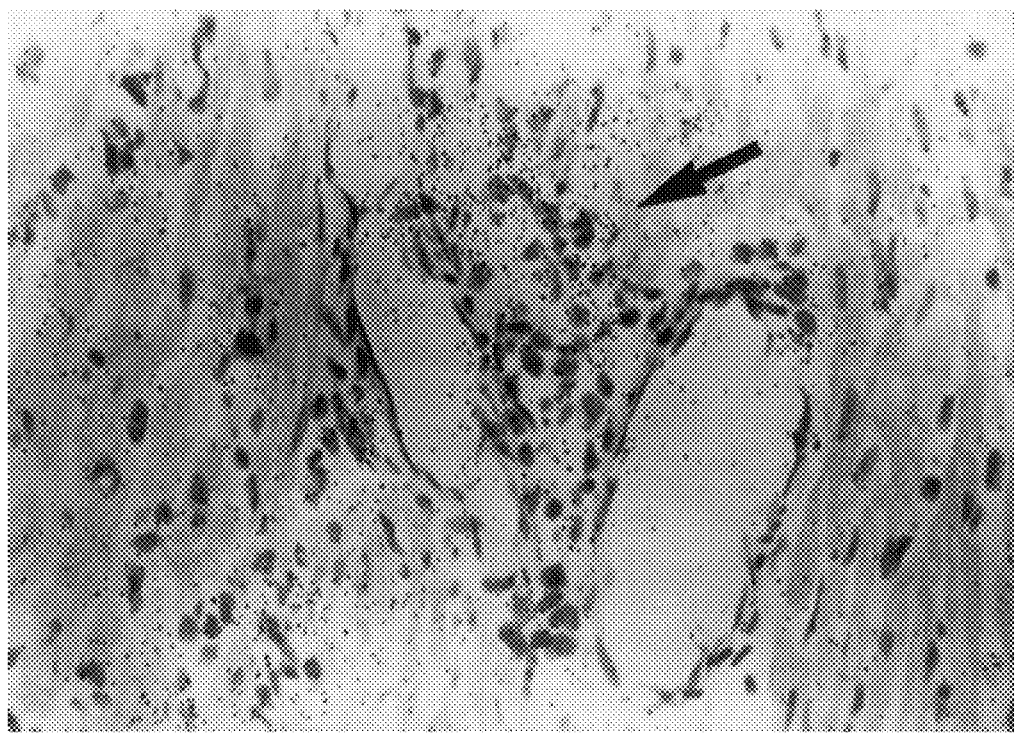
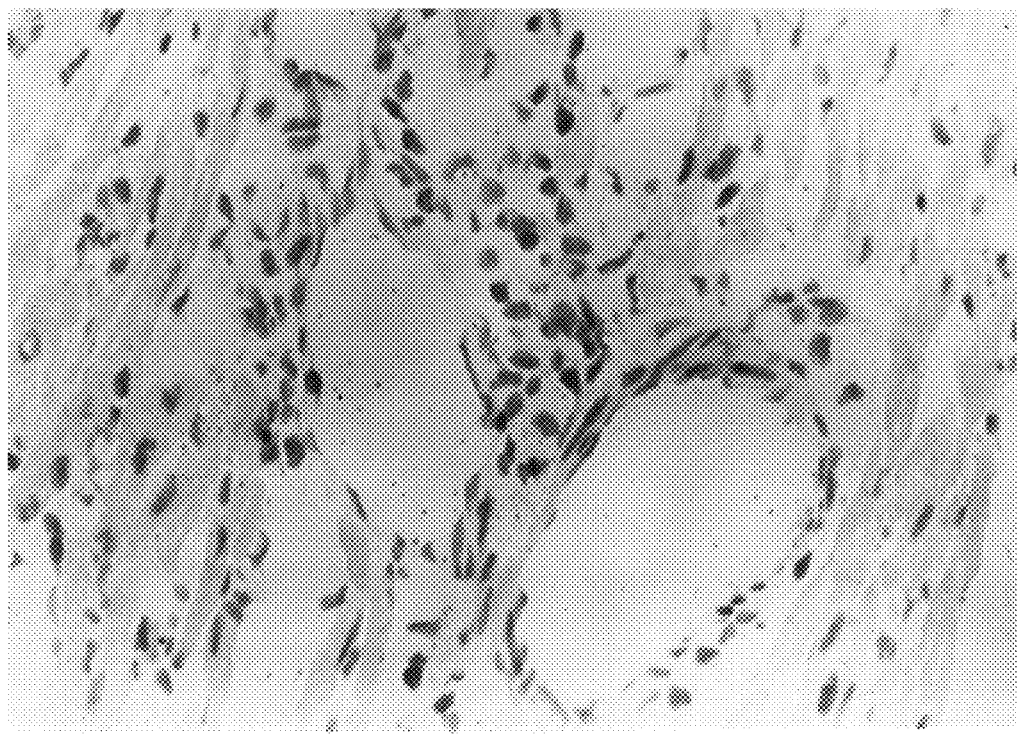
FIG. 15B

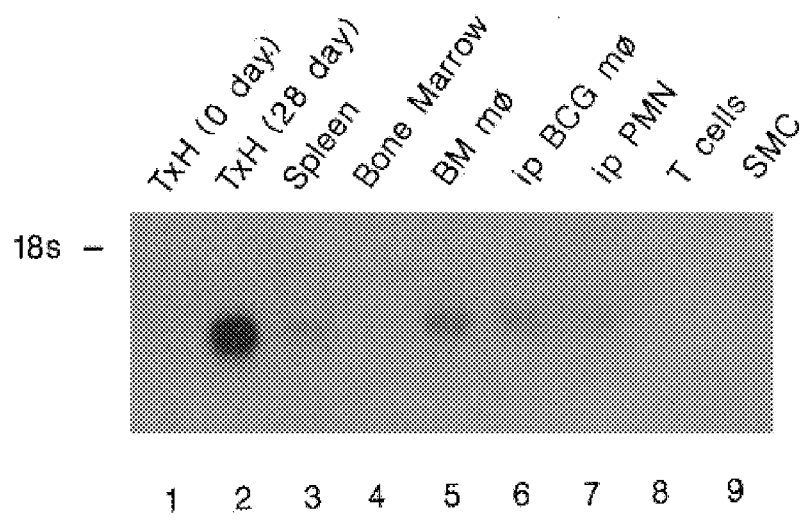
FIG. 16A
FIG. 16B
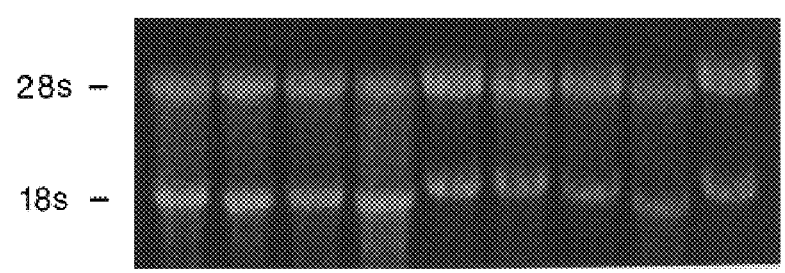
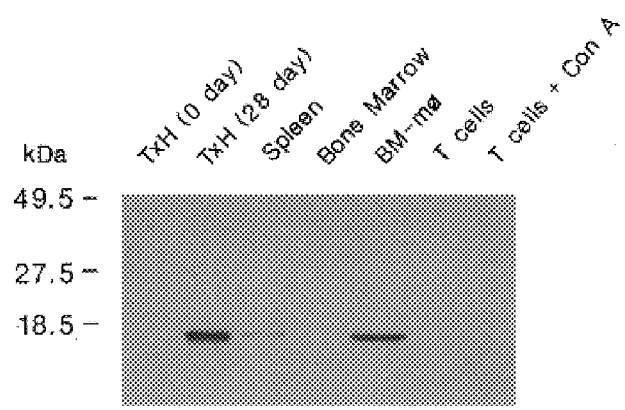
FIG. 17

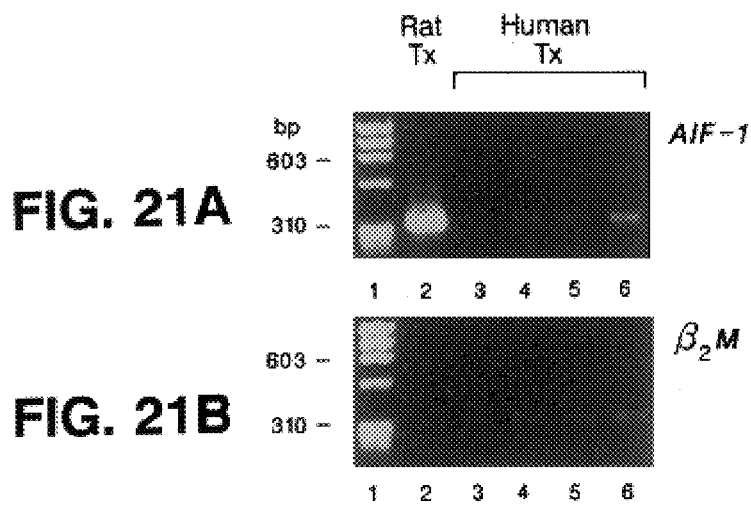
FIG. 21A
FIG. 21B
FIG. 21C
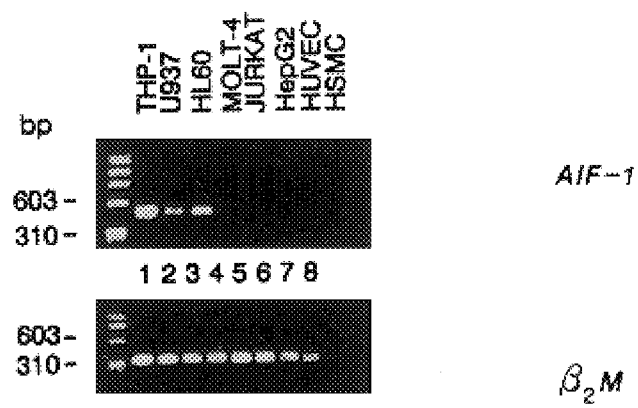
FIG. 24A
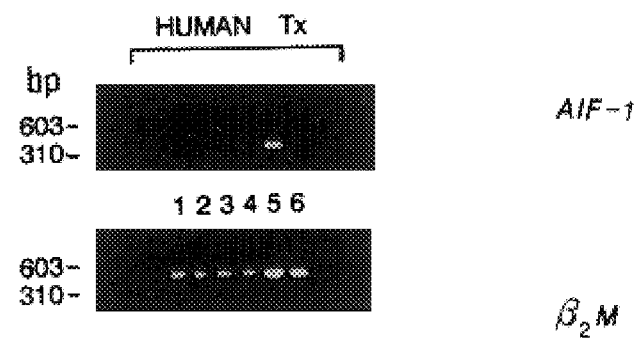
FIG. 24B

```
SEQ ID NO: 5  rAIF-1    MSQSKDLQGGKAFGLLKAQQEERLDGINKHFLDDPKYSSDEDLQSKLEAF  50
                        |||..:||||||||||||||||||||:||||.||||||||||||.|||:|
SEQ ID NO: 42 hAIF-1    MSQTRDLQGGKAFGLLKAQQEERLDEINKQFLDDPKYSSDEDLPSKLEGF  50 rAIF-1    KTKYMEFDLNGNGDIDIMSLKRMLEKLGVPKTHLELKKLIREVSSGSEET  100
                        |.|||||||||||||||||||||||||||||||||||||||:|||||||:|||
              hAIF-1    KEKYMEFDLNGNGDIDIMSLKRMLEKLGVPKTHLELKKLIGEVSSGSGET  100 rAIF-1    FSYSDFLRMMLGKRSAILRMILMYEEKNKEHQKPTGPPAKKAISELP    147
                        |||.||||||||||||:|||:|||||:..:|||:|||||||||||||
              hAIF-1    FSYPDFLRMMLGKRSAILKMILMYEEKAREKEKPTGPPAKKAISELP    147
```

FIG. 22

MEDIATORS OF CHRONIC ALLOGRAFT REJECTION (AIF-1) AND DNA ENCODING THEM

This application is a continuation-in-part of application Ser. No. 08/171,385, filed Dec. 21, 1993, now U.S. Pat. No. 5,527,884.

STATEMENT AS TO FEDERALLY SPONSORED RESEARCH

This invention was made with U.S. Government support under HL43318 awarded by the National Institutes of Health. The U.S. Government therefore has certain rights in the invention.

BACKGROUND OF THE INVENTION

The invention relates to tissue and organ transplantation.

The major limitation to long-term survival after organ transplantation in humans is the development of chronic rejection. Cardiac transplantation, for example, is frequently characterized by an obliterative arteriosclerosis with progressive thickening of the interior of the blood vessel that eventually results in ischemic injury (Schoen, F. J. and P. Libby, 1991, Cardiac Transplant Graft Arteriosclerosis, *Trends Cardiovasc. Med.,* 1:216–223; Sharples, L. D., N. Caine, P. Mullins, J. P. Scott, E. Solis, T. A. English, S. R. Large, P. M. Schofield, and J. Wallwork, 1991, Risk factor analysis for the major hazards following heart transplantation-rejection, infection, and coronary occlusive disease, *Transplantation,* 52:244–252; Cramer, D. V., 1993, Graft Arteriosclerosis in Heart Transplantation, R. G. Landes Company, Austin, Tex.). Studies of vessels from human heart transplant recipients have revealed an intimal hyperplasia that is concentric and diffuse, involves a spectrum of vessels, and is highly prevalent. Animal models have shown that in the first stage of arteriosclerotic thickening, monocytes/macrophages accumulate. In the intermediate stage, macrophages and smooth muscle cells both accumulate, and in the later more obliterative stage, smooth muscle cells predominate.

Chronic transplant rejection is likely to be a complex process mediated by a spectrum of factors which have been difficult to eliminate. Transplant arteriosclerosis occurs only in the donor heart and spares the host vessels. One hypothesis about the arteriosclerotic process holds that a chronic, cell-mediated immune response to alloantigens produces cytokines that mediate neointimal smooth muscle cell accumulation in the graft-derived vasculature, in a manner analogous to the process of delayed-type hypersensitivity (Schoen et al., supra), but little is known about factors that regulate the specific localization or function of mononuclear cells in the interstitium and vessels of cardiac allografts. The pathogenesis of transplant arteriosclerosis is unknown, and studies to elucidate the process have been limited by difficulty in obtaining useful clinical specimens.

SUMMARY OF THE INVENTION

The invention addresses these problems by providing methods to identify genes which are differentially expressed in allograft tissue undergoing rejection, to diagnose chronic rejection, and to treat patients undergoing transplant rejection. Furthermore, factors identified in association with chronic rejection also appear to play a role in other forms of arteriosclerosis.

As an alternative to conventional transcriptional analysis of selected known factors that could be involved in chronic rejection, screening assays which utilize a modification of the differential mRNA display technique were developed to identify potential mediators that are novel or have not been previously implicated in chronic rejection.

In one aspect, the invention features a method of identifying a gene which is differentially expressed in an allograft of a given tissue type compared to a syngraft of the same tissue type, by obtaining mRNA from the allografts and syngrafts, and determining whether the quantity of an allograft cDNA or transcript is increased or decreased compared to that of the corresponding syngraft transcript. An increase in the amount of a given transcript in tissue from an allograft compared to the amount of the corresponding transcript in corresponding tissue from a syngraft indicates that the given transcript encodes a mediator of allograft rejection. The term "differentially expressed" refers to a given allograft gene transcript, and is defined as an amount which is substantially greater or less than the amount of the corresponding syngraft transcript. By the term "gene transcript" is meant a mRNA or cDNA.

In one embodiment, the amount of allograft transcript is at least four times the amount of the corresponding syngraft transcript; preferably, the amount of syngraft transcript is absent or undetectable.

In another aspect, the invention features a method of diagnosing (1) allograft rejection, or (2) preatherosclerotic vascular inflammation and/or vascular injury, by detecting an increase in expression of a differentially expressed allograft gene at the site of the rejection, inflammation, or injury. Detection of increased expression of genes previously identified using the screening assays of the invention, such as allograft inflammatory factor-1 (AIF-1), allograft inflammatory factor-2 (AIF-2), ubiquitin, P1, or galactose/N-acetylgalactosamine (Gal/GalNAc) macrophage lectin, can be used to diagnose transplant rejection in a patient. Detection of expression of these genes can be accomplished by measuring gene transcripts, e.g., mRNA or cDNA, using standard techniques such as differential display mRNA analysis, polymerase chain reaction (PCR), in situ hybridization, or Northern blotting techniques, or by measuring the polypeptide product using known methods, such as Western blotting techniques, fluorescein-activated cell sorting (FACS), immunohistochemistry, immunoassays, or non-invasive imaging.

The invention also features an isolated DNA which encodes AIF-1, e.g., rat AIF-1 cDNA (SEQ ID NO:4) or human AIF-1 cDNA (SEQ ID NO:43). An isolated DNA which hybridizes at high stringency to a 20 nucleotide fragment of SEQ ID NO: 1, 4, or 43; and an isolated DNA which encodes an AIF-1 polypeptide, e.g., rat AIF-1 polypeptide (SEQ ID NO:5) or human AIF-1 polypeptide (SEQ ID NO:42), are also included. A substantially pure preparation of an AIF-1 polypeptide is also included. The DNA of the invention preferably encodes a mammalian AIF-1 polypeptide or functional fragment or isoform thereof, and most preferably encodes a rat or a human AIF-1 polypeptide.

Also within the invention is an isolated DNA which encodes AIF-2 polypeptide, or a functional or antigenic fragment thereof. Such a DNA may include the sequence of SEQ ID NO: 2, 3, 8, 9, 10, 11, 12, 13, 14, 15, 16, 17, 18, 19, 20, 21, 22, 23, 24, 25, 26, or 27; or may be an isolated DNA which hybridizes at high stringency to a DNA containing such a sequence. A substantially pure preparation of a polypeptide containing a sequence encoded by the DNA of SEQ ID NO: 2, 3, 8, 9, 10, 11, 12, 13, 14, 15, 16, 17, 18, 19, 20, 21, 22, 23, 24, 25, 26, or 27 is also within the invention. The DNA of the invention preferably encodes a mammalian AIF-2 polypeptide or functional fragment or isoform thereof, and most preferably encodes a rat or a human AIF-2 polypeptide. The invention encompasses isolated DNA containing part or all of the sequence of either AIF-1 or AIF-2. Also included are vectors containing the isolated DNA; cells, which can be prokaryotic or eukaryotic, containing the isolated DNA or vector; and methods of manufacturing recombinant AIF-1 or AIF-2, such as methods of culturing the cells containing isolated DNA of the invention under conditions permitting expression of the DNA. An "isolated DNA", as used herein, refers to a given DNA sequence which may be single stranded or double stranded, sense or antisense, and which has been removed from the sequences which flank it in a naturally occurring state, i.e., the sequences adjacent to the given DNA sequence in a genome in which it naturally occurs. The term includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic DNA fragment produced by PCR or restriction endonuclease treatment) independent of other DNA sequences. As used herein, the term "substantially pure" describes a compound, e.g., a polypeptide, which has been separated from components which naturally accompany it. Typically, a polypeptide is substantially pure when at least 10%, more preferably at least 20%, more preferably at least 50%, more preferably at least 75%, more preferably at least 90%, and most preferably at least 99% of the total material by dry weight in a sample is the polypeptide of interest. Purity can be measured by any appropriate method, e.g., polyacrylamide gel electrophoresis, column chromatography, or HPLC analysis. By the term "high stringency" is meant DNA hybridization and wash conditions characterized by relatively high temperature and low salt concentration, e.g., conditions described in Sambrook et al., 1989, *Molecular Cloning: a Laboratory Manual*, second edition, Cold Spring Harbor Press, Cold Spring Harbor, N.Y., e.g., 0.2×SSC, 0.1% SDS at 60° C. wash conditions.

In another aspect, the invention features a method of inhibiting (1) rejection of a transplanted tissue in an animal, or (2) atherosclerotic plaque formation at the site of vascular inflammation or injury, by introducing into the animal a compound which inhibits expression of a differentially expressed allograft factor that is upregulated during rejection of an allograft. An example of such a compound is an antisense DNA fragment complementary to the coding sequence or promoter of a differentially expressed allograft gene, e.g., Gal/GalNAc macrophage lectin, AIF-1, AIF-2, ubiquitin, or P1. Alternatively, rejection or other inflammatory processes could be inhibited by exploiting the differentially expressed factor as a means of targeting and killing cells which bear the factor on their surface. A recombinant or chemically conjugated hybrid toxin in which a toxic moiety (e.g., an enzymatically active fragment of diphtheria toxin or ricin, or a cytotoxic radioisotope) is linked to a ligand or antibody specific for the differentially expressed factor. The Gal/GalNAc macrophage lectin is an example of such a factor expressed on the surface of cells to be targeted by this method.

The invention also features a method of inhibiting (1) rejection of a transplanted tissue, or (2) formation of atherosclerotic plaques at the site of vascular inflammation or injury in an animal, by introducing into the animal a compound which inhibits binding of a cell-associated lectin to a carbohydrate ligand on the allograft. In preferred embodiments, the lectin is Gal/GalNAc macrophage lectin, and/or is present on the surface of a macrophage. The invention also includes compounds which inhibit binding of the lectin to its carbohydrate ligand, such as Gal/GalNAc macrophage lectin-specific antibody, a polypeptide which binds to Gal/GalNAc, a carbohydrate or compound containing a carbohydrate which binds to Gal/GalNAc macrophage lectin, or a compound containing a soluble carbohydrate-binding fragment of Gal/GalNAc macrophage lectin, all of which may be formulated in a pharmaceutical excipient for administration to animals.

In another aspect, the invention includes a screening assay to identify a candidate compound capable of inhibiting allograft rejection and/or atherosclerotic plaque formation, by contacting Gal/GalNAc macrophage lectin with its carbohydrate ligand in the presence and absence of a candidate compound, and measuring binding of the lectin to its carbohydrate ligand. A decrease in binding in the presence of a candidate compound compared to the level of binding in the absence of the candidate compound is an indication that the candidate compound inhibits allograft rejection and/or atherosclerotic plaque formation. This screening method may be carried out in vitro as well as in vivo.

Other features and advantages of the invention will be apparent from the following detailed description and other embodiments of the invention, and from the claims.

BRIEF DESCRIPTION OF THE DRAWINGS

FIG. 2A is a photograph of a Northern blot analysis showing upregulation of transcripts in an expanded series of 7- and 14-day cardiac allografts, but not in paired host hearts. Northern blot analysis using the transplanted heart (cardiac allograft) and host heart (exposed to the same circulation but histologically normal) from an additional 2 syngeneic and 6 allogeneic cardiac transplantations confirmed and extended the allograft-specific induction patterns. PCR-amplified DNA fragment from the differential display study hybridized to 1.4-kb transcripts found only in allogeneic transplanted hearts harvested at 7 and 14 days (lanes 5–7 and 14–16) but not to transcripts from the paired host hearts or syngeneic transplanted hearts.

FIG. 2B is a photograph of a RNA gel stained with ethidium bromide before transfer, to demonstrate that 20 µg of total RNA was loaded into each lane (with the exception of lane 11).

$^{32}$P incorporation in the PCR product band from dried gels was measured in PhosphorImager units. The linear relationship between amplified Gal/GalNAc macrophage lectin product bands and PCR cycle identifies the assay range where amplified product is proportional to the initial target mRNA.

Figure 4A:
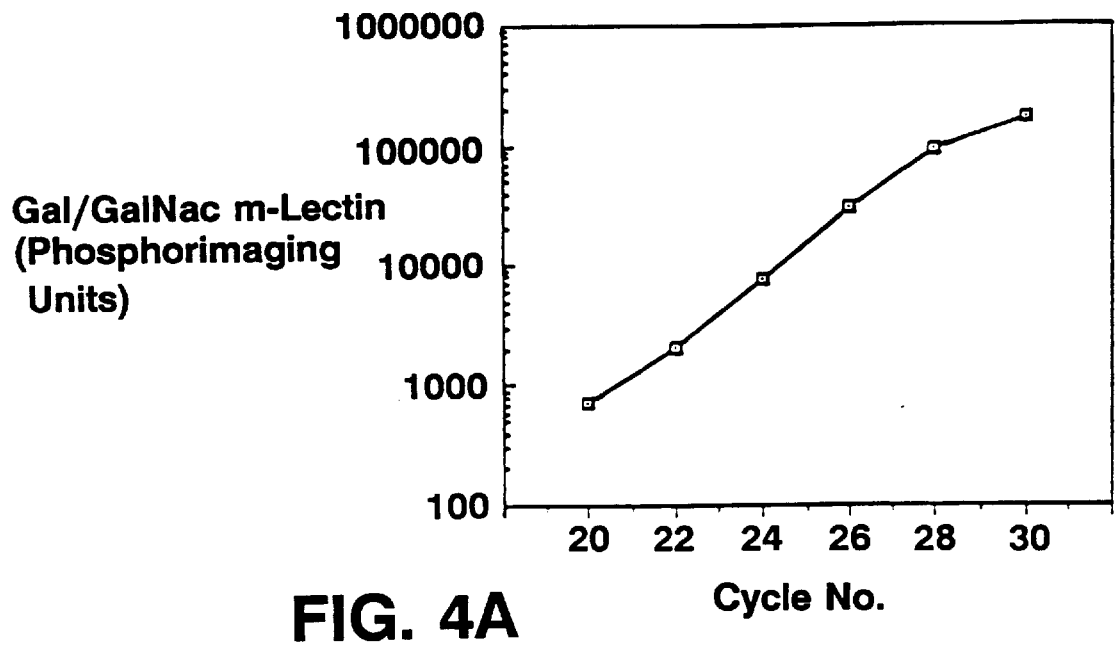
FIG. 4A is a graph of the linear range of Gal/GalNAc macrophage lectin reverse transcription-PCR assay. Rat cardiac allograft cDNA was amplified using specific Gal/GalNAc macrophage lectin primers and separated electrophoretically on 1% agarose gels.
Figure 4B:
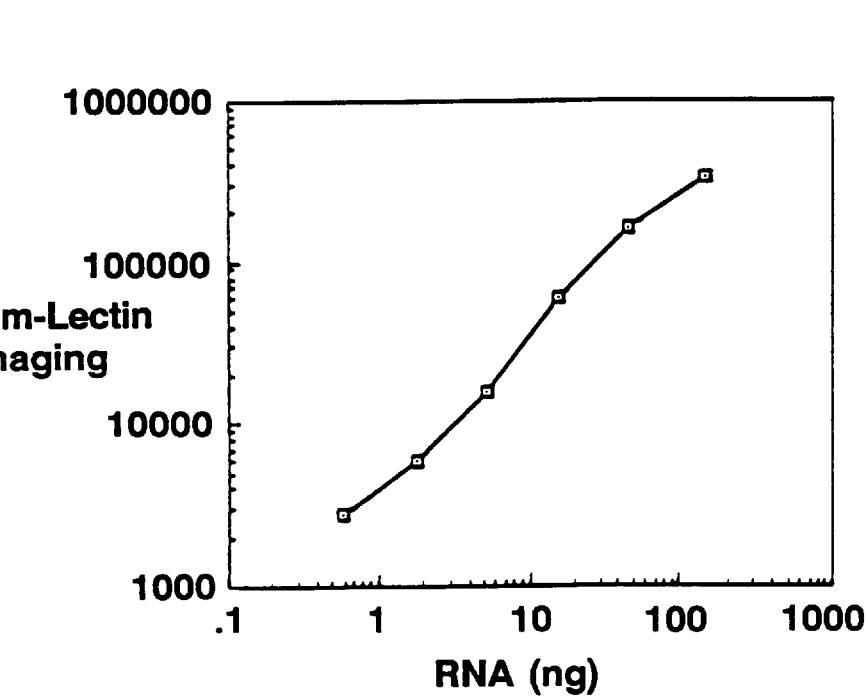

FIG. 4B is a graph showing the linear relationship between amplified Gal/GalNAc macrophage lectin product bands and added cDNA (represented as the calculated amount of total RNA in the PCR reaction, lower panel) which identifies the assay range where amplified product is proportional to the initial target mRNA.

Figure 5:
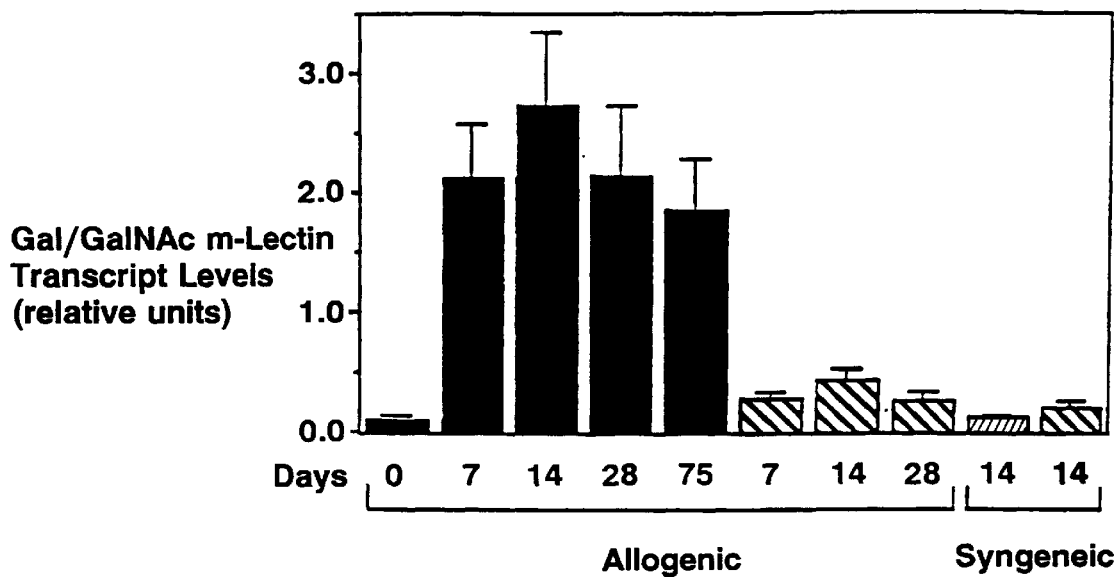

FIG. 5 is a bar graph showing a time course of Gal/GalNAc macrophage lectin gene expression after allogeneic cardiac transplantation. Corrected levels were derived by normalizing Gal/GalNAc macrophage lectin PCR values against those for the control gene, Glyceraldehyde 3 phosphate dehydrogenase (G3PDH), and are shown in relative units. There was a significant increase in cardiac transplant (or allograft) cDNA at 7, 14, 28, and 75 days (black bars) following transplantation compared with cDNA from the day-0 heart (harvested but not transplanted), paired host hearts (hatched bars), and a 14-day syngraft (stippled bar) (P<0.008). Data are plotted as means ± SEM and represent 4 separate PCR analyses.

Figure 6:
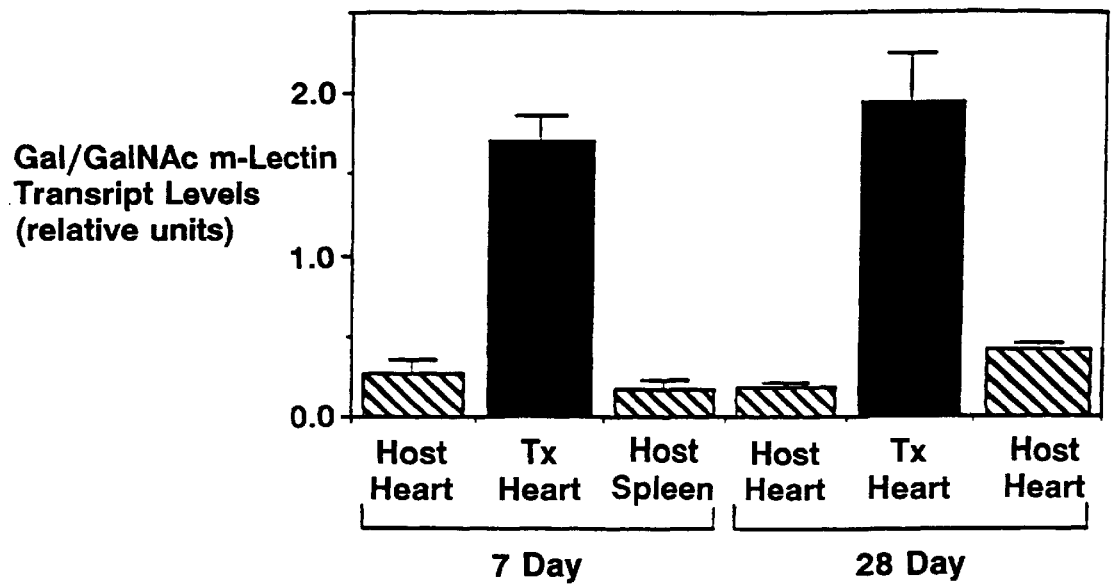

FIG. 6 is a bar graph showing upregulation of Gal/GalNAc macrophage lectin transcripts localized within the allografted heart. PCR analysis to identify relative differences in Gal/GalNAc macrophage lectin transcript levels was performed on a set of cDNAs that included the transplanted heart (black bars) and the matching host heart and spleen (hatched bars) from 2 additional allogeneic cardiac transplantations harvested at 7 and 14 days. Corrected Gal/GalNAc macrophage lectin levels were derived by normalizing the lectin PCR band value against that of the G3PDH control value. Gal/GalNAc macrophage lectin levels increased significantly in the transplanted hearts compared with the host spleens (rich in resident macrophages but not subject to local allogeneic stimulation) and the host hearts normal on histologic examination (P<0.0001). Data are plotted as means±SEM and represent 4 separate PCR analyses.

Figure 7:
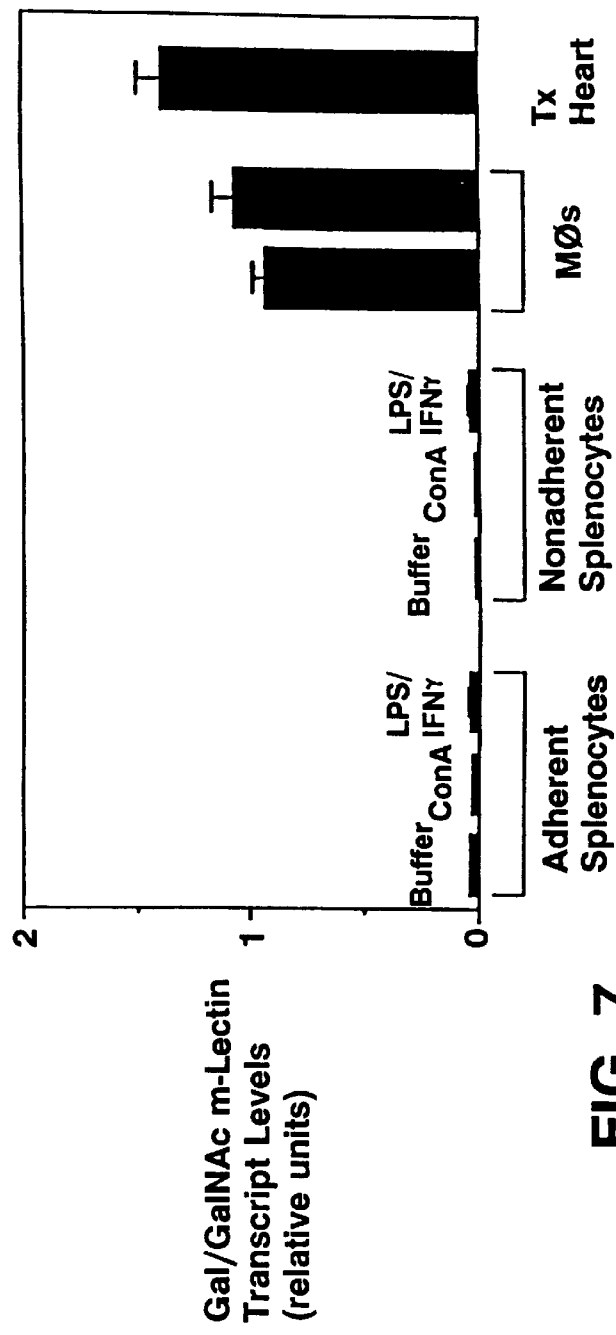

FIG. 7 is a bar graph showing an increase in Gal/GalNAc transcripts levels in exudative macrophages. Corrected Gal/GalNAc transcript levels were significantly higher in thioglycolate-elicited macrophages (P<0.0001) and cardiac allografts compared with adherent and nonadherent splenocytes even after 4 hours of stimulation with concanavalin A or lipopolysaccharide/interferon-γ. Data are plotted as means±SEM and represent 4 separate PCR analyses.

Figures 8A, 8B, 8C, 8D:
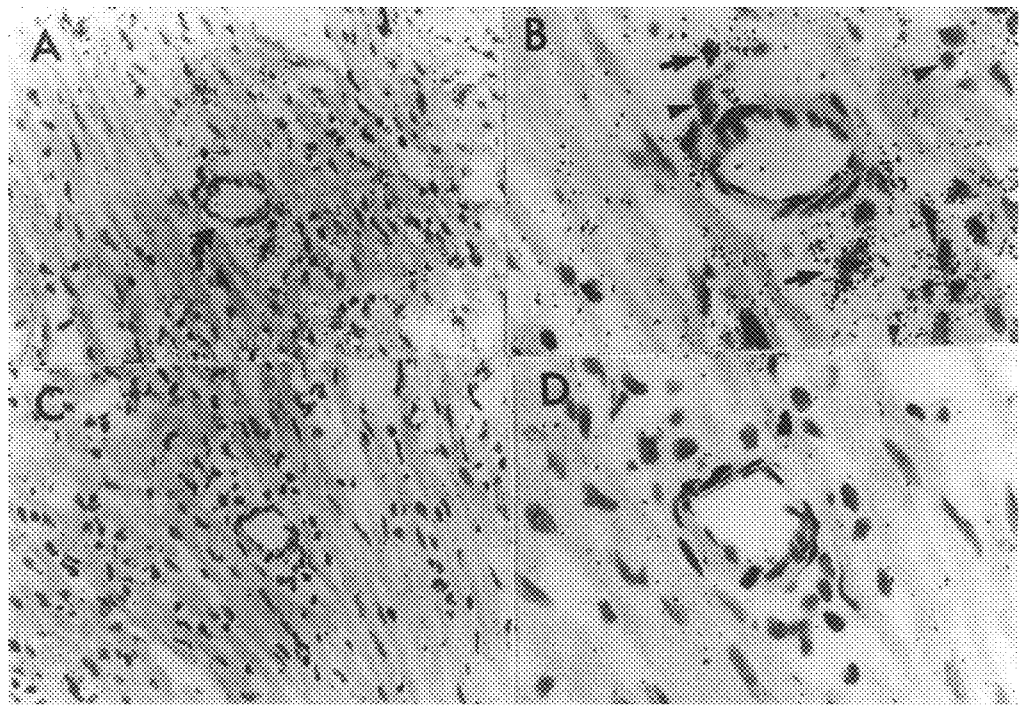

FIGS. 8A–8D are photographs of microscopic analyses of cardiac allograft cells showing in situ localization of Gal/GalNAc macrophage lectin mRNA. Sections were hybridized to $^{35}$S-labeled antisense (FIG. 8A and FIG. 8B) or sense (FIG. 8C and FIG. 8D) riboprobes. Arrows in lower-power sections (FIG. 8A and FIG. 8C) indicate the regions shown in higher magnification (FIG. 8B and FIG. 8D). Silver grains indicating hybridization of Gal/GalNAc macrophage lectin mRNA are clustered over a subset of inflammatory cells in the interstitium and perivascular spaces (FIG. 8A, 260×). Arrows mark representative positive mononuclear cells that are seen best at higher magnification (FIG. 8B, 600×). Arrowheads mark representative inflammatory cells without hybridization. Little hybridization is visible in adjacent noninflammatory cells such as cardiac myocytes. The sections hybridized with sense riboprobes show no significant hybridization (FIG. 8C, 260×) and (FIG. 8D, 600×).

Figure 9A:
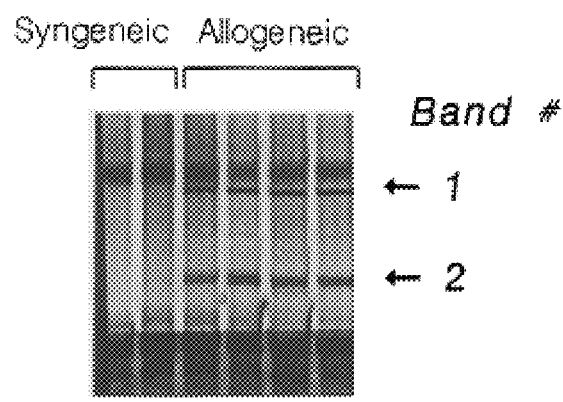
Figure 9B:
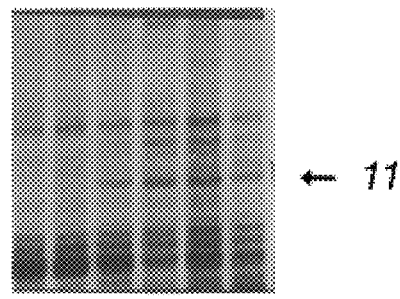
Figure 9C:
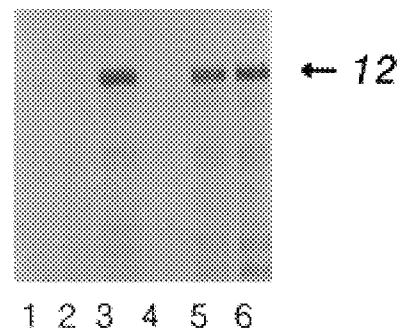

FIGS. 9A–9C are photographs of differential display gels comparing RNAs from syngeneic and allogeneic hearts. Total RNA was extracted from hearts after syngeneic (Lanes 1 and 2) and allogeneic (Lanes 3–6) transplantation and subjected to differential mRNA display analysis. Autoradiograms of amplified [γ-$^{35}$S]dATP-labeled PCR products (after electrophoresis on 6% polyacrylamide gels) are shown for three different primer combinations (FIGS. 9A–9C) that identified four distinct fragments (arrows) upregulated in the allogeneic group. Primer combinations included $T_{12}VC$ as 3' primer for all reactions and various 5'-primers: FIG. 9A, OPA-16 (AGCCAGCGAA) (SEQ ID NO: 28); FIG. 9B, OPA-04 (AATCGGGCTG) (SEQ ID NO: 29); and FIG. 9C, OPA-14 (TCTGTGCTGG) (SEQ ID NO: 30). Lane 4 in FIG. 9A shows a PCR reaction that failed.

FIGS. 10A and 10B are photographs of RNA blot analyses confirming allograft-specific gene induction for Bands 1, 2, 11, and 12 identified initially by differential mRNA display. Total RNA (20 μg) obtained from syngeneic (Lanes 1 and 2) or allogeneic (Lanes 3–6) transplantations were hybridized with cDNA probes generated by PCR reamplification of bands recovered from differential display gels (FIG. 10A) or cloned cDNA fragments (FIG. 10B). Arrows indicate allograft-specific hybridization patterns. Arrowheads indicate hybridization in all six lanes (which was considered nonspecific). RNA loading (bottom panel) was evaluated by reprobing the same blot with the rat ribosomal 36B4 homologue.

FIG. 11A is a representation of the nucleotide sequence and deduced amino acid sequence of the rat AIF-1 cDNA (SEQ ID NO: 4). Nucleotide numbering is indicated on the right and amino acid numbering is on the left. The boxed area indicates the region of the EF-hand-like motif (with the conserved loop segment shaded). A putative polyadenylation site is underlined.

Figure 11B:
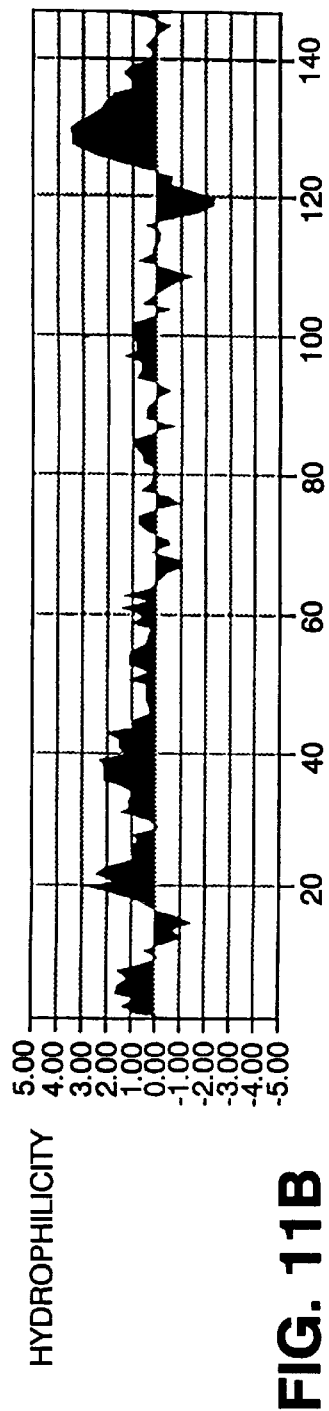

FIG. 11B is a graph showing the AIF-1 hydrophilicity plot generated with the Kyte-Doolittle algorithm. Regions of hydrophilicity are above the center line.

Figure 12:
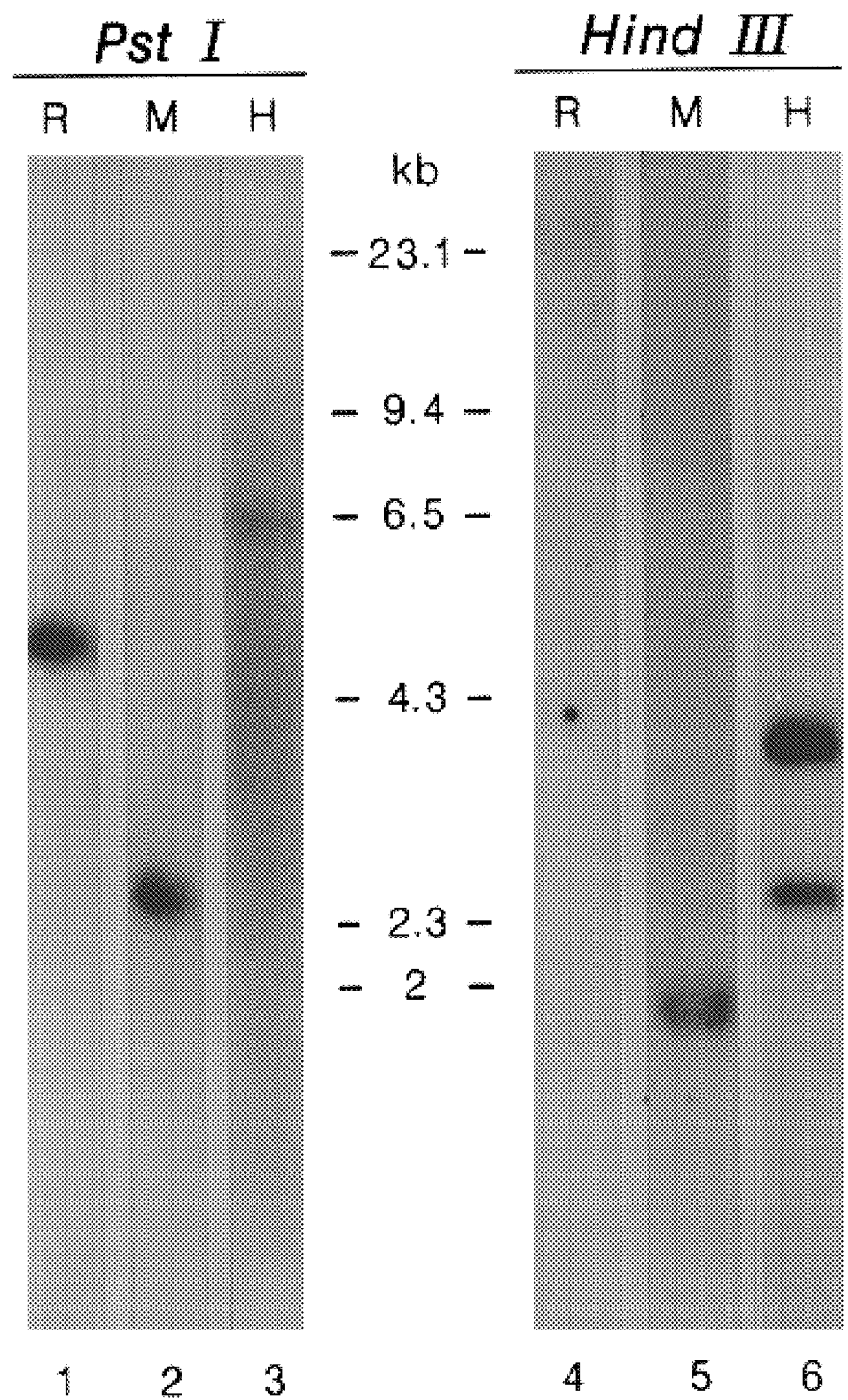

FIG. 12 is a genomic Southern analysis showing a representative autoradiogram from a blot hybridized with the $^{32}$P-labeled rat AIF-1 cDNA. Genomic DNA extracted from rat (R), mouse (M), and human (H) tissue samples was digested with the restriction enzymes indicated above the blots.

Figure 13A:
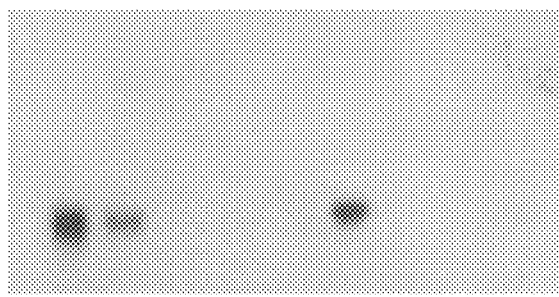

FIG. 13A is a representative autoradiogram from a Northern blot containing total RNA extracted from the indicated rat organs after hybridization with $^{32}$P-labeled AIF-1 cDNA. AIF-1 transcripts of 0.7 kb are visible in the 28-day cardiac allograft (lane 2), the spleen (lane 3), and the testis (lane 7).

Figure 13B:
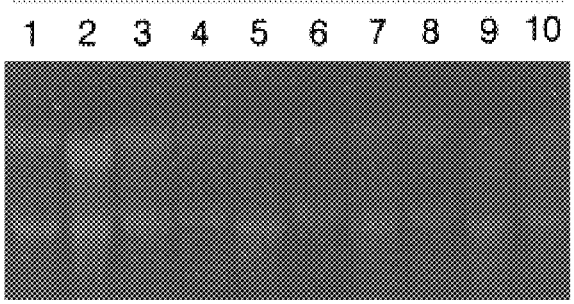

FIG. 13B is the same RNA gel as in FIG. 13A, stained with ethidium bromide before transfer to demonstrate loading in each lane.

Figure 14:
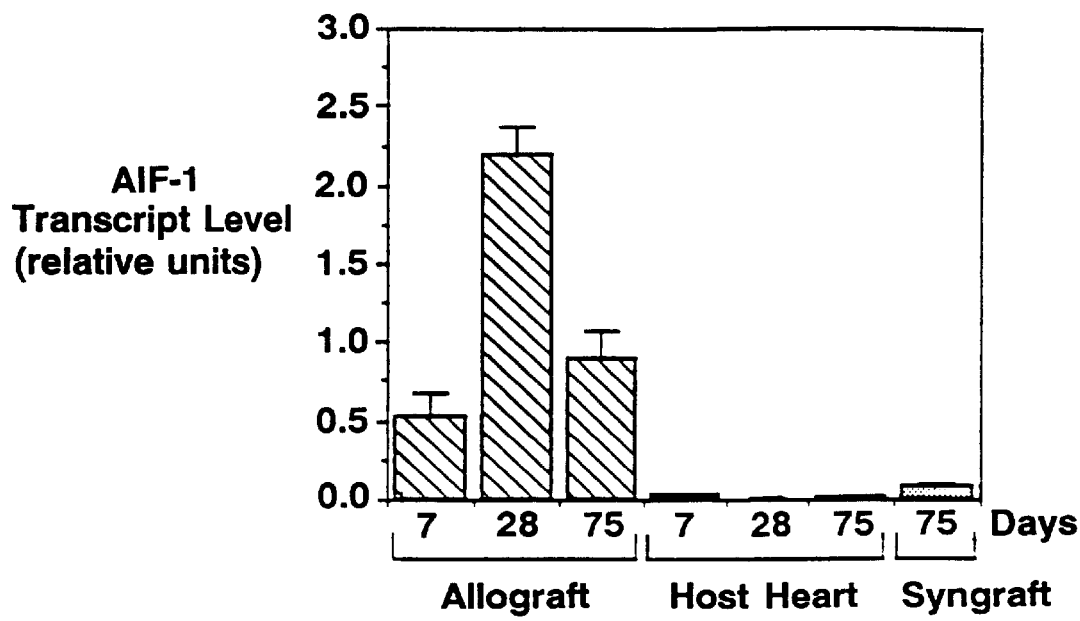

FIG. 14 is a graph illustrating the time course of AIF-1 gene expression after allogenic cardiac transplantation. Corrected levels were derived by normalizing AIF-1 $^{32}$P-reverse-transcriptase PCR values against those for the control gene, C3PDH, and are shown in relative units. Levels increased significantly in cardiac allograft cDNA at 7, 28, and 75 days after transplantation (hatched bars) compared with cDNA from paired host hearts (black bars) and day-75 syngrafts (stippled bar) ($p<0.003$). Values are shown for a representative experiment on two transplants per group. Data are plotted as means±SEM and represent three separate PCR analyses.

FIGS. 15A and 15B are photomicrographs illustrating in situ localization of AIF-1 transcripts in rat cardiac allografts. Frozen sections were hybridized with $^{35}$S-UTP-labeled antisense (FIG. 15A, ×300) and sense (FIG. 15B, ×300) riboprobes. Silver grains indicating hybridization of AIF-1 mRNA are clustered over mononuclear inflammatory cells in the perivascular (arrow) and interstitial spaces.

FIG. 16A is a representative autoradiogram of a Northern blot illustrating AIF-1 transcript expression in isolated rat cell populations. The various lanes contain total RNA extracted from cardiac allografts (lanes 1 and 2), spleen (lane 3), bone marrow cells (lane 4), macrophages derived from bone marrow (lane 5), BCG-elicited peritoneal macrophages (lane 6), casein-elicited peritoneal neutrophils (lane 7), T lymphocytes purified from a splenocytes suspension (lane 8), and arctic smooth muscle cells (lane 9).

FIG. 16B is the same RNA gel stained with ethidium bromide to demonstrate loading.

FIG. 17 is a Western blot analysis of AIF-1 antigen in various cell types. Western blots containing protein extract from the tissues or cell populations indicated were immunostained with rabbit anti-AIF-1 serum. Chemoluminescent detection shows a band of 17-kD in extracts from a day-28 cardiac allograft (lane 2), spleen (lane 3), and bone marrow-derived macrophages (lane 5) but not in extracts from a host heart (lane 1), femoral bone marrow cells (lane 4) or unstimulated (lane 6) or Concanavalin A-stimulated T lymphocytes (lane 7).

Figure 18A:
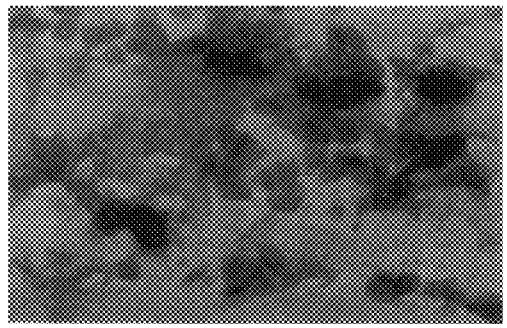
Figure 18D:
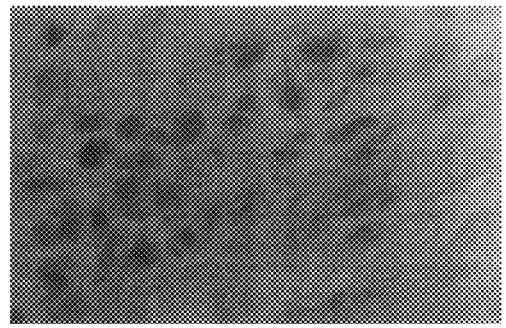
Figure 18B:
Figure 18E:
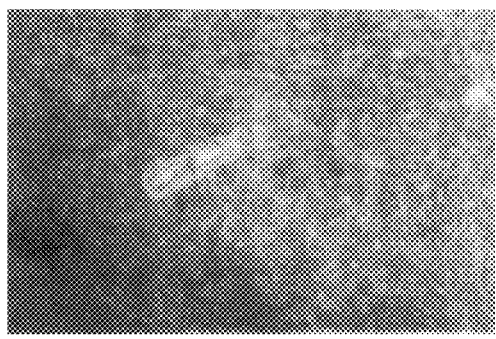
Figure 18C:
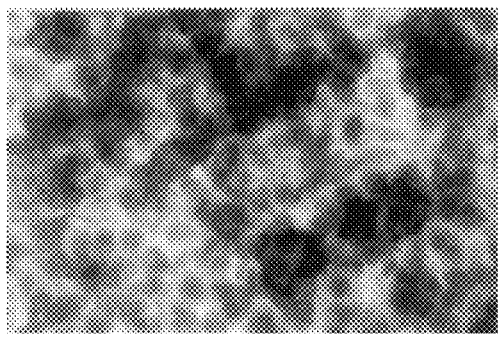
Figure 18F:
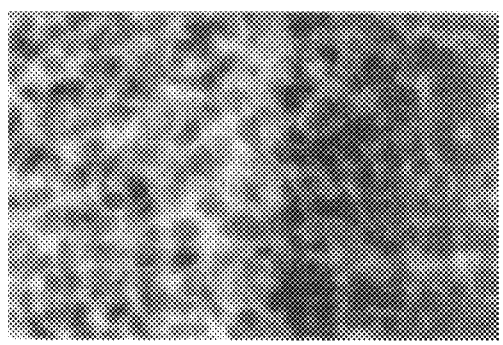

FIGS. 18A–18F are a series of photomicrographs illustrating immunostaining of the AIF-1 antigen in various tissue sections. Cells showing AIF-1-positive staining in the cytoplasm of a subset of mononuclear cells (FIGS. 18A–C) are visible in the interstitium of a 14-day cardiac allograft (FIG. 18A, ×940) and in the splenic red pulp (FIG. 18B, ×80 and FIG. 18C, ×940). No staining is visible if the primary antibody is omitted (FIGS. 18D–F).

Figure 19A:
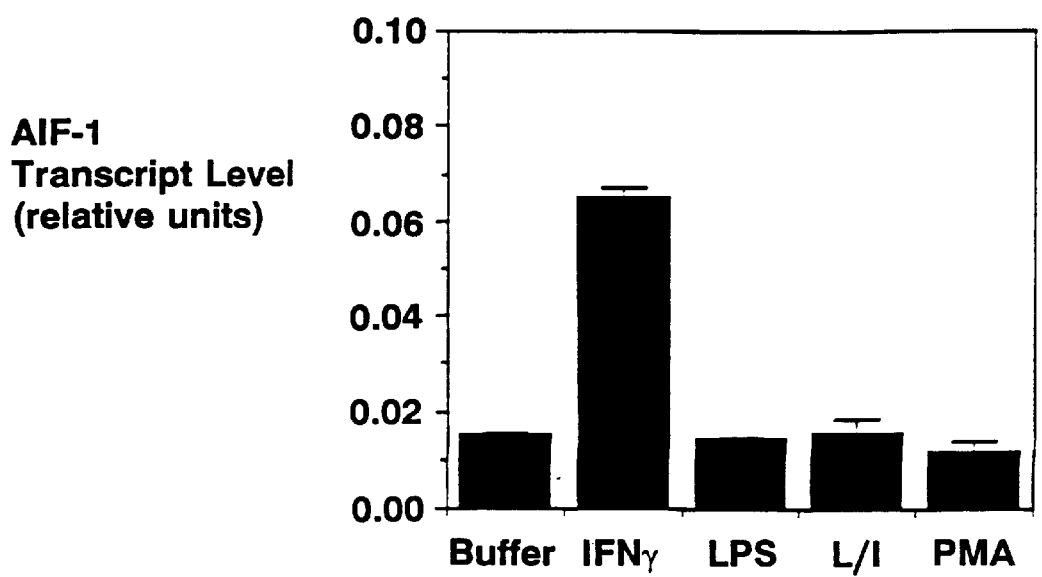

FIG. 19A is a bar graph illustrating the upregulation of AIF-1 transcript levels by IFN-γ in vitro. Corrected AIF-1 transcript levels were significantly higher in IFN-γ-treated J774A.1 cells ($p<0.0001$) compared with cells treated with buffer, LPS, combined LPS and IFN-γ (L/I) or phorbol 12-myristate-13-acetate (PMA) (24 h).

Figure 19B:
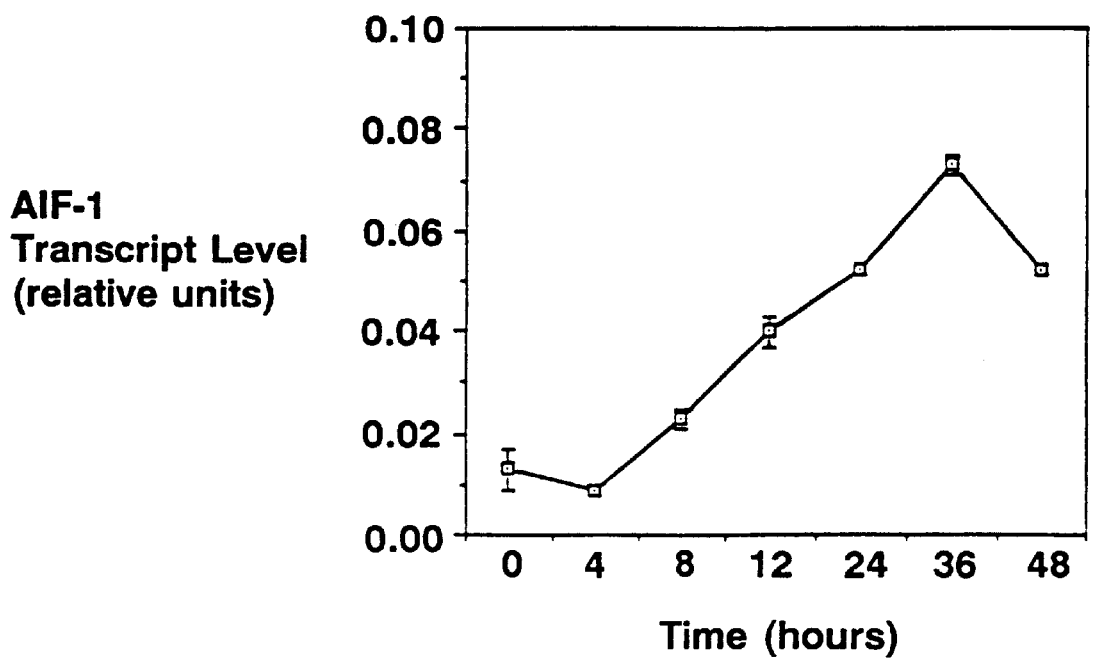

FIG. 19B is a graph illustrating the time-dependent increase in AIF-1 transcript levels in J774A.1 cells cultured in the presence of 100 units/ml IFN-γ for the indicated periods.

Figure 19C:
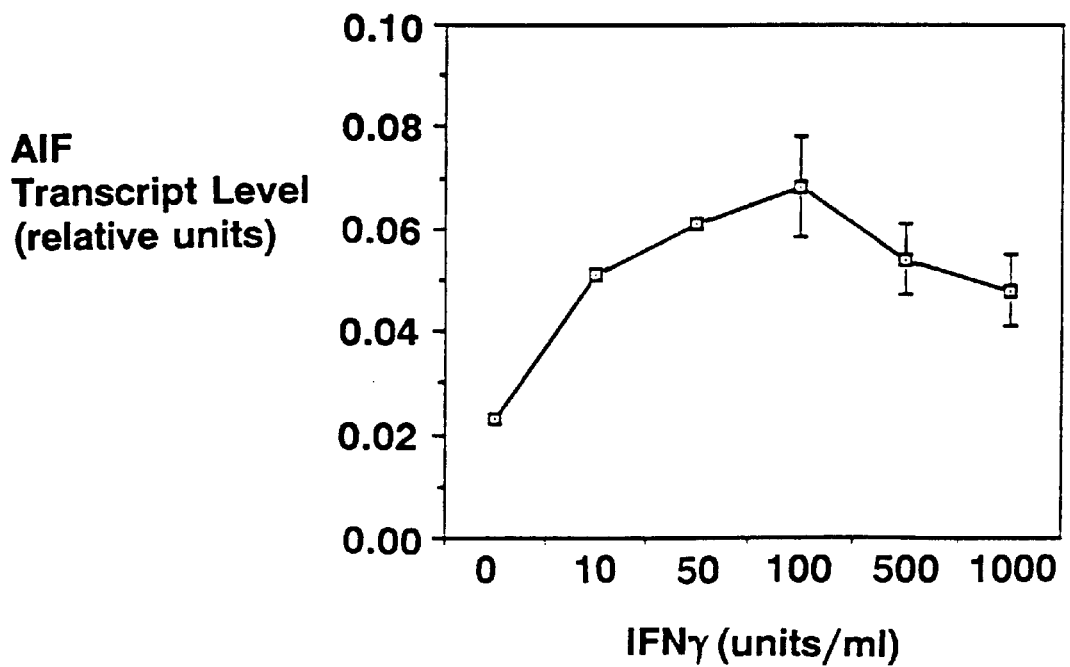

FIG. 19C is a graph illustrating the dose-response in J774A.1 cells of IFN-γ-induced increases in AIF-1 transcript levels after 24 h of stimulation. In each of FIGS. 19A–19C, data are plotted as means±SEM and represent three separate PCR analyses.

Figure 20A:
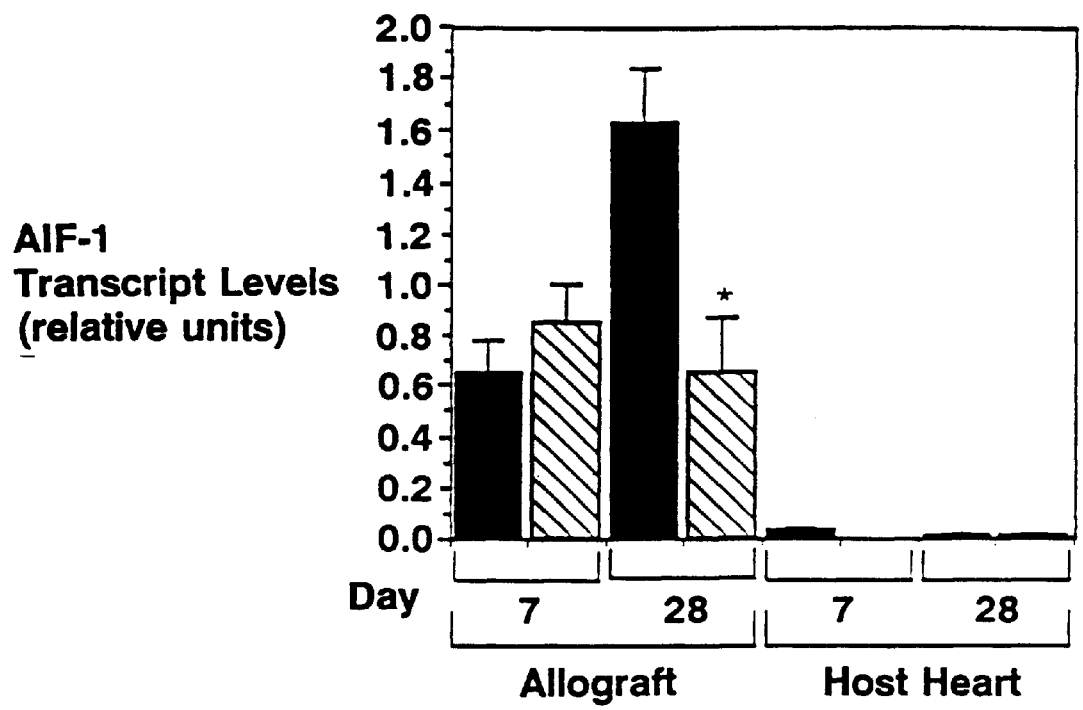
Figure 20B:
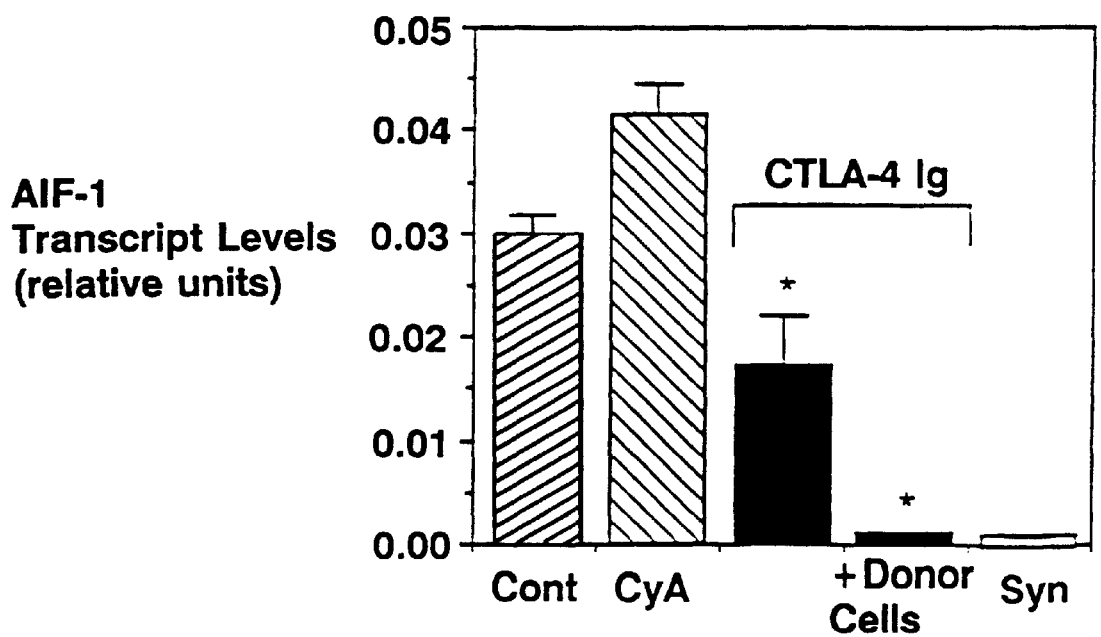

FIGS. 20A and 20B are bar graphs demonstrating that modulation of the allogeneic immune response decreases AIF-1 transcript levels in cardiac allografts. In FIG. 20A, the effect of EFAD diet is illustrated. Corrected AIF-1 transcript levels decreases significantly in day-28 cardiac allografts harvested from rats fed the EFAD diet (hatched bars) in comparison with allografts harvested from rats fed a control diet (black bars) ($p<0.0001$). In FIG. 20B, the effect of CTLA-4 Ig treatment is shown. Corrected AIF-1 transcript levels were significantly lower in cardiac allografts harvested at day 75 from rats treated with CTLA-4 Ig (black bar) ($p<0.0001$) in comparison with allografts from control rats (stippled bar) or allografts from cyclosporine A-treated animals (hatched bar). Administration of CTLA-4 Ig in combination with donor cells further decreased AIF-1 transcripts to a level similar to that observed in syngrafts (white bar) ($p<0.0001$). Data are plotted as means±SEM from two or three transplants per group and represent three separate PCR analyses.

FIGS. 21A–C are photographs of gels illustrating the identification of AIF-1 gene transcripts in transplant endomyocardial biopsies. In FIGS. 21A and 21B, ethidium-stained agarose gels are shown containing RT-PCR products amplified using primers for AIF-1 (FIG. 21A) and the reference gene, B-2-microglobulin (FIG. 21B). Bands of variable intensity are seen in lanes 2–6 representing endomyocardial biopsies from human heart allografts (lane 2–6) compared with the control cDNA from 28 day rat cardiac allografts. In FIG. 21C, Southern blot analysis of the same products shows hybridization to the lanes (3–6) with a nested human AIF-1 $^{32}$P labeled oligonucleotide probe.

FIG. 22 is a comparison between the deduced amino acid sequences for the AIF-1 coding region of rat (upper) (SEQ ID NO: 5) and human (lower) (SEQ ID NO: 42) cDNAs, showing 90% identity (1) and 95% similarity (.or:).

Figure 23A:
Figure 23C:
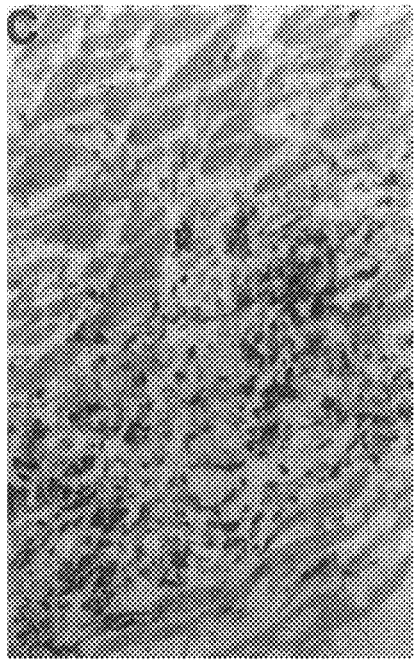
Figure 23B:
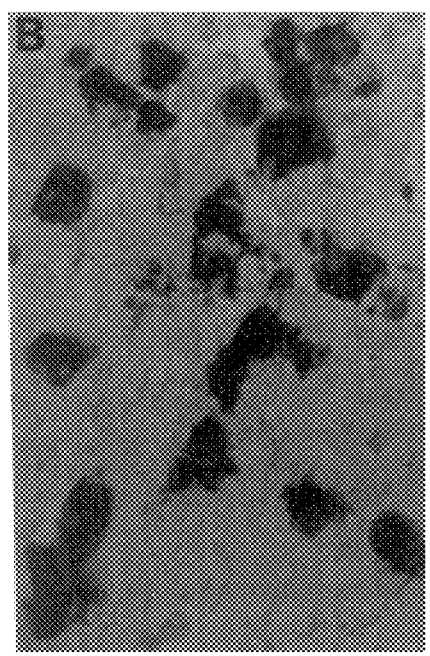

FIGS. 23A–D are photomicrographs of human cardiac allograft sections immunostained with anti-rat-AIF-1 antibody (FIGS. 23A (low magnification) and 23B (high magnification), or the anti-CD68 antibody (FIGS. 23C (low magnification) and 23D (high magnification). AIF-1 staining localizes to mononuclear cells found within the interstitium and perivascular spaces of cardiac allografts. These mononuclear cells are most likely macrophages, given that in serial sections, cells from these regions stain positive for the macrophage marker CD68.

FIG. 24A is an ethidium stained agarose gel which contains RT-PCR products amplified using primers for AIF-1 (upper panel) and the reference gene, B-2-microglobulin (lower panel). AIF-1 transcripts were amplified from cDNAs derived from the macrophage like cell lines THP-1, U937, and HL-60 (lanes 1–3), but were absent in T cell lines MOLT-4 and Jurket, HepG2 cells, HUVE cells, and HSCM cells (lanes 4–8).

FIG. 24B is an ethidium stained agarose gel which contains RT-PCR products amplified using primers for AIF-1 (upper panel) and the reference gene, B-2-microglobulin (lower panel). AIF-1 transcripts were amplified to various degrees from cDNAs derived from each of six endomyocardial biopsies from human cardiac allografts.

DETAILED DESCRIPTION

Lewis to F344 Rat Cardiac Transplantation

A rat heterotopic abdominal cardiac transplantation model was used to study transplant arteriosclerosis and cardiac rejection. (Cramer et al., 1993, supra; Adams, D. H., N. L. Tilney, J. J. Collins, and M. J. Karnovsky, 1992, Experimental graft arteriosclerosis. I. The Lewis-to-F344 allograft model, *Transplantation*, 53:1115–1119.) The combination of Lewis rat donors and F344 rat recipients results in long-term graft survival and a time-dependent development of arteriosclerotic lesions that resemble those in human transplant vessels on histologic examination (Cramer et al., 1993, supra; Adams et al., supra), and thus is a suitable animal model for this disease. Immunohistochemical studies using antibodies against monocytes, T-cells, and smooth muscle cells have shown that arteriosclerotic lesions develop in 3 distinct stages (Cramer, D. V., G. D. Wu, F. A. Chapman, E. Cajulis, H. K. Wang, and L. Makowka, 1992, Lymphocytic subsets and histopathologic changes associated with the development of heart transplant arteriosclerosis, *J. Heart Lung Transplant*, 11:458–466; Adams, D. H., L. R. Wyner, and M. J. Karnovsky, 1993, Experimental graft arteriosclerosis. II. Immunocytochemical analysis of lesion development, *Transplantation*, 56:794–799). In the first 30 days, the neointimal lesions are composed of infiltrating inflammatory cells (rather than smooth muscle cells), which are predominantly macrophages with fewer lymphocytes. Between 45 and 90 days, the infiltrating inflammatory cell population in the neointima decreases as intimal smooth muscle cells appear. In the last phase (beyond 90 days), the neointima is maximally expanded, often obliterative, and composed predominantly of smooth muscle cells with fewer infiltrating mononuclear cells. The early and persistent presence of monocytes/macrophages in the first stage of arteriosclerosis suggests a prominent role for the macrophage in the initial phase of chronic rejection. To date there are few studies examining specific molecular mechanisms that may regulate the infiltration or function of macrophages in chronically rejecting hearts.

Heterotopic abdominal cardiac transplantation was performed using Lewis donor hearts as described (Adams et al., supra) in an allogeneic combination involving F344 recipients. The syngeneic combination, involving Lewis recipients, was performed to assess the contribution of surgical manipulation to the inflammatory response. Lewis hearts that had been harvested but not transplanted were used as reference groups matching the strain of donor or grafted hearts. At the time of harvest, both the host (recipient) and the transplanted hearts were collected for histologic analysis and RNA extraction. The host heart served as a reference that had been exposed to the same circulation but was normal on histologic examination. In some studies, the host spleen was also harvested for a comparison of transcription patterns in an organ rich in inflammatory cells but free of local allogeneic stimulation.

Transplanted hearts were harvested at 7 and 14 days prior to the development of neointimal thickening. This strategy allowed the detection of transcriptional changes preceding functional changes. At the time of harvest, midventricular sections were taken for histologic analysis and snap frozen in liquid nitrogen for RNA extraction.

RNA Isolation and Northern Analysis

Heterotopic abdominal cardiac transplantations were performed and samples were collected as described (Russell, M. E., Adams, D. J., Wyner, L., Halnon, N. J., Yamashita, Y. & Karnovsky, M. J., 1993, *Proc. Natl. Acad. Sci. USA*, 90:6086–6090; Adams, D. H., Tilney, N. L., Collins, J. J. & Karnovsky, M. J., 1992, *Transplantation*, 53:1115–1119, both of which are herein incorporated by reference). For allogeneic transplantations, Lewis rats were used as graft donors and F344 rats were used as recipients. Total cellular RNA was extracted from heart tissue with RNAzol B (Tel-Test, Friendwoods, Tex.) according to the manufacturer's instructions. Samples of total RNA (20 μg) were fractionated in 1% formaldehyde/agarose gels and transferred onto nylon-supported nitrocellulose (Micron Separation, Boston, Mass.) by standard capillary blotting techniques. Equivalent loading of samples was verified by ethidium bromide staining of the ribosomal bands. Specific probes were generated by labeling reamplified or cloned cDNA fragments with [$\alpha^{32}$P]dCTP by using a random prime DNA labeling kit (Boehringer Mannheim Biochemicals, Chicago, Ill.). Nucleic acids were cross-linked to the membrane with ultraviolet light (Stratagene, Los Angeles, Calif.). Hybridization was completed with cDNA probes labeled with $^{32}$P dCTP and the blots were washed under high-stringency conditions (0.2×SSC, 0.1% SDS at 60° C.). Blots were exposed to PhosphorImager screens at 25° C. or to Kodak X-Omat AR film with an intensifying screen at −70° C.

Differential mRNA Display

Differential mRNA display analysis was carried out as described (Liang, P. & Pardee, A. B., 1992, *Science*, 257:967–971; Liang, P., Averboukh, L. & Pardee, A. B., 1993, *Nucl. Acids Res.*, 21:3269–3275, both of which are herein incorporated by reference), except that in vivo rather than in vitro samples were used and six rather than two samples were compared simultaneously, e.g. cDNA from 6 separate RNA populations representing 2 syngeneic hearts (normal on histologic examination) and 4 allografted hearts (with early indications of chronic cardiac rejection). Control studies included the substitution of water for cDNA or the omission of reverse transcriptase in the cDNA synthesis. The cDNA and PCR reactions were modified as follows. Total RNA (0.5 μg) was reverse transcribed in a 50-μl reaction using Superscript reverse transcriptase (Gibco-BRL Life Technologies, Baltimore, Md.) and the degenerate oligo dT primer, $T_{12}$VC or $T_{12}$VA (where V represented a mixture of dG, dA or dC) (Genosys, The Woodlands, Tex.). Control reactions were performed in the absence of reverse transcriptase. The cDNAs were then amplified by PCR in the presence of [$\gamma$-$^{35}$S]dATP on a Perkin Elmer 9600 thermal cycler, and control studies were performed in which water was substituted for CDNA. The reactions (20 μl) included arbitrary 10-mers (Kit A, Operon Technologies, Alameda, Calif.) as 5' primers and $T_{12}$VC or $T_{12}$VA as 3' primers. PCR parameters for the 40-cycle reaction were as follows: denaturation at 94° C. for 15 seconds, annealing at 40° C. for 60 seconds, and extension at 70° C. for 20 seconds. Radiolabeled PCR amplification products were analyzed using electrophoresis. Variability of 5–20% in the number and intensity of bands among given samples on repeated PCR analyses, as well as among different allogeneic or syngeneic samples in the same PCR analysis was observed. To confirm the reproducibility of amplification for selected bands, the reactions were repeated at least three times with different preparations of CDNA. Differentially upregulated bands were defined as those that were consistently present in all four allogeneic samples and absent in both syngeneic samples. Differentially downregulated bands were defined as those present only in syngeneic samples. PCR product bands were recovered from sequencing gels using electroelution and reamplified in a 40-cycle PCR reaction (80 μl) in the absence of isotope. Reamplified cDNAs ranging from 100 to 500 bp were used for cloning into plasmid vectors and as templates for random priming.

Cloning

Reamplified PCR products were directly cloned into the TA cloning vector PCR II (Invitrogen, San Diego, Calif.). The inserts were used as probes in Northern blot analysis of RNA from various cardiac allografts, syngrafts, and host hearts to confirm the allograft-specific hybridization pattern. The partial 3' cDNA fragment was then used to screen ~500,000 plaques from a bacteriophage lambda, custom Uni-ZAP cDNA library prepared from 14-day cardiac allograft poly(A)+RNA (Stratagene). Positive clones were isolated and rescued as plasmids, and their identity was verified by demonstration of allograft-specific hybridization on Northern blot analysis. DNA sequencing of both sense and anti-sense strands was performed with the Sequenase 2.0 kit (United States Biochemical, Cleveland, Ohio) on double-stranded plasmid DNA clones and subclones. Nucleotide and predicted amino acid-sequence searches of the GenBank and EMBL data bases were performed with the (FASTA program GCG software package).

Inflammatory Cell Populations

Isolated splenocytes were obtained by sieving splenic tissue into DMEM medium (Gibco-BRL Life Technologies, Baltimore, Md.) using methods well known in the art. These cells were fractionated with Ficoll-Paque (Pharmacia, Piscataway, N.J.), and the mononuclear fraction was cultured at a density of $2 \times 4 \times 10^6$ cells/ml in a humidified incubator at 37° C. with 5% $CO_2$. A lymphocyte-enriched cell population was obtained by nylon wool purification, where nonadherent cells are removed by gentle washing. Cells adhering to plastic dishes were stained with an anti-macrophage antibody, ED1 (Bioproducts, Inc., Indianapolis, Ind.), with greater than 70% positive indicating an enrichment for phagocytic cells. In contrast, few of the nonadherent cells were ED1 positive.

Where indicated, lipopolysaccharide (1 ng/ml, Sigma, St. Louis, Mo.), rat interferon-γ, (100 U/ml, Gibco-BRL Life Technologies, Baltimore, Md.), concanavalin A (2 µg/ml, Sigma, St. Louis, Mo.) or buffer alone was added to isolated cell populations. The cells were harvested 3 hours later. Peritoneal inflammatory rat macrophages were elicited with thioglycolate medium using standard methods (Steinbeck, M. J., A. U. Khan, and M. J. Karnovsky, 1993, Extracellular production of singlet oxygen by stimulated macrophages quantified using 9,10-diphenylanthracene and perylene in a polystyrene film, *J. Biol. Chem.*, 268:15649–15654). Peritoneal exudate cells were collected 4 days after induction of inflammation, separated on a Ficoll-Paque gradient, and plated at a density of $2 \times 10^6$ cells/ml. At least 90% of the adherent cell population were judged to be macrophages by morphologic criteria and antibody staining. Total RNA was extracted from these isolated cells, the quality of which was assured by evaluation of ribosomal RNA after 1 µg had been separated on 3 mm agarose gels prior to cDNA preparation.

Semiquantitative Reverse-transcription PCR Assay

As an alternative to Northern blot analysis, a semiquantitative, reverse-transcription PCR analysis to compare Gal/GalNAc macrophage lectin transcript levels was performed to allow conservation of RNA when samples were limited. A reverse-transcription PCR technique developed to measure differences in monocyte chemoattractant protein-1 transcript levels (Russell et al.,1993 supra) was modified for use with Gal/GalNAc macrophage lectin. cDNA synthesis was completed with random primers (2.5 µg total RNA per reaction). Oligonucleotides were synthesized by Genosys, The Woodlands, Tex. The sequences were CCT AGA AAC CCT GAG AAC (SEQ ID NO: 31) for the 5' primer and GAG TGC CGC TTA TTG TAG (SEQ ID NO: 32) for the 3' primer, chosen from the sequence analysis of our CDNA clone to result in a 941-bp product. The thermal cycling parameters were denaturation at 94° C. for 15 seconds, annealing 54° C. for 20 seconds, and extension for 60 seconds (with a final extension of 7 minutes at the end of all cycles). For quantitative PCR analyses, 150,000 cpm of $^{32}P$-dCTP was included in the PCR reaction. The products were separated on 1% agarose gels which were dried and exposed to PhosphorImaging screens for 12 hours. The amount of incorporated $^{32}P$ in amplified product bands was then measured by volume integration (Imagequant Software, Molecular Dynamics, San Francisco, Calif.).

To identify the optimum PCR conditions for accurate measurement of gene transcript levels, the linear assay range with respect to cycle number and starting template concentration was established by using different dilutions of cDNA. The measurement of Gal/GalNAc macrophage lectin transcript levels was then completed within these ranges (30 cycles, with starting cDNA dilutions of 1.25 µl). PCR amplification with G3PDH, a ubiquitously expressed gene, was used as a control to assess variations in total RNA or cDNA loading between samples. Corrected Gal/GalNAc macrophage lectin values were derived by dividing the measured amplified product value by the mean of the G3PDH value obtained for that cDNA from at least 3 analyses. PCR analyses were completed on each set of cDNAs at least four times. Results were subjected to multiple analysis of variance (MANOVA) without replication. If a difference was significant, individual comparisons were made by the student's t test, corrected by the Bonferroni method. Although there were variations in absolute values derived from different experiments, relative differences between cDNA sets analyzed at the same time were preserved.

Comparison of Corrected Gal/GalNAc Macrophage Lectin Levels

Differences in corrected Gal/GalNAc macrophage lectin transcript levels were examined in 3 separate studies. The first study was completed to compare differences in transcript levels at various time points after cardiac transplantation. The 10 cDNAs in this time-course study included samples from 4 cardiac allografts harvested 7, 14, 28, and 75 days after transplantation compared with 1 day-0 Lewis heart, a total of 3 paired host hearts from days 7, 14, and 28, and a day-14 Lewis syngraft with its paired host heart. The second cDNA analysis examined whether Gal/GalNAc macrophage lectin induction occurred systemically or locally. cDNA levels in the host spleen (principal source of inflammatory cells) were compared with those in the allografted heart. The 6 cDNAs analyzed were derived from 2 allogeneic cardiac transplants: 1 harvested at 7 days, the other at 28 days. At each time point, the cDNAs from the host heart, allografted heart, and the host spleen were compared. In the third CDNA study, Gal/GalNAc macrophage lectin gene expression in various populations of isolated rat inflammatory cells was examined. Of the 9 cDNAs studied, 6 were prepared from splenocytes (both adherent and nonadherent, each type stimulated with buffer, concanavalin A, and lipopolysaccharide/interferon-γ), 2 from separate thioglycolate-elicited macrophage preparations, and 1 from a 14-day cardiac allograft.

In situ Hybridization

In situ hybridization was completed as described (Arceci, R. J., A. A. J. King, M. C. Simon, S. H. Orkin, and D. B. Wilson, 1993, Mouse GATA-4: a retinoic acid-inducible GATA-binding transcription factor expressed in endodermally derived tissues and heart, *Mol. Cell. Biol.,*

13:2235–2246, herein incorporated by reference), using 5-micron frozen sections obtained from 7-day cardiac allografts and paired host hearts. To generate radiolabeled antisense and sense transcripts, the full-length 1.4-bp Bluescript cDNA was linearized and transcribed with T7 or T3 polymerase using $^{35}$S-UTP. The specificity of the antisense riboprobe was confirmed by hybridization in Northern analysis to 1.4-kb transcripts in lanes with cardiac allograft total RNA, but not in lanes with day-0 heart total RNA.

EXAMPLE 1

Methods of Screening for Differentially Expressed Genes involved in Allograft Rejection For most genes, expression is regulated at the level of transcription. Conventional measurements of mRNA transcript levels are usually confined to selected genes of interest and often require information about the gene sequence. In contrast, PCR-based differential display techniques circumvent this constraint by allowing comparison of gene expression patterns between two cell populations (Liang et al., 1992, supra) or between various murine organs (Welsh, J., Chada, K., Dalal, S. S., Cheng, R., Ralph, D. & McClelland, M., 1992, Nucl. Acids Res., 20:4965–4970). One of the principal advantages of differential display is that it permits the simultaneous identification of genes that are up- as well as downregulated. Thus differential display has the potential to identify a spectrum of molecular factors (known and unknown) that are differentially regulated in cells under various conditions.

Studies of allograft rejection in humans have been restricted by the limited availability of tissue for analysis. Clinical specimens are heterogenous in their degree of chronic rejection, their extent of superimposed disease processes, and the period between the time they are obtained and the time of transplantation. Also, transplanted hearts obtained at autopsy are not suitable for analysis (which requires viable tissue), and the utility of endomyocardial biopsy specimens is limited by their small size. Moreover, the restricted extent of arteriosclerotic lesions that follow transplantation suggests that the process is locally regulated; thus, studies measuring systemic levels of factors implicated in chronic rejection may not accurately reflect levels within the graft (Fyfe, A., Daly, P., Galligan, L., Pirc, L., Feindel, C. & Cardella, C., 1993, J. Am. Coll. Cardiol, 21:171–176).

Differential mRNA Display

To identify transcriptionally regulated genes potentially involved in chronic rejection, differential mRNA display patterns for hearts from syngeneic transplantations were compared with those for hearts from allogeneic transplantations. Syngeneic hearts were normal on histologic examination, whereas 7- and 14-day allogeneic hearts showed luminal monocyte adhesion and infiltration without intimal thickening. PCR amplifications were performed with 27 primer combinations on all six samples and identified twelve PCR products, designated Bands 1–12. These bands were differentially expressed between allogeneic and syngeneic tissue. FIGS. 9A–9C show PCR amplifications obtained with three separate primer combinations. Four representative PCR products (Bands 1, 2, 11, and 12) were identified. These bands were reproducibly present in the allogeneic samples (Lanes 3–6), but not in the syngeneic samples (Lanes 1 and 2), in each of the three analyses identified (see FIGS. 9A–9C).

RNA Blot Analysis with PCR-amplified Fragments

To confirm the gene regulation patterns observed in the differential display study, the twelve bands described above were recovered, reamplified, and used to probe RNA blots prepared with RNAs from syn- and allogeneic transplantations. When used as probes, four of the twelve PCR-amplified fragments (Bands 1, 2, 11, and 12) generated hybridization patterns that reproduced the allograft-specific increase in expression (FIG. 10A, Lanes 3–6). All four of these probes generated two hybridization signals of different sizes. The two signals identified by the Band-1 and -11 probes were both specifically present in allografted tissues (Lanes 3–6, arrows) and absent in syngrafted tissues (Lanes 1 and 2). In contrast, the Band-2 and -12 probes each generated one allograft-specific signal (arrows) reproducing the differential display pattern, as well as a second signal present in all six lanes (arrowheads) that did not reproduce the differential display pattern. Three reamplified PCR fragments hybridized nonspecifically to all six lanes. Five of the twelve cDNA probes did not detect any transcripts (data not shown). Such transcripts may not have been detected because their levels were below the sensitivity of the RNA blot analysis. As a control, RNA loading in all six lanes was confirmed by hybridization with the ribosomal reference gene 36B4 (Laborda et al., supra).

RNA Blot Analysis with Cloned Fragments

The PCR products that generated one or more allograft-specific hybridization patterns were then cloned and used as hybridization probes in RNA blot analysis to identify single clones corresponding to specific mRNA transcripts (FIG. 10B and Table 1). For Bands 2 and 12, individual cDNA clones were identified that produced hybridizations in an allograft-specific fashion. Identification of individual clones was more arduous for the bands that had generated two allograft-specific signals in the initial RNA blot analysis.

Two separate mechanisms account for the transcripts of two sizes observed for Band 1 compared with Band 11. For Band 1, an individual cDNA clone generated two faint hybridization signals of 3.5 kb and 1.5 kb specifically in the allograft samples (Lanes 3–6). This suggests that the two mRNAs were generated by alternative splicing of a common mRNA precursor, by a gene duplication event, or, less likely, by a common regulatory pattern for genes that share some homology. For Band 11, however, two independent cDNA clones with allograft-specific regulation were isolated: one hybridizing to a 1.0-kb transcript and the other to a 3.5-kb transcript. These two distinct clones hybridizing to transcripts of two sizes demonstrate that PCR-amplified products from a display band can contain a number of distinct cDNA fragments derived from different genes (Table 1). Thus, in the initial RNA blot screen, the PCR reamplified fragment (which may contain a mixture of PCR products) is more likely to identify differentially regulated transcripts than are individual CDNA clones.

Sequence Homology

Cloned cDNA fragments that generated allograft-specific hybridization patterns in the RNA blot analysis were sequenced, and preliminary homology searches were performed. The results are summarized in Table 1. The CDNA fragment from Band 2 was found to be highly homologous to rat Gal/GalNAc lectin macrophage. The 382-bp fragment was 98% identical to bases 975–1357 of the published lectin sequence (Ii, M., Kurata, H., Itoh, N., Yamashina, I. & Kawasaki, T., 1990, J. Biol. Chem., 265:11295–11298). This region includes 114 bp of open reading frame as well as 3' untranslated sequences. Homologies with two distinct genes were identified for the two independent clones associated with Band 11. The cDNA fragment (110 bp) that hybridized to the smaller mRNA transcript (1.0 kb) was 79% homologous to the 3' untranslated region of a partial cDNA sequence obtained from a mouse ubiquitin-like gene (Kumar, S., Tomooka, Y. & Noda, M., 1992, Biochem.

Biophys. Res. Commun., 185:1155–1161). The cloned fragment (119 bp) that hybridized to the larger transcript (3.5 kb) was 92% homologous to a partial cDNA sequence of the mouse nuclear P1 gene (Hershko, A. & Ciechanover, A., 1992, Annu. Rev. Biochem., 61:761–807). The homologous region of the P1 gene was located within the open reading frame (bases 1–120) and not at the 3' end. Therefore, in this instance, the 3' primer of the initial PCR reaction hybridized to an internal sequence. To date no significant homology with any published gene for the sequences obtained from the Band-1 and -12 CDNA fragments has been found, suggesting that they represent previously unknown genes associated with chronic cardiac rejection.

Each differential display analysis was performed at least three times to reduce nonspecific (background) PCR signal interference, and the selection of cDNA bands chosen for further study was restricted to those that reproduced the regulation pattern of the first RNA blot analysis in at least three analyses.

Using 27 primer combinations, twelve differential display cDNA bands that were reproducibly up- or downregulated in allogeneic hearts were identified. For four of the twelve bands, this allograft-specific regulation was reproduced on RNA blot analysis. Two unknown genes and three known genes not previously implicated in chronic rejection were identified.

The screening methods of the invention are designed to identify mediators that might be selective for or specific to chronic rejection. Three known genes never before associated with transplant rejection and two novel genes have been identified using the methods of the invention. The three upregulated genes with identifiable homologies correspond to the Gal/GalNAc macrophage lectin, the nuclear P1 gene, and a ubiquitin-like gene.

The link between the macrophage lectin gene and chronic rejection is important because, prior to the invention, the factors responsible for macrophage accumulation in the early phase of the process were not known. Lectins are cell-surface molecules that mediate cell-cell interactions by recognizing specific sugar molecules on adjacent cells (Sharon et al., supra). The murine Gal/GalNAc-specific lectin was originally identified by immunofluorescence on thioglycolate-elicited and OK-432 (a streptococcal antitumor preparation)-activated macrophages but not on unstimulated or resident macrophages (Oda et al., 1989, supra), suggesting that this lectin may be a marker of macrophage activation.

The mouse P1 protein, a homologue of yeast MCM3 (minichromosome mutant), plays a role in the initiation of DNA replication in association with DNA polymerase primase (Thoemmes, P., Fett, R., Schray, B., Burkhart, R., Barnes, M., Kennedy, C., Brown, N. C. & Knippers, R., 1992, Nucl. Acids Res., 20:1069–1074). The identification of elevated transcript levels for the P1 gene in cardiac allografts compared with syngrafts suggests the presence of replicating cells at early points in chronic rejection. Localizing the specific cell type that expresses P1 gene transcripts (or protein) by in situ hybridization or immunohistochemistry may help elucidate early proliferative processes in chronic rejection.

The third known gene upregulated in cardiac allografts is homologous to the 3' region of a murine ubiquitin sequence (Kumar et al., supra). As its name implies, ubiquitin is expressed in all eukaryotic cells. However, ubiquitin gene transcripts appear to be upregulated specifically in allogeneic tissue. Although ubiquitin is involved in a wide variety of regulatory functions within the cell, its role in protein degradation is best understood. In that process ubiquitin is covalently attached to a specific protein target which is then recognized and degraded (Hershko et al., supra). The conjugation of ubiquitin to a protein is essential to normal protein turnover. However, the induction of ubiquitin is also part of the cellular response to stress, damage, or injury (Mayer, R. J., Arnold, J., Laszlo, L., Landon, M. & Lowe, J., 1991, Biochim. Biophys. Acta, 1089:141–151). Although ubiquitin's specific role in chronic cardiac rejection is not clear, it is possible that ubiquitin is involved in the response to immune injury thought to initiate allograft arteriosclerosis.

Advantages

The screening methods of the invention can be used to identify mediators associated with chronic allograft rejection, a complex, multicellular disease process using differential display technology to detect upregulated or downregulated allograft gene transcripts. Differential display technology has been used to study breast cancer (Liang et al., 1992, supra; Liang et al., 1993, supra; Liang, P., Averboukh, L., Keyomarsi, K., Sager, R. & Pardee, A. B., 1992, Cancer Res., 52:6966–6968; Sager, R., Anisowicz, A., Neveu, M., Liang, P. & Sotiropoulou, G., 1993, FASEB J., 7:964–970). However, in contrast to the breast-cancer studies, which compared two populations of in vitro cell lines at once, the screening methods of the invention compare whole tissue from allogeneic transplantations (where chronic rejection develops) with whole tissue from syngeneic transplantations (where rejection is absent). One important advantage of this approach is that the pathophysiologic environment associated with the chronic disease process is preserved. The invention provides a method of analyzing a mixture of both resident and infiltrating cells, as well as the complex network of regulatory stimuli that may have been impossible to reproduce in isolated cells in vitro (Liaw, L. & Schwartz, S. M., 1993, Arterioscler. Thromb., 13:985–993). Also, because the screening method can compare a number of tissue samples at once, e.g., a series of six transplanted hearts simultaneously, the identification of factors that might be related to a single animal or procedure rather than to the disease itself can be avoided.

With the identification of these five candidate mediators of chronic rejection, utility of the screening methods of the invention, e.g., those which utilize differential mRNA display analysis, to identify molecular factors associated with complex multicellular processes, has been demonstrated. For identification of allograft-specific factors, an increase or decrease in allograft gene transcript of at least 4 times the amount of corresponding syngraft gene transcript is preferable.

In the case of chronic rejection, which affects the donor organ only and spares host organs, differential mRNA display can be used to examine the transplanted heart as well as its infiltrating cell populations. Given that inflammatory cells are often activated in a manner specific to their microenvironment, the power of this technique resides in its preservation of infiltrating cells and the complex network of regulatory influences in the tissue under investigation. In vitro systems investigating single cell types cannot reproduce the spectrum of interactions present in diseased tissue in vivo because they lack the counterregulatory effects of neighboring cells. The differentially regulated factors identified in this manner are therefore more likely to be of direct clinical relevance. Finally, the methods of the invention allow the identification of candidate factors that may be beyond the scope of established theories of chronic rejection.

EXAMPLE 2
Assays to Diagnose Rejection of an Allograft

As described above, several genes (Gal/GalNAc-macrophage lectin, AIF-1, AIF-2, ubiquitin and P1) which are differentially expressed in the allograft have been identified using the screening methods of the invention. Other genes can be identified using the same methods. Having identified genes which are differentially expressed in an allograft compared to a syngraft, detection of expression of these genes either at the level of transcription, e.g, by PCR, Northern blot, differential mRNA display, or in situ hybridization, or at the level of translation/protein production, e.g., by FACS, Western blot, or in situ immunostaining, provides a valuable tool for early and reliable diagnosis of transplant rejection. For example, Gal/GalNAc macrophage lectin transcript or protein levels in transplanted heart samples obtained by endomyocardial biopsy could serve as clinical markers of macrophage infiltration. These levels might provide prognostic information about the degree of chronic rejection or the rate at which arteriosclerosis is progressing.

One of the major advantages of such a diagnostic approach is that the screening methods of the invention allow early detection of events which lead to allograft rejection, and thus facilitate early intervention to prevent or inhibit rejection of the transplanted organ. Another advantage is that the diagnostic methods of the invention can be performed on a very small amount of tissue which may be obtained using standard biopsy techniques known in the art.

EXAMPLE 3
Therapeutic Applications for Differentially Expressed Allograft Genes As described above, an increase in the amount of an allograft gene transcript compared to the corresponding syngraft gene transcript indicates that the allograft transcript encodes a mediator of allograft rejection. Thus, allograft rejection in patients may be decreased or inhibited using gene therapy in which a portion of the antisense strand of the upregulated gene is introduced into the cells in which the gene is transcribed. The antisense oligonucleotide (either RNA or DNA) may be directly introduced into the cells in a form that is capable of binding to the transcripts. Alternatively, a vector containing sequence which, once within the target cells, is transcribed into the appropriate antisense mRNA, may be the species administered to the patient's cells. An antisense nucleic acid which hybridizes to the mRNA of the target gene can decrease or inhibit production of the polypeptide product encoded by the gene, by forming a double-stranded segment on the normally single-stranded mRNA transcript, and thereby interfering with translation.

A DNA which is expressed as a transcript antisense to a portion of the target gene may be operably linked to appropriate expression control sequences and introduced into target cells of the patient by standard vectors and/or gene delivery systems. Suitable gene delivery systems may include liposomes, receptor-mediated delivery systems, naked DNA, and viral vectors such as herpes viruses, retroviruses, and adenoviruses, among others.

A therapeutic composition is provided which includes a pharmaceutically acceptable carrier and a therapeutically effective amount of a nucleic acid which is capable of inhibiting translation of the target mRNA, either directly or by being transcribed into an antisense transcript which inhibits translation. The therapeutic composition may also include a gene delivery system as described above. Pharmaceutically acceptable carriers are biologically compatible vehicles which are suitable for administration to an animal: e.g., physiological saline. A therapeutically effective amount is an amount of the DNA of the invention which is capable of producing a medically desirable result in a treated animal, e.g., downregulation of the differentially expressed allograft gene.

As an alternative to the antisense-based therapy described above, one could employ polyclonal or monoclonal antibodies specific for the polypeptide product of the overexpressed allograft polypeptide, in order to block that polypeptide's activity in vivo. Similarly, one could employ polypeptide inhibitors to block activity of the differentially expressed allograft polypeptide, e.g., fragments of the polypeptide which block binding of the polypeptide to its ligand. The antibody or other polypeptide-based therapeutic can be delivered by standard means, such as intravenous injection.

As is well known in the medical arts, dosages for any one patient depends upon many factors, including the patient's size, body surface area, age, the particular compound to be administered, sex, time and route of administration, general health, and other drugs being administered concurrently. Dosages for the compounds of the invention will vary, but a preferred dosage for intravenous administration is from approximately $10^6$ to $10^{22}$ copies of the nucleic acid molecule.

EXAMPLE 4
Rat AIF-1

As described above, the differential display screening methods of the invention were used to identify two novel genes which are upregulated in rat cardiac allografts with transplant arteriosclerosis. Bands 1 and 12 (see FIGS. 9A–9C) were harvested, reamplified, and used as probes in Northern analysis. The allograft-specific induction pattern was confirmed in the RNA extracted from the original 6 samples, identifying gene transcripts of 0.7 kb. Following Northern blot confirmation, partial cloning, sequence analysis of AIF-1 (331 bp sequenced/400 bp fragment) (SEQ ID NO:1), and a homology search were completed. Partial cloning, sequence analysis, and a homology search were also completed for AIF-2 (359 bp/~450 bp sequenced) (SEQ ID NO:2, 3). A database search using these fragments revealed no alignment with known sequences.

Cloning and Characterization of Full-length AIF-1 cDNA

A custom-made rat cardiac allograft cDNA library was obtained from Stratagene, Inc. To isolate the full-length cDNAs, the 14-day old cardiac allograft cDNA library was screened with the partial cDNA fragments identified in the differential display. Fifteen AIF-positive phagemid clones were obtained; however, eight were identical in sequence. The full-length cDNA of AIF-1 (SEQ ID NO:4) is 627 bp long and contains a 70-bp 5' untranslated region, a continuous open reading frame of 441 bp, and a 116-bp 3' untranslated region that includes one potential polyadenylation sequence. Translation of the open-reading frame predicts a polypeptide of 147 amino acids, with a calculated molecular mass of 16.8 kD. Charged amino acids comprise 35% of the predicted polypeptide. The profile generated by the Kyte-Doolittle algorithm (FIG. 11) predicts a hydrophilic polypeptide without significant hydrophobic stretches, which are usually associated with membrane-spanning proteins.

Database searches revealed homology with genomic sequences obtained from a 90-kb segment of the human HLA class III region (which had been systematically sequenced in a mapping effort) (Iris et al., Nature Genet. 3:137–145, 1993). Homology ranged from 68–93% over the entire AIF-1 cDNA sequence. Alignment was identified in a segment 7 kb upstream of the BAT-2 gene. To date, no coding sequences have been submitted to the GenBank and EMBL data bases in this region; thus, AIF-1 appears to represent a novel cDNA. Motif analysis of the predicted amino acid sequence identified a potential EF-hand domain that is characteristic of an evolutionary family of calcium-binding proteins (Strynadka et al., Ann. Rev. Biochem. 58:951–998, 1989). Typically, the conserved amino acids within the loop are involved in binding of the calcium ion. AIF-1 matches the consensus sequence of the EF-hand loop supplied through the Prosite data base (release 9.2), with the exception of position 12. This conserved position-12 residue (usually glutamic acid or aspartic acid) is replaced by a serine residue in the AIF-1 sequence. In addition to the conserved loop sequence, AIF-1 has some alignment within the entire EF-hand region to other members of the family, such as mouse troponin C (51% similar or identical amino acids) (Pamacek et al., J. Biol. Chem. 265:15970–15976, 1990) and human calmodulin (48% similar or identical amino acids) (Koller et al., Biochim. Biophys. Acta. 1163:1–9, 1993).

Northern and Genomic Southern Analysis

Total RNA was isolated with RNAzol B (Tel-Test, Inc., Friendswood, Tex.). Northern blots were prepared with 20 μg of total RNA as described above. Genomic DNA was isolated and digested with the indicated restriction endonucleases, electrophoresed through 0.8% agarose gels, and transferred to nitrocellulose (Micron Separations, Westboro, Mass.) by capillary transfer as described (Russell et al., Blood 72:1833–1836, 1988). Hybridization with cDNA probes labeled with $^{32}$p dCTP by random priming (Boehringer-Mannheim, Indianapolis, Ind.), and high-stringency washes (0.2×SSC, 0.1% SDS at 60° C.), were performed as described above. The AIF-1 cDNA hybridized to genomic DNA from rats, mice, and humans (FIG. 12), demonstrating evolutionary conservation across these species. The presence of only one or two bands under high-stringency conditions suggests that AIF-1 is encoded by a single-copy gene.

Semiquantitative Reverse-transcriptase PCR Assay

The reverse-transcriptase PCR technique described above was used to measure AIF-1 transcript levels. cDNA synthesis was completed with random primers (2.5 μg of total RNA per reaction). Oligonucleotides were synthesized by Genosys Biotechnologies (The Woodlands, Tex.). To amplify rat cDNAs, the following primers were used: 5' primer GTCAATTCGCTATGAGCCAGAGCAAG (SEQ ID NO: 33) and 3' primer GAAGAAGCAGTTGTGAGCGTCGACCAA, (SEQ ID NO: 34), a combination that resulted in a 543-bp product. For murine and human cDNAs, an internal set of primers were used: 5' ATCCCAAGTACAGCAGTGATGAGG (SEQ ID NO: 35) and 3' GTCCCCCAGCCAAGAAAGC-TATTT (SEQ ID NO: 36), which generated a 329-bp PCR product. Reaction conditions were as described above. The thermal cycling parameters were denaturation at 94° C. for 15 sec, annealing at 56° C. for 20 sec, and extension for 60 sec (with a final extension of 7 min at the end of all cycles). For quantitative PCR analyses, 150,000 cpm of $^{32}$P-dCTP were included in the PCR reaction. The products were separated on 1% agarose gels which were dried and exposed to PhosphorImaging screens for 24 h, and the amount of $^{32}$P incorporated in the amplified product bands was measured by volume integration (Imagequant software, Molecular Dynamics, Sunnyvale, Calif.).

To identify the optimal PCR conditions for accurate measurement of gene transcript levels, linear assay ranges were established with respect to cycle number and starting template concentration for various dilutions of cDNA. Measurement of AIF-1 transcript levels was then completed within these ranges (23 cycles and cDNA dilutions of 1.25 μl for both primer combinations). PCR analyses were completed on each set of cDNAs at least 3 times. PCR amplification with G3PDH, a ubiquitously expressed gene, was used as a control to assess variations in total RNA or cDNA loading between samples. Corrected AIF-1 values were derived by dividing the measured amplified product value by the mean of the G3PDH value obtained for that cDNA from at least 3 analyses. Results were subjected to multivariate analysis of variance without replication. If a difference was significant, individual comparisons were corrected by the Bonferroni method. Although there were variations in absolute values derived from different experiments, relative differences between cDNA sets analyzed at the same time were preserved.

In situ Hybridization

In situ hybridization was completed as described above, using 5-micron frozen sections obtained from 28-day cardiac allografts and paired host hearts and spleens. To generate radiolabeled antisense and sense transcripts, the full-length AIF-1 cDNA was linearized and transcribed with T7 or T3 polymerase in the presence of $^{35}$S-UTP. The specificity of the riboprobes was confirmed by hybridization of the antisense probe in Northern analysis to 0.7-kb transcripts in lanes with cardiac allograft total RNA but not in lanes with day-0 heart total RNA, and by no hybridization with the sense probe.

Protein Expression Studies

Recombinant AIF-1 was generated as a fusion protein using the pMAL-c2 (New England Biolabs, Beverly, Mass.) or the pFLAG-1 (International Biotechnologies Incorporated, New Haven, Conn.) expression vector according to the manufacturers' instructions. The purified protein was used as an immunogen to generate a polyclonal rabbit antiserum (East Acres Biologicals, Southbridge, Mass.). Tissue or cellular extracts were prepared by homogenization in 50 mM Tris (pH 8.0), 500 mM NaCl, 20% glycerol, 1 mM dithiothreitol, and 0.5 mM phenylmethanesulfonyl fluoride. Protein extracts (25 μg) were separated on 15% SDS polyacrylamide gels and transferred to polyvinylidene difluoride membranes (Millipore, Bedford, Mass.). Immunostaining was performed with an enhanced chemoluminescence detection kit (ECL, Amersham, Cleveland, Ohio) according to the manufacturer's directions, at primary antiserum dilutions of 1:3000. Negative controls included omission of the primary antibody or use of preimmune serum. Immunohistochemical staining of frozen sections from 28-day cardiac allografts, host hearts, and spleens was completed at an antiserum dilution of 1:500 (1 h, 25° C.) as described (Russell et al., J. Clin. Invest. 94:722–730, 1994). Negative controls included omission of the primary antiserum, use of preimmune serum, and use of an irrelevant primary antiserum.

In vitro and In vivo Regulation of AIF-1 Transcript Levels

In vitro stimulation studies of various macrophage cells or cell lines were completed using rat IFN-g (100 units/ml) (Gibco-BRL, Gaithersburg, Md.), phorbol 12-myristate-13-acetate (50 ng/ml) (Sigma), or lipopolysaccharide (*E. coli* serotype 0111:B4) (100 ng/ml) (Sigma, St. Louis, Mo.). To study whether strategies which impair T-cell activation in vivo would alter AIF-1 transcript levels, cDNA samples from two series of transplants performed previously were evaluated. In the first series, the cDNAs were prepared from transplanted and host hearts harvested at day 7 and 28 from recipients fed an anti-inflammatory, essential fatty aciddeficient (EFAD) diet or a control diet. In the second transplant series, the recombinant fusion protein CTLA-4 Ig (Bristol-Myers Squibb, Seattle, Wash.), which blocks the CD28/B7 costimulatory pathway, was used to inhibit T-cell activation in chronic cardiac rejection (Sayegh et al., J. Am. Soc. Nephrol. 5:989, 1994). These cDNA samples were prepared from 75-day cardiac allografts treated with (a) a single dose of CTLA-4 Ig (0.5 mg intraperitoneally) (n=3), (b) a single dose of CTLA-4 Ig and an intravenous injection of donor splenocytes cells (n=3), or (c) a single dose of cyclosporine_A (5 mg/kg intramuscularly) (Sandoz, Basel) (n=3). These samples were compared with samples from day-75 syngrafts (n=3) and an untreated (reference) day-75 cardiac allograft (n=1).

Northern Blot Analysis of Rat Organs

Northern blot analysis (FIG. 13) showed strong hybridization of the AIF-1 cDNA to 0.7-kb transcripts in total RNA from a day-28 cardiac allograft, spleen, and testis. The increase in AIF-1 transcripts in this cardiac allograft compared with a control heart (day 0), which had been harvested but not transplanted, confirms the allograft-specific pattern identified above. The presence of AIF-1 transcripts in the spleen (a major source of inflammatory cells) as well as the cardiac allograft—the vessels of which are characterized at day 28 by mononuclear cell infiltration and early intimal thickening—suggests that AIF-1 represents an inflammatory cell transcript.

AIF-1 Gene Expression Increases in Cardiac Allografts Over Time

To study AIF-1 gene expression patterns after cardiac transplantation, transcript levels were measured with a reverse-transcriptase PCR assay in cDNAs derived from cardiac allografts and paired host hearts harvested at various stages of chronic rejection. As seen in the representative analysis that included two transplants from each time point (FIG. 14), AIF-1 transcript levels were significantly higher in cardiac allografts (days 7, 28, 75), in comparison with paired host hearts which had been exposed to the same circulation but had no histologic abnormalities (p<0.003). Transcript levels were also significantly higher in day-75 cardiac allografts (n=2) compared with day-75 cardiac syngrafts (n=2) (p<0.0001). AIF-1 transcript expression peaked at day 28, with cardiac allograft levels significantly higher in comparison with those at both days 7 and 75 (p<0.001) in 2 separate experimental sets. These findings confirm the allograft-specific and time-dependent expression of AIF-1 transcripts originally observed in Northern blot studies in which the AIF-1 3' cDNA fragment was used as probe.

In situ Localization of AIF-1 mRNA to Inflammatory Infiltrates within Cardiac Allografts In FIG. 15A, silver grains indicating hybridization of the AIF-1 antisense riboprobe cluster over regions of inflammatory cell infiltrates in cardiac allograft sections, and they do not cluster over myocytes. Positive hybridization was seen predominately in the interstitium and perivascular spaces. In splenic tissue, silver grains associated with AIF-1 mRNA were identified primarily in regions within the red pulp (not shown). There was no significant hybridization to host hearts (not shown) or when the sense probe was used (FIG. 15B).

AIF-1 Transcript Levels in Inflammatory Cell Populations

To further characterize the cell type(s) that express AIF-1 transcripts, a series of isolated rat cell populations were analyzed by Northern blotting (FIG. 16). AIF-1 transcripts were expressed by bone marrow-derived macrophages, BCG-elicited peritoneal macrophages, and casein-elicited peritoneal neutrophils but not significantly by nylon wool-purified lymphocytes, arctic smooth muscle cells, or bone marrow stem cells. In other studies, AIF-1 transcripts were detected in thioglycolate-elicited peritoneal macrophages and adherent splenocytes. By the reverse-transcriptase PCR assay, AIF-1 transcripts were also present at low levels in a variety of unstimulated murine and human myeloid cell lines, including J744A.1, RAW264.7, P388D.1, HL60, U937, and THP-1. Transcripts were not detected in lymphocytic leukemia cell lines (Jurkat or MOLT-4). Thus, AIF-1 appears to be expressed predominately by cells of the myeloid lineage (monocytes/macrophages and neutrophils).

Immunoblotting with Anti-AIF-1 Serum

A single band of approximately 17 kD was detected with polyclonal rabbit anti-AIF-1 serum in extracts from cardiac allografts, splenic tissue, and bone marrow-derived macrophages propagated in vitro (FIG. 17). The absence of staining in host hearts, lymphocytes, and bone marrow cells reproduced the patterns shown for gene transcripts.

Immunohistochemical Localization of AIF-1 Antigen in Cardiac Allografts

Immunostaining identified a subset of positively labeled mononuclear cells within cardiac allografts (FIG. 18A). The positive cells showed a cytoplasmic staining pattern and were found in regions of perivascular and interstitial infiltration. Besides these inflammatory mononuclear cells, none of the parenchymal cell types within the cardiac allograft stained positive. In splenic tissue, scattered positive cells were identified predominately in the red pulp (FIG. 18B). There was also a rim of positive cells just adjacent to the white pulp. No significant staining was seen when the primary antibody was omitted or when preimmune serum was used.

In vitro Upregulation of AIF-1 Transcripts in IFN-g-treated Macrophages

Expression of the T-cell-derived cytokine IFN-g is persistently upregulated in chronically rejecting cardiac allografts. To examine whether IFN-g is involved in the regulation of AIF-1 expression, in vitro stimulation studies were performed with various rodent macrophage-like cell lines or isolated macrophage populations. In these studies IFN-g stimulation increased AIF-1 mRNA expression in mouse J774A.1, RAW264.7, and P388D.1 cell lines, as well as in rat bone marrow-derived macrophages. The basal level of AIF-1 expression varied among the cell populations, as did the peak expression level in response to IFN-g stimulation (3–6-fold). In a representative study of J774A.1 cells (FIG. 19A), AIF-1 transcript levels increased significantly (5-fold) 24 h after stimulation with IFN-g, in comparison with cells stimulated with phorbol 12-myristate-13-acetate, LPS, or a combination of IFN-g and LPS (p<0.0001). AIF-1 transcript levels did not change significantly at 4 and 10 h with any of the stimulants studied. A more detailed time-course study of the IFN-g response showed that the increase in AIF-1 transcripts was delayed, peaking in J774A.1 cells at 36 h after stimulation (FIG. 19B). The most effective dose of IFN-g was 100 units per ml of medium (FIG. 19C). This late increase in AIF-1 gene expression suggests that its upregulation by IFN-g may be an indirect effect.

In vivo Modulation of T-cell Activation Reduces AIF-1 Transcripts in Cardiac Allografts To study the regulation of AIF-1 expression in vivo, strategies that attenuate T-cell activation and reduce IFN-g expression were utilized. Modulation of the inflammatory response with an EFAD diet decreases expression of IFN-g at day 28, reduces mononuclear cell infiltration, and attenuates arteriosclerotic development in Lewis to F344 cardiac allografts. AIF-1 transcript levels in 28-day cardiac allografts from recipients on the EFAD diet were reduced significantly in comparison with those in allografts from recipients fed a control diet (p<0.0001) (FIG. 10A). In contrast, at day 7 (before the EFAD diet has any effect), there was no significant difference in AIF-1 transcript levels in allografts on the EFAD diet versus the control diet. AIF-1 transcript levels in host hearts were uniformly low.

In addition, blocking the CD28/B7 costimulatory pathway of T-cell activation with CTLA-4 Ig appears to prolong allograft survival and prevent T-cell and macrophage activation in the Lewis to F344 rat model Sayegh et al., supra. AIF-1 transcript levels were reduced significantly in cardiac allografts from recipients treated with CTLA-4 Ig, in comparison with untreated allografts or cyclosporine A-treated (single dose on day 2) allografts (p<0.0001) (FIG. 10B). The most dramatic decrease was seen in the group that received CTLA-4 Ig in addition to donor cells on the day of engraftment. AIF-1 transcript levels in this group were significantly lower than those in cardiac allografts that received CTLA-4 Ig alone (p<0.0001), and similar to those seen in control syngrafts. Taken together, these observations suggest that AIF-1 levels in cardiac allografts are regulated directly by T-cell activation or by cytokines secreted after activation, as suggested by the in vitro data showing that the T-cell-derived cytokine IFN-g upregulated AIF-1 expression.

EXAMPLE 5
Human AIF-1

Human AIF-1 cDNA was cloned and characterized as described below.

Materials and Methods.

Human endomyocardial specimens for RT-PCR analysis were obtained from heart transplant recipients in conjunction with those obtained for routine surveillance. All tissues were harvested after obtaining informed consent under a protocol approved by the subcommittee on human studies. Routine histologic assessment completed by the staff pathologists using the International Society for Heart Transplantation (ISHT) criteria showed that all four specimens had no evidence of rejection (ISHT grade 0/4). Endomyocardial samples were quick frozen in liquid nitrogen and stored at −70 C. until RNA extraction was performed.

Human inflammatory and hepatoma cell lines were obtained from the ATCC and cultured according to their recommendations. Human umbilical vein endothelial cells and umbilical artery smooth muscle cells were obtained from Cell Systems (Kirkland, Wash.), and cultured according to their recommendations. Human interferon gamma (Promega)(100 u/ml) was added to the cell cultures for 24 hours prior to harvest. Human heart tissue was obtained from the explanted heart at the time of transplantation.

Total RNA was isolated from tissue samples or cells maintained in tissue culture using RNAzol B (Teltest, Inc. Friendswood, Tex.). The quality of the total RNA was evaluated by electrophoresis through denaturing agarose gels. cDNA synthesis was completed with random primers (Gibco-BRL, Gaithersburg, Md.) as recommended by the manufacturer. The success of the cDNA synthesis was evaluated by amplification of a reference gene, β-2-microglobulin (B2M) (forward primer: 5-CTC GCG CTA CTC TCT CTT TCT GG (SEQ ID NO: 37) and backward primer: 5'-TTA AGT GGG ATC GAG ACA TGT AAG C (SEQ ID NO: 38)) (Clontech, Palo Alto). In the initial PCR amplification of AIF-1 transcripts from human endomyocardial biopsies, primers selected from the coding region of the rat cDNA (Accession number U179179) were used (forward primer: 5'ATC CCA AGT ACA GCA GTG ATG AGG (SEQ ID NO: 35) and backward primer 5'GTC CCC CAG CCA AGA AAG CTA TTT (SEQ ID NO: 36)) to amplify a predicted 329 bp PCR product. Amplification was completed for 32 cycles with these primers. PCR reagents and reaction conditions were as described above. In brief, parameters included denaturation at 94° C. for 15 sec, annealing at 56° C. for 20 sec, and extension for 60 sec (with a final extension of 7 min). PCR products were separated on agarose gels. For Southern analysis, PCR products were denatured and transferred to nitrocellulose by standard capillary transfer techniques. The blots were hybridized with oligonucleotides from a sequence specific to human AIF-1 nested between the region defined by the primers used for PCR (5'-TGA GAA AGT CAG GGT AGC T; SEQ ID NO: 39). The oligonucleotide was $^{32}p$ end-labeled using T4 polynucleotide kinase (Promega, Madison, Wis.). The blot was washed with 3×SSC, 0.1% SDS and 0.05% sodium pyrophosphate at 42° C., and exposed to Kodak X-omat AR film.

The initial characterization of the rat AIF-1 cDNA revealed alignment with genomic sequences within the human HLA class III region termed BAT-2, as described above. Given that the preliminary screen completed with primers from the rat sequence showed that AIF-12 transcripts were present in human biopsies, primers corresponding to these HLA class III sequences were selected. This permitted the specific amplification of the human AIF-1 cDNA coding region. In subsequent PCR analyses, primers specific for human AIF-1 cDNA were employed (forward primer 5'-ACC TCT ACC AGC ATC TGC (SEQ ID NO: 40) and backward primer 5'-TGA AGG GAA AAG GGA TGA TGG (SEQ ID NO: 41)), resulting in a 489 bp product. Amplification was performed for 29 cycles.

The PCR products amplified from cDNAs obtained from THP-1 cells and two of the human endomyocardial biopsies were cloned directly into the TA cloning vector (Invitrogen) and sequenced (United Stated Biochemicals). Sequence alignments were performed using the McVector and the GCG software package.

Human heart allografts were obtained as previously described (Lin et al., J. Heart Lung Transplant. 13:824–833, 1994). In brief, human allografts were collected as soon as possible after explant or autopsy, immersed in RPMI 1640, rinsed in PBS, and weighed. Ventricular sections were taken immediately and frozen in OCT. Serial cyrostat sections (4 μM) were stained, employing a Ventana automated immunostainer (Ventana Inc., Palo Alto, Calif. Protein A-purified polyclonal rabbit anti-sera against rat AIF-1 (1:100 dilution) was employed as the primary antibody. To identify macrophages, MAb KP1 (Dako Incorporated) directed against CD68 was employed. The primary antibody was omitted in the negative control sample.

Results

In order to determine whether AIF-1 gene transcripts were present in endomyocardial biopsies from human cardiac allografts, RT-PCR amplification was performed using primers derived from rat AIF-1. As shown in FIG. 21A, AIF-1 gene transcripts from cDNAs obtained from four separate patients (lane 3–6) as well as the control day 28 rat cardiac allograft (lane 2) were amplified. FIG. 21B shows amplified products using beta 2-microglobulin as a reference gene for the human samples. There was concordance in the intensities for AIF-1 and B2M PCR products, suggesting that the variability reflects differences in the RNA or cDNA loading the reactions. The identity of these PCR fragments was confirmed by Southern analysis (FIG. 21C). Intense hybridization is seen using a $^{32}P$-oligonucleotide probe corresponding to sequences internal or nested between the original primers. Similar findings were obtained in analysis of an additional six biopsies. These findings confirm the presence of AIF-1 transcripts in human as well as rat cardiac allografts.

In order to clone the human AIF-1 cDNA, PCR primers from the HLA class III genomic region were designed to amplify the fragment corresponding to the rat open reading frame. PCR amplification using cDNAs from human myeloid cell lines THP-1, U937, and HL-60 revealed single bands corresponding to 489 bp. Sequence analysis showed 86% identity between the rat and human fragments at the nucleotide level. Comparison of the deduced amino acid sequences within the coding region (FIG. 22; SEQ ID NOs: 5 and 42) revealed 90% identity and 95% similarity between the human and rat. The identity was confirmed between the available sequences for U937, THP-1, and two human biopsies. Furthermore, the human AIF-1 cDNA aligns with genomic sequences in the HLA Class III region. Nucleotide and predicted amino acid sequence searches of the GenBank (release 85.0) and EMBL (release 36.0) data bases showed no alignment with any reported coding sequences.

Figure 23D:
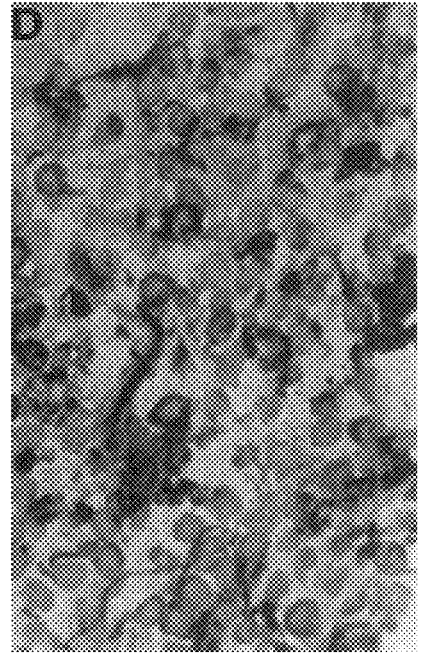

Immunostaining confirmed the presence of the AIF-1 gene product in human cardiac allografts. AIF-1 positive cells were identified in all of the frozen sections from the four transplant patients examined. The AIF-1 antigen localized exclusively to mononuclear cells (typically in clusters) found in the interstitium and perivascular space, as seen in the representative low power (FIG. 23A) and high power (FIG. 23B) sections. The AIF-1 positive cells are most likely macrophages, given that in seriate sections they localize to regions rich in macrophages identified using the human macrophage marker KP-1 (directed against CD68) (FIGS. 23C and 23D). Similar to the rat immunocytochemical studies discussed above, the anti-AIF-1 anti-serum produces a cytoplasmic staining pattern in human mononuclear cells. Interestingly, the AIF-1-positive cells represent only some of the infiltrating macrophage population in the transplanted heart, suggesting that this subset represents a distinct population, perhaps activated or differentiated by local factors.

Human AIF-1 gene expression patterns in various cell types were evaluated using RT-PCR assay to compare relative AIF-1 gene transcript levels. Amplification of the control gene ($\beta_2$M) was successful in all cases (lower panels of FIGS. 24A and B). As seen in the representative gel in FIG. 24A, AIF-1 transcripts are present solely in the cDNA derived from human macrophage-like cell lines (THP-1 (lane 1), U937 (lane 2) and HL-60 (lane 3)). T-cell lines MOLT-4 (lane 4) and Jurket (lane 5), HepG2 (lane 6), human umbilical vein endothelial cells (HUVEC; lane 7), and human umbilical artery smooth muscle cells (HSCM; lane 8). AIF-1 transcripts were also amplified to variable degrees in six endomyocardial biopsies from human cardiac allografts (FIG. 24B).

EXAMPLE 6

Rat AIF-2

As stated above, the differential display screening method of the invention identified a second novel gene, designated AIF-2. The 2.2-kb cDNA fragment of AIF-2 identified up to 3 transcripts (1.5 bp, 3.5 bp, >8.0 kb) in various rat cardiac allografts (day 7, 14, 28) and spleens (but not in the other 8 organs examined). Gene transcript levels measured by reverse transcription PCR indicated that AIF-2 was found in inflammatory cells enriched in macrophages (adherent splenocytes, peritoneal macrophages, a rat pulmonary alveolar macrophage cell line, and bone-marrow macrophages). Preliminary studies indicated that transcript levels in bone-marrow macrophages increased after stimulation with interferon-gamma (IFN-γ) alone or with the combination of IFN-γ and lipopolysaccharide (LPS).

The full-length AIF-1 cDNA (SEQ ID NO:4) was found to be 627 bp in length and contain a 70-bp 5' untranslated region, a continuous open reading frame (longest open reading frame 441 bp), and a 140-bp 3' untranslated region that included one potential polyadenylation sequence. The first ATG was located at base 71. Translation of the open reading frame predicted a 147-amino acid polypeptide with a predicted molecular mass of 16.8 kDa. Charged amino acids comprised 35% of the predicted polypeptide without any cysteines. A hydrophilic profile was predicted from the plot generated using the Kyte and Doolittle algorithm. This plot revealed the absence of any hydrophobic stretches, suggesting that AIF-1 is not a membrane-spanning protein.

Only partial cDNAs derived from the 3' end of the gene have been obtained for AIF-2 (see SEQ ID NOs:2,3,8–27). The remaining 5' sequences can be obtained with further screening of the cardiac allograft library, using known methods employing probes derived from the previously cloned and sequenced 3' fragments. In addition to further screening of the library, PCR amplification of 5' cDNA ends can be accomplished using 5'-RACE (Rapid Amplification of cDNA ends)-Ready™ cDNA and the 5' AmpliFINDER™ RACE Kit from Clontech, Inc. Using this cloning strategy, random hexamers are used for cDNA synthesis, followed by ligation of a modified single-stranded anchor oligonucleotide to the 3' end of the first-strand cDNA. Nested AIF-2 primers derived from the 3' end of the gene and a 5' primer complementary to the anchor can then be used to progressively amplify the remaining 5' end of the gene.

Clinical Applications

As described above, measurements of gene transcript or polypeptide product levels may serve as clinical or diagnostic indicators of macrophage infiltration, chronic inflammation, transplant rejection, and other forms of arteriosclerosis such as atherosclerosis. AIF-1 may be used to identify subsets of macrophages, given that in situ hybridization and immunohistochemical studies show that AIF-1 is expressed by only some of the macrophages in the cardiac allograft and in human atherosclerotic plaques. All or part of the DNAs of the invention, e.g., AIF-1 DNA with the sequence of SEQ ID NO: 1 or 4 or the AIF-2 DNA with the sequence of SEQ ID NO:2, 3, 8, 9, 10, 11, 12, 13, 14, 15, 16, 17, 18, 19, 20, 21, 22, 23, 24, 25, 26, or 27, can be used as hybridization probes to identify AIF-1 or AIF-2, respectively, for the purpose of diagnosing transplant rejection. Portions of these DNAs can also be used as PCR primers to amplify AIF-1 or AIF-2 sequences to identify expression of these genes in allografts for the purpose of diagnosing rejection. The DNA of SEQ ID NO: 1 or 4 can also be used as a reliable transcriptional marker for macrophages.

Administration of AIF-1 or AIF-2 polypeptides or antibodies which bind to either AIF-1 or AIF-2 may modulate the inflammatory response by blocking cell infiltration, migration, activation, or macrophage effector functions. Macrophages have a broad number of effector functions (antigen presentation, parasitic and viral killing, phagocytosis, tumor clearance) which could be impaired by blocking AIF-1 or AIF-2. All or part of the DNAs of the invention, e.g., AIF-1 DNA with the sequence of SEQ ID NO: 1 or 4 or the AIF-2 DNA with the sequence of SEQ ID NO:2, 3, 8, 9, 10, 11, 12, 13, 14, 15, 16, 17, 18, 19, 20, 21, 22, 23, 24, 25, 26, or 27, can be cloned into an expression vector and used to produce polypeptides of AIF-1 or AIF-2 for the purpose of immunizing animals to generate polyclonal or monoclonal antibodies. Such antibodies can then be use for therapeutic applications as described above or for diagnostic applications such as identification of AIF-1 or AIF-2 polypeptides in allografts indicating ongoing transplant rejection.

Also, fusion proteins of AIF-1 or AIF-2 containing components known to block specific inflammatory factors (see Other Embodiments) may also serve as a way of modulating the inflammatory response.

In addition to these therapeutic applications, valuable animal models to study allograft rejection can be made by producing transgenic animals (e.g., mice, rats, rabbits, guinea pigs, hamsters, dogs, goats, horses, cows, pigs, or sheep) in which the genes encoding AIF-1 or AIF-2 are deleted or overexpressed using methods known in the art. Such transgenic animals could serve as models of an impaired inflammatory response for research studies aimed at elucidating the pathophysiologic process.

EXAMPLE 7
Characterization of Gal/GalNAc Macrophage Lectin as a Mediator of Transplant Rejection Disclosed herein is the first demonstration of an in vivo role of Gal/GalNAc macrophage lectin in a pathologic state-chronic cardiac rejection. Of particular interest is the unique localization of the expressed gene to the allograft, a degree of compartmentalization not heretofore reported in rejecting organs. By also demonstrating the upregulation of Gal/GalNAc macrophage lectin in association only with inflammatory macrophages elicited with thioglycolate, the data detailed below further substantiate that local activation of inflammatory cells plays a role in the phenomenon of chronic rejection. Taken together, these findings suggest that Gal/GalNAc macrophage lectin, a marker of inflammatory macrophages, is likely to be one of the factors that mediate the recruitment or adhesion of macrophages in chronic cardiac rejection.

Lectins are a family of cell-surface proteins that specifically and selectively bind to complex carbohydrates on apposing cells (Sharon, N. and H. Lis., 1989, Lectins as cell recognition molecules, *Science*, 246:227–234). They have emerged as primary markers for cell recognition with clear functional roles. For example, interference with a lectin's binding to its apposing carbohydrate can disrupt bacterial and mononuclear cell attachment, tumor metastasis, and embryogenesis. Gal/GalNAc macrophage lectin falls into the category of C-type animal lectins characterized by calcium-dependent activity, extracellular location, and absence of free thiols. The murine lectin has been purified in an effort to identify the factor responsible for the tumor binding capacity it conferred to murine macrophages after stimulation with the antitumor streptococcal preparation OK-432 (Oda et al., 1988, supra; Oda et al., 1989, supra). Antibody against the murine lectin prevented macrophage binding to and killing of tumor cells. Kawasaki et al. cloned rat macrophage lectin, which these researchers designated macrophage-asialoglycoprotein-binding protein (m-ASGP-BP), and performed comparisons with the extensively studied rat hepatic lectins (RHL) (Ii et al., supra; Kawasaki, T., M. Ii, Y. Kozutsumi, and I. Yamashina, 1986, Isolation and characterization of a receptor lectin specific for galactose/N-acetylgalactosamine from macrophages, *Carbohydr. Res.*, 151:197–206; Ii, M., T. Kawasaki, and I. Yamashina, 1988, Structural similarity between the macrophage lectin specific for galactose/N-acetylgalactosamine and the hepatic asialoglycoprotein binding protein, *Biochem. Biophys. Res. Commun.*, 155:720–725). Single-chain m-ASGP-BP was shown to form homooligomeric receptors that bind and internalize ligand in a high-affinity fashion specific for Gal and GalNac (Ozaki, K., M. Ii, N. Itoh, and T. Kawasaki, 1992, Expression of a functional asialoglycoprotein receptor through transfection of a cloned cDNA that encodes a macrophage lectin, *J. Biol. Chem.*, 267:9229–9235). Rat hepatic lectin is an endocytic receptor for deglycosylated serum glycoproteins. The major form, RHL1, has a 59% homology with the macrophage lectin cDNA. The 2 minor forms, RHL2 and -3, have 45% homologies. An interesting variation in the macrophage lectin protein is the 24 amino-acid insertion that includes an Arg-Gly-Asp or RGD sequence. RGD is an integrin recognition sequence, raising the possibility that Gal/GalNAc macrophage lectin also confers integrin mediated cellular adhesion.

Mechanisms regulating monocyte/macrophage recruitment are of great interest in understanding pathophysiologic processes (Valente, A. J., M. M. Rozek, E. A. Sprague, and C. J. Schwartz, 1992, Mechanisms in intimal monocyte-macrophage recruitment. A special role for monocyte chemotactic protein-1, *Circulation*, 86:III-20-III-25). A spectrum of cell-surface molecules or receptors is believed to control macrophage function. For example, cytokine receptors, such as the receptor for interferon-γ, modulate the activation of macrophages; integrin receptors, such as CD11a/CD18, regulate integrin adhesion; and the mannose receptor, a macrophage lectin, is involved in endocytosis. Gal/GalNAc macrophage lectin may also fall into this category, given that it is specifically and locally upregulated in the context of a pathophysiologic process where the hallmark is monocyte/macrophage infiltration and arteriosclerosis. More studies are required to identify the functional role of Gal/GalNAc macrophage lectin and to clarify the carbohydrate ligand on apposing cells such as allograft cells. By analogy with other lectins, it is possible that Gal/GalNAc macrophage lectin is also involved in the recognition of macrophages by exposed carbohydrates, and in their localization or adhesion to injured or stimulated donor tissue.

Differentially Expressed Gal/GalNAc Macrophage Lectin

Figure 1A:
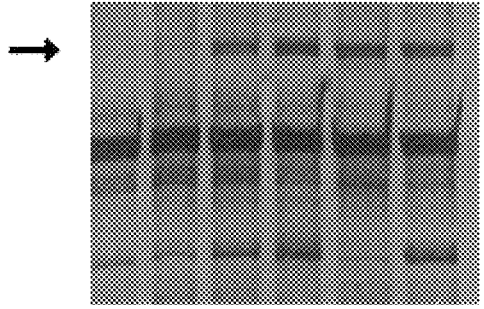
FIG. 1A is a photograph of a differential mRNA display gel showing an upregulated PCR fragment in chronically rejecting hearts produced by allogeneic cardiac transplantation. The 6% polyacrylamide gel electrophoretic analysis of randomly amplified PCR products shows a CDNA fragment identified in the 4 heart samples obtained after allogeneic transplantation (allografts) but not in the 2 hearts obtained after syngeneic transplantation (syngrafts).
Figure 1B:
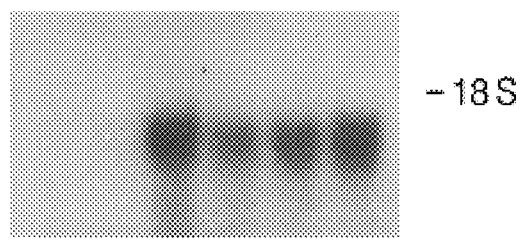
FIG. 1B is a photograph of a Northern blot. The upregulated PCR fragment was harvested and reamplified from the differential display gel shown in FIG. 1A. When radiolabeled with $^{32}P$ and used as a probe in Northern analysis, the fragment hybridized to 1.4-kb transcripts found only in the 4 lanes containing the hearts subjected to allogeneic transplantation, which develop chronic rejection (lanes 3–6), but not to the 2 hearts from syngeneic cardiac transplantation (lanes 1 and 2). Samples from the same total RNA extraction were used in both the PCR and Northern analyses.
Figure 1C:
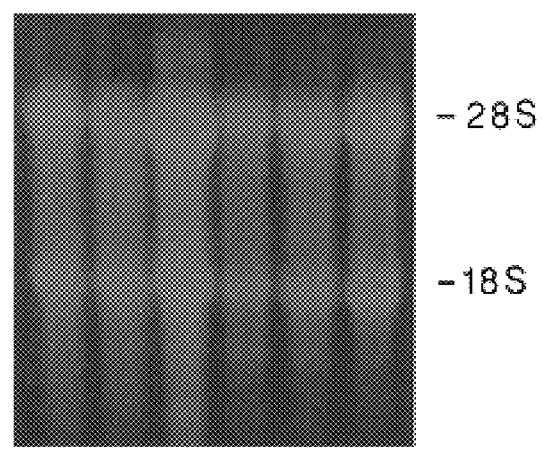
FIG. 1C is a photograph of a RNA gel stained with ethidium bromide before transfer to a fiber membrane, to demonstrate that 20 µg of total RNA was loaded into each lane.

Analysis of polyacrylamide gels containing randomly amplified PCR products obtained by using OPA 4 (AAT CGG GCT G) (SEQ ID NO: 29) as a 5' primer and $T_{12}VTC$ (where V included A, C, and G) as a 3' primer identified an ~380-bp fragment in sample lanes from allogeneic hearts but not in those from syngeneic hearts (FIG. 1A). When the cDNA in these upregulated bands was harvested, reamplified, and used to probe Northern blots, an allograft-specific hybridization pattern was visible (FIG. 1B). Transcripts of 1.4 kb were identified in lanes 3 through 6, containing total RNA derived from 4 hearts after allogeneic transplantation, but not in lanes 1 and 2, containing RNA from 2 syngeneic transplants. RNA loading prior to transfer is shown in the ethidium-stained agarose gel (FIG. 1C). These findings confirmed the gene regulation pattern identified in the differential mRNA display analysis performed with the same panel of total RNAs. Northern analysis was then completed with total RNA obtained from an additional 6 allogeneic transplantations (3 each harvested at 7 and 14 days) and 2 syngeneic transplantations (both harvested at 14 days). FIG. 2 shows a strong hybridization to 1.4-kb transcripts in all 6 lanes (lanes 5–7 and 14–16) containing allografted heart samples, in contrast with the 6 paired host-heart samples and 4 syngeneic-heart samples (2 hosts and 2 syngrafts). Taken together (FIGS. 1 and 2), these findings indicate that the induction was not restricted to individual animals or procedures but occurred uniformly in Lewis to F344 cardiac transplantation.

Cloning of Gal/GalNAc Macrophage Lectin from a Rat Cardiac cDNA Library

Direct cloning of the amplified PCR fragment harvested from the differential display gel produced a 380-bp insert. When this insert was used as a probe in Northern blot analysis, it hybridized to transcripts of 1.4-kb (data not shown) in lanes containing RNA from cardiac allografts but not in lanes containing samples from the host hearts, again reproducing the pattern identified by the differential display analysis. To determine the identity of the full-length cDNA, a cardiac allograft cDNA library (Stratagene, La Jolla, Calif.) was screened with the 380-bp cloned PCR fragment. Nine recombinants were identified, the largest of which was 1.4 kb. Sequence analysis of this fragment and homology searching revealed that the fragment was 99% homologous to rat Gal/GalNAc-macrophage lectin mRNA (GenBank accession number J05495). The J05495 cDNA had been cloned from a rat peritoneal macrophage cDNA library.

Figures 3A, 3B:
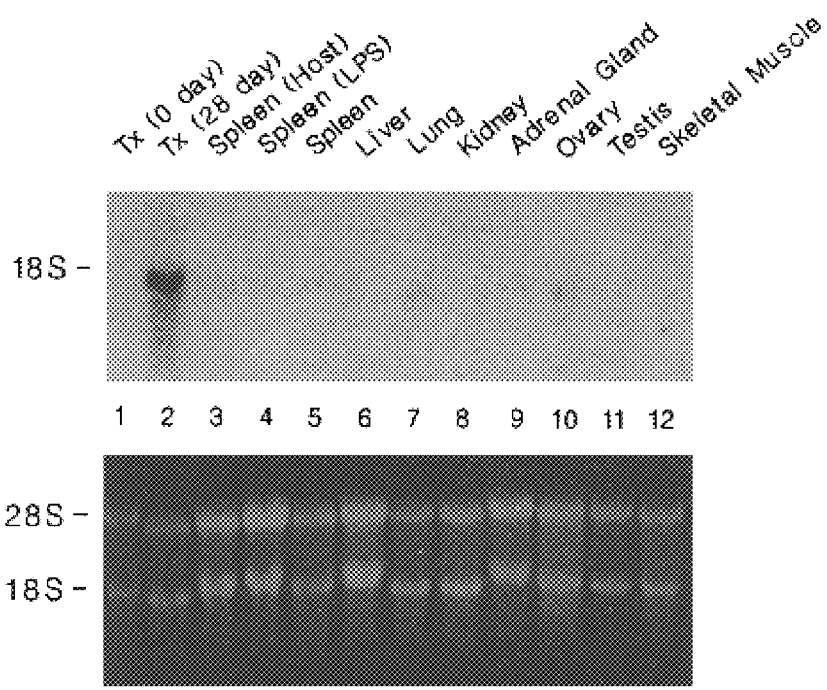
FIG. 3A is a photograph of a Northern blot analysis of RNA from rat organs using the full-length Gal/GalNAc macrophage lectin cDNA as a probe. Tissue-specific upregulation was observed in cardiac allografts. The full-length cDNA was isolated from a rat cardiac allograft cDNA library and used as a probe in Northern blot analysis completed with 20 μg/lane total RNA from the indicated organs. The cDNA probe hybridized strongly to 1.4-kb transcripts in the 28-day cardiac allograft sample. In contrast, hybridization levels were low in all other organs examined, including those rich in resident monocytes and macrophages. To examine possible changes in expression related to systemic effects of inflammatory stimulation, the paired host spleen and a spleen harvested 8 hours following intraperitoneal lipopolysaccharide injection were included.
FIG. 3B is a photograph of a RNA gel stained with ethidium bromide before transfer, to demonstrate that each lane contains 20 μg of total RNA.

Characterization of Gal/GalNAc Macrophage Lectin Gene Expression with a Full-length cDNA Clone Northern blot analysis was used to examine the specificity of Gal/GalNAc macrophage lectin gene expression in a variety of rat organs, particularly those known to contain various resident mononuclear cells. Probing with full-length Gal/GalNAc macrophage lectin cDNA, strong hybridization was observed only in lane 2 containing RNA from the 28-day cardiac allograft (FIG. 3). A sample from the host spleen (lane 3) was included in the assay to determine whether Gal/GalNAc macrophage lectin transcripts were induced by a systemic effect on macrophages after transplantation. The sample from the spleen of a rat 8 hours after intraperitoneal treatment with lipopolysaccharide (lane 4) was included to determine whether this potent inflammatory stimuli would alter Gal/GalNAc macrophage lectin expression in the spleen. A control spleen sample (lane 5) harvested without any stimulation was also included. All 3 samples from spleens showed faint to no hybridization, even though spleens are the principal source of macrophages. Similarly, hybridization signals were not apparent in the lanes containing RNA from other organs including the liver (lane 6), which contains Kupffer cells, lung (lane 7), which contains alveolar macrophages, kidney (lane 8), adrenal gland (lane 9), ovary (lane 10), testes (lane 11) and skeletal muscle (lane 12). This restricted pattern of Gal/GalNAc macrophage lectin expression suggests that its induction is specific to and localized within the cardiac allograft.

Reverse-transcription PCR Measurement of Gal/GalNAc Macrophage Lectin Transcript Levels To achieve greater sensitivity in measuring Gal/GalNAc macrophage lectin transcripts, a reverse transcription-PCR assay was developed using specific primers. PCR conditions were established to insure a linear amplification rate to avoid an amplification plateau in which the PCR product level is no longer proportional to the starting template level. Gal/GalNAc macrophage lectin gene amplification (FIG. 4) was linear over 8 PCR cycles (upper panel) and by more than 2 logs in initial template or cDNA concentration (represented as the calculated amount of cDNA in the PCR reaction) (lower panel). These ranges are consistent with those typically found in PCR assay systems. For subsequent comparisons of Gal/GalNAc macrophage lectin gene transcript levels in various sets of cDNAs, PCR amplification of the control gene, G3PDH, was performed to derive corrected or normalized levels. This approach was used to compare relative differences between samples from three separate cDNA panels.

Specific and Localized Increase in Corrected Gal/GalNAc Macrophage Lectin Levels in Cardiac Allografts FIG. 5 shows that corrected Gal/GalNAc macrophage lectin gene transcript levels increased significantly in cardiac allografts (black bars) at all time points studied (day 7, 14, 28, and 75) in comparison with the 3 reference groups: a day-0 heart (black bar), paired host hearts (hatched bars) and a syngraft (stippled bar) ($P<0.008$). Differences in transcript levels between the various allograft time points were not significant. This lack of a difference suggests that there was no further increase after the initial induction, which would be consistent with an ongoing or chronic stimulation. To examine whether Gal/GalNAc macrophage lectin gene induction was systemically or locally regulated, levels in cardiac allografts were compared with those in host spleens (given that the spleen would be a major source of macrophages but free of direct exposure to stimuli in allografted tissue). As seen in FIG. 6, Gal/GalNAc macrophage lectin levels increased significantly in the 7- and 28-day cardiac allografts (black bars) relative to host spleens and hearts (hatched bars) ($P<0.0001$). The low transcript levels in the host spleens suggest that Gal/GalNAc macrophage lectin gene induction in the cardiac allograft is due to local activation or stimulation.

Corrected Gal/GalNAc Macrophage Lectin Transcript Levels in Isolated Inflammatory Macrophages Transcript levels were measured in various types of isolated rat inflammatory cells to confirm the macrophage-specific nature of Gal/GalNAc gene expression. FIG. 7 shows that corrected transcript levels increased significantly in thioglycolate-elicited macrophages and cells from a 14-day cardiac allograft ($P<0.0001$) compared with adherent (macrophage-enriched) splenocytes (stimulated with buffer, concanavalin A, and lipopolysaccharide/interferon-γ) and nonadherent (lymphocyte-enriched) splenocytes (stimulated with buffer, concanavalin A and lipopolysaccharide/interferon-γ). The identification of Gal/GalNAc macrophage lectin gene transcripts only in thioglycolate-elicited rat macrophages, an inflammatory macrophage population, extends the observation that antibody against the murine lectin binds only to stimulated murine macrophages (Oda, S., M. Sato, S. Toyoshima, and T. Osawa, 1988, Purification and characterization of a lectin-like molecule specific for galactose/N-acetyl-galactosamine from tumoricidal macrophages, *J. Biochem.* (*Tokyo*), 104:600–605).

In situ Localization of Gal/GalNAc Macrophagae Lectin mRNA in Cardiac Allografts In situ hybridization was performed to localize the cell types expressing Gal/GalNAc macrophage lectin transcripts in cardiac allograft tissue. Positive hybridization with the antisense Gal/GalNAC probe was visible in scattered mononuclear cells within inflammatory infiltrates in the interstitium and perivascular space (FIG. 8A and 8B), as demonstrated by the clustering of silver grains (arrows). There was little hybridization to adjacent noninflammatory cells such as cardiac myocytes, or when the negative control, sense Gal/GalNAc probe (FIG. 8C and 8D) was used in seriate sections. There was no significant hybridization of either the antisense or sense probe to paired host hearts, which lacked inflammatory infiltrates (not shown).

Restricted Upregulation of Gal/GalNAc Macrophage Lectin

The gene transcripts of Gal/GalNAc macrophage lectin were found to be specifically localized to and upregulated within Lewis to F344 rat cardiac allografts. Increases in Gal/GalNAc macrophage lectin gene transcript levels occurred early (by 7 days) during initial macrophage accumulation and were sustained (through 14, 28, and 75 days), as would be expected for a chronic inflammatory state characterized by ongoing macrophage infiltration. In contrast, transcript levels were low in 3 reference groups: paired host hearts (exposed to the same circulation but normal on histologic examination), day-14 Lewis syngrafts (subject to the same surgical procedure but with matching host and recipient strains), and day-0 Lewis hearts (harvested but not transplanted). Furthermore, the induction of Gal/GalNAc macrophage lectin gene transcripts occurred in a compartmental fashion restricted to the allografted tissue. Transcript elevation was not found in the matching host spleens (studied because they are the principal source of macrophages but not subject to allogeneic stimulation), nor was it found in other organs rich in resident macrophages. This pattern is in keeping with the arteriosclerotic changes found in cardiac transplants, which affect donor vessels but spare host vessels. Using in situ hybridization, a subset of inflammatory cells (presumably macrophages) within the cardiac allograft was shown to express Gal/GalNAc macrophage lectin transcripts. In examining the specificity of Gal/GalNAc macrophage lectin gene expression in various isolated rat inflammatory cells, transcripts were found to be present only in exudative or thioglycolate-elicited macrophages. Taken together, these results show that Gal/GalNAc macrophage lectin gene expression is restricted in vivo to a subset of infiltrating inflammatory cells in cardiac allografts and in vitro to inflammatory macrophages, suggesting that this lectin is an inducible factor under tight regulatory control.

Gal/GalNAc macrophage lectin is of particular importance in chronic rejection because in vitro studies suggest that its surface expression increases markedly on activated macrophages, and that it regulates the binding to and destruction of tumor cells by macrophages (Oda, S., M. Sato, S. Toyoshima, and T. Osawa, 1989, Binding of activated macrophages to tumor cells through a macrophage lectin and its role in macrophage tumoricidal activity, *J. Biochem.* (Tokyo), 105:1040–1043). These data raise the possibility that Gal/GalNAc macrophage lectin may also play a role in the vascular changes that occur in chronic cardiac rejection by regulating the infiltration of macrophages within the allografts.

Cloning Human Gal/GalNAc Macrophage Lectin

The existence of a human homologue was suggested by Southern analysis using digested human genomic DNA which demonstrated cross hybridization with the rat Gal/GalNAc macrophage lectin cDNA. The human Gal/GalNAc macrophage lectin cDNA can be cloned as follows:

Using primers derived from the rat Gal/GalNAc macrophage lectin DNA sequence, a PCR product would be amplified from human cardiac transplant biopsy tissue. The human PCR product would then be isolated and used as a template for PCR reactions using a different 5' primer based on the rat sequence and the same 3' primer.

DNA fragments derived from the rat Gal/GalNAc macrophage lectin cDNA sequence or PCR fragments amplified from the human template can be used as hybridization probes to screen for overlapping cDNA inserts in a cDNA library prepared from cells previously determined, e.g., by Northern blot, to express transcripts which bind to rat probes. The screening of cDNA libraries with radiolabelled cDNA probes is routine in the art of molecular biology (see Sambrook et al., 1989, *Molecular Cloning: a Laboratory Manual*, second edition., Cold Spring Harbor Press, Cold Spring Harbor, N.Y).

The human cDNA can be isolated and subcloned into a plasmid vector (e.g., pBluescriptII), and the plasmid DNA purified by standard techniques. The cDNA insert can be sequenced using the dideoxy chain termination method well known in the art (Sambrook et al, supra). Oligonucleotide primers corresponding to bordering vector regions as well as primers prepared from previously isolated cDNA clones can be employed to progressively determine the sequence of the entire gene.

DNA containing a sequence that encodes part or all of the amino acid sequence of Gal/GalNAc macrophage lectin can be recloned into an expression vector, using a variety of methods known in the art. For example, a recombinant polypeptide can be expressed as a fusion protein with maltose binding protein produced in *E. coli*. Using the maltose binding protein fusion and purification system (New England Biolabs), the cloned human cDNA sequence can be inserted downstream and in frame of the gene encoding maltose binding protein (malE), and the malE fusion protein can then be overexpressed. In the absence of convenient restriction sites in the human cDNA sequence, PCR can be used to introduce restriction sites compatible with the vector at the 5' and 3' end of the cDNA fragment to facilitate insertion of the cDNA fragment into the vector.

Following expression of the fusion protein, it can be purified by affinity chromatography. For example, the fusion protein can be purified by virtue of the ability of the maltose binding protein portion of the fusion protein to bind to amylose immobilized on a column.

To facilitate protein purification, the pMalE plasmid contains a factor Xa cleavage site upstream of the site into which the cDNA is inserted into the vector. Thus, the fusion protein purified as described above can then be cleaved with factor Xa to separate the maltose binding protein from recombinant human cDNA gene product. The cleavage products can be subjected to further chromatography to purify recombinant macrophage lectin from the maltose binding protein.

The purified recombinant gene product can then be used to raise polyclonal or monoclonal antibodies against the human macrophage lectin using well-known methods (see Coligan et al., eds., *Current Protocols in Immunology*, 1992, Greene Publishing Associates and Wiley-Interscience). To generate monoclonal antibodies, a mouse can be immunized with the recombinant protein, and antibody-secreting B cells isolated and immortalized with a non-secretory myeloma cell fusion partner. Hybridomas are then screened for production of lectin-specific antibody and cloned to obtain a homogenous cell population which produces a monoclonal antibody.

Identification of Compounds which Inhibit Allograft Rejection

A screening method for identifying compounds capable of inhibiting the association of Gal/GalNAc macrophage lectin with its carbohydrate ligand may be carried out as follows:

A cell which expresses Gal/GalNAc macrophage lectin is provided. The cell is most preferably a macrophage, e.g., cell lines, such as J744A.1 (ATCC T1B67) or RAW264.7 (ATCC T1B71) for murine studies, or primary cells such as bone marrowed derived macrophages, but may be any type of cell which expresses Gal/GalNAc macrophage lectin on its surface (e.g., a cell transfected with a cDNA encoding the lectin). Alternatively, Gal/GalNAc lectin may be provided immobilized, e.g., linked to an agarose or acrylamide bead. The lectin is incubated in the presence of a candidate compound. A reference point could be established under standard conditions and the results from any assay compared to the pre-established standard as the control. The lectin is then allowed to bind to labeled carbohydrate ligand, and the resulting complex is washed to remove unbound ligand. The complexes can then be recovered, and subjected to SDS-PAGE. A reduction in the amount of label associated with the complex in the presence of candidate compound compared to that in the absence of candidate compound (or compared to a pre-established standard) indicates that the candidate compound inhibits Gal/GalNAc macrophage lectin-mediated allograft rejection.

An in vitro binding assay may also be accomplished as follows. Modifications of the frozen section assay originally described by Stamper and Woodruff (Stamper, et al., 1977, *J. Immunol.*, 119:772–780, Butcher, et al., 1979, *J. Immunol.*, 123:1996–2003, herein incorporated by reference), can be used to study the role of Gal/GalNAc macrophage lectin in adhesion to rat cardiac allografts. Inflammatory cells demonstrated to express the lectin such as thioglycolate-elicted peritoneal macrophages or T cell-stimulated bone marrow derived macrophages (Gessl, et al., 1989, *J. Immunol.*, 142:4372–4377), herein incorporated by reference) can be labeled with the fluorescent dye 1,1'-dioctadecyl-3,3,3,3'-tetramethylindocarbocyanaine percholate. Labeled macrophages can be incubated with frozen tissue sections from rat cardiac allografts. Conditions can be optimized to maximize specific calcium dependent adhesion to the allograft and control heart sections by variation in temperature, incubation buffer, and washing. Adherent cells can be quantitated using methods known in the art. Specificity of the adherence can be evaluated by measuring the extent of inhibition with a given candidate compound, such as, anti-lectin antibody, Gal-bovine serum albumin (BSA) or GalNAc-BSA conjugates, or recombinantly expressed or modified Gal/GalNAc macrophage lectin polypeptides.

Screening for inhibitors can also be accomplished in vivo. For example, the organ to be allografted can be perfused or soaked in a solution containing a candidate compound prior to transplantation. The organ can then transplanted and monitored for indications of rejection. Transplant rejection can be monitored using conventional methods, e.g., sacrifice of the animal followed by gross examination of the tissue and histological studies, as well as the diagnostic assays of the invention, e.g., evaluating a tissue biopsy for the differential expression of an allograft gene, e.g., Gal/GalNAc macrophage lectin. A decrease in gene expression or a reduction in the physical characteristics of transplant rejection would indicate that the candidate compound inhibits allograft rejection.

Inhibition of Allograft Rejection by Blocking Binding of Gal/GalNAc Macrophage Lectin to Gal/GalNAc The development of inhibitors (peptides, antibodies, or, carbohydrates) that block the lectin-carbohydrate interaction could provide a means of attenuating macrophage infiltration within allografts and disrupting the associated cytokine cascades believed to be initiated by macrophage activation.

Carbohydrates such as Gal or GalNAc, as well as compounds containing Gal or GalNAc, can be used to block binding of Gal/GalNAc macrophage lectin to its ligand on the surface of cells in the allografted tissue, an event that may contribute to the eventual rejection of the allografted tissue or organ.

Soluble polypeptides and fragments thereof, e.g., polypeptide containing a carbohydrate-binding fragment of Gal/GalNAc macrophage lectin, can be used to block the association of macrophage lectin with its carbohydrate ligand.

The term "fragment", as applied to a polypeptide, herein denotes a peptide of at least 10 amino acids. The polypeptide fragments of the invention are preferably at least 20 contiguous amino acids, more preferably at least 40 contiguous amino acids, even more preferably at least 50 contiguous amino acids, and most preferably at least about 80 or more contiguous amino acids in length. Such peptides can be generated by methods known to those skilled in the art, including proteolytic cleavage of the protein, de novo synthesis of the fragment, or genetic engineering, e.g., cloning the gene or a portion of the gene encoding Gal/GalNAc macrophage lectin into an expression vector as described above.

Also within the invention are analogs of the above peptides. Analogs can differ from the peptides encoded by differentially expressed genes, e.g., Gal/GalNAc macrophage lectin or a carbohydrate-binding fragment thereof, by conservative amino acid replacements which alter the sequence but do not adversely affect the functioning of the resulting polypeptide, or by modifications which do not affect the sequence, or by both. Modifications (which do not normally alter primary sequence) include in vivo or in vitro chemical derivitization of polypeptides, e.g., acetylation or carboxylation. Also included are modifications of glycosylation, e.g., those made by modifying the glycosylation patterns of a polypeptide during its synthesis and processing or in further processing steps, e.g., by exposing the polypeptide to enzymes which affect glycosylation, e.g., mammalian glycosylating or deglycosylating enzymes.

The invention includes analogs in which one or more peptide bonds have been replaced with an alternative type of covalent bond (a "peptide mimetic") which is not susceptible to cleavage by peptidases. Where proteolytic degradation of the peptides following injection into the subject is a problem, replacement of a particularly sensitive peptide bond with a noncleavable peptide mimetic will make the resulting peptide more stable and thus more useful as a therapeutic. Such mimetics, and methods of incorporating them into polypeptides, are well known in the art. Similarly, the replacement of an L-amino acid residue with a D-amino acid residue is a standard way of rendering the polypeptide less sensitive to proteolysis. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl.

Peptides may be administered to the patient intravenously in a pharmaceutically acceptable carrier such as physiological saline. Such methods are well known to those of ordinary skill in the art. The formulations of this invention are useful for parenteral administration, such as intravenous, subcutaneous, intramuscular, intraperitoneal, and inhalation.

EXAMPLE 8

Diagnosis and Treatment of Vascular Inflammation and Resulting Atherosclerosis

It has been discovered that AIF-1, and potentially other differentially-expressed allograft genes, are upregulated in atherosclerotic plaques unrelated to the transplant context. Thought to be attributable to the vascular inflammation and injury which are believed to be part of plaque formation, this upregulation of genes originally identified by the allograft/syngraft differential display technique described above provides a means for diagnosing the existence of an atherosclerotic or pre-atherosclerotic condition in an animal. For example, the regions of relatively high level expression of AIF-1, AIF-2, Gal/GalNAc macrophage lectin, ubiquitin, or P1 can be detected by in situ hybridization or immunostaining of a tissue biopsy sample, or by noninvasive imaging techniques using an Indium$^{111}$-labelled antibody or ligand specific for the target molecule.

This discovery also has therapeutic implications. The therapeutic methods described above with respect to preventing allograft rejection are expected to have useful applications in the prevention of atherosclerotic plaques, whether in patients diagnosed by the above techniques, or in those generally considered to be susceptible to formation of such plaques.

Other Embodiments

Hybrid inhibitors of allograft rejection in which a first portion that blocks lectin-carbohydrate binding, e.g., a carbohydrate-binding fragment of Gal/GalNAc macrophage lectin, is linked to a second portion which decreases macrophage-mediated destruction of transplanted tissue, can be constructed using methods known in the art. The first portion can be covalently linked to the second portion, for example, by ligating DNA encoding the first portion in frame with DNA encoding the second portion into an expression vector, and recombinantly producing the hybrid inhibitor. The first portion may be a compound which blocks Gal/GalNAc macrophage lectin binding to Gal/GalNAc, such as a carbohydrate-binding fragment of Gal/GalNAc macrophage lectin, or an antibody or antibody fragment which is lectin-specific or carbohydrate-specific. The first portion of the hybrid may also be an AIF-1 or AIF-2 polypeptide. The second portion of the hybrid can be a compound which is capable of blocking inflammatory cell (e.g., macrophage) infiltration, migration, activation, or other effector functions, such as interleukin-lo, transforming growth factor $\beta$-1, D-mannosidase, or migration inhibition factor.

TABLE 1

Analysis of cDNA fragments identified by differential mRNA display

| | Expression pattern | | | |
|---|---|---|---|---|
| Band | Differential Display | Northern Analysis | Transcript Size | Sequence Homology |
| 1 | allogeneic | allogeneic | 3.5 kb | no homology* |
| | | allogeneic | 1.5 kb | no homology* |
| 2 | allogeneic | allogeneic | 1.4 kb | rat Gal/GalNAc macrophage lectin |
| | | nonspecific | 1.0 kb | not sequenced |
| 3 | allogeneic | nonspecific | 1.8 kb | not sequenced |
| 4 | syngeneic | no hybridization | | |
| 5 | allogeneic | no hybridization | | |
| 6 | allogeneic | no hybridization | | |
| 7 | allogeneic | no hybridization | | |
| 8 | allogeneic | no hybridization | | |
| 9 | syngeneic | nonspecific | 1.0 kb | not sequenced |
| 10 | allogeneic | nonspecific | 1.6 kb | not sequenced |
| 11 | allogeneic | allogeneic | 3.5 kb | mouse P1 protein |
| | | allogeneic | 1.0 kb | mouse ubiquitin-like protein |
| 12 | allogeneic | nonspecific | 5.0 kb | not sequenced |
| | | allogeneic | 0.7 kb | no homology |

*Single cDNA clone hybridized to transcripts of two sizes.

TABLE 2

SEQ ID NO:1

| | | | | |
|---|---|---|---|---|
| GCTGCTGTCA | TTAGAAGGTC | CTCGGTCCCA | CCGTGTTATA | TCCACCTCCA |
| ATTAGGGCAA | TACAGAAATA | GCTTTCTTGG | CTGGGGGACC | AGTTGGCTTC |
| TGGTGTTCTT | TGTTTTTCTC | CTCACACATC | AGAATCATTC | TCAAGATGGC |
| AGATCTCTTG | CCCAGCATCA | TTCTGAGAAA | CTCAGAGTAA | CTGAACGTCT |
| CCTCGGAGCC | ACTGGACACC | TCTCTAATTA | ATTTCTTCAG | CTCTAGATGG |
| GTCTTGGGAA | CCCAAGTTTC | TCCAGCATTC | GCTTCAAGGA | CATAATATCG |
| ATATCTCCAT | TGCCATTCAG | ATCAACTCAT | G | |

TABLE 3

SEQ ID NO:2

| | | | | | | | | | | | | | | | |
|---|---|---|---|---|---|---|---|---|---|---|---|---|---|---|---|
| ACG | AGA | ATA | TGG | CTG | TAA | TCT | GGA | GGA | CAT | CAT | TGT | TGT | TCT | GGG |
| CCC | TTC | AGT | GGG | ATC | TGC | TGC | TTT | ACC | TTC | CAG | AGA | ATC | AGC | AAC |
| CTC | ATT | TAC | CAA | GTT | CAT | CTG | TGT | GTG | AGA | ACG | TTG | ACT | | |

TABLE 4

SEQ ID NO:3

| | | | | |
|---|---|---|---|---|
| TTTTTTTTTT | TTGCAGCCAT | TGTAGAAGGA | TACGGGAAGC | ATTTATCGAA |
| AATTCCAGAC | AAGAACCTCA | TTCTCTAAGG | GATATGAAGC | CTATCTGTGT |
| ACCGAAGTTA | AGGCCATCAC | GGACATGGGA | GAAAAACTTC | TCAGGATGGC |
| AAGATGTGCA | GAGGTCAAGA | TCTTCCTCCT | GGTCTTGAAT | ATCTGTGGAA |
| GAATTCCTCC | TGCTTCTAGA | GATCCTGTGC | TTTTCGGATG | TCAACGTAGG |
| GATTTGGTGA | GTCAAACTGT | CTCACACACG | AAGGATGAAC | ATTGTGAAAT |
| GAGGTTGCTG | ATCTCTGG | | | |

TABLE 5

SEQ ID NO. 4

GAGGAGCCAG CCAACACACT GCAGCCTCAT CGTCATCTCC CCACCTAAGG

CCACCAGCGT CTGAGGAGCT ATGAGCCAGA GCAAGGATTT GCAGGGAGGA

AAAGCTTTTG CACTGCTGAA AGCCCAGCAG GAAGAGAGGT TGGATGGGAT

CAACAAGCAC TTCCTCGATG ATCCCAAGTA CAGCAGTGAT GAGGATCTGC

AGTCCAAACT GGAGGCCTTC AAGACGAAGT ACATGGAGTT TGATCTGAAT

GGCAATGGAG ATATCGATAT TATGTCCTTG AAGCGAATGC TGGAGAAACT

TGGGGTTCCC AAGACCCATC TAGAGCTGAA GAAATTAATT AGAGAGGTGT

CCAGTGGCTC CGAGGAGACG TTCAGTTACT CTGACTTTCT CAGAATGATG

CTGGGCAAGA GATCTGCCAT CTTGAGAATG ATTCTGATGT ATGAGGAGAA

AAACAAAGAA CACCAGAAGC CAACTGGTCC CCCAGCCAAG AAAGCTATTT

CTGAGTTGCC CTAATTGGAG GTGGATATAA CACGGTGGGA CCGAGGACCT

TCTAATGACA GCAGCATGGG AAAAGAAGAA GCAGTTGTGA GCCAGAGTCA

AACTAAATAA ATAATGCTCC CTAGTGCAAA AAAAAAAAA AAAAAAAAA A

TABLE 6

SEQ ID NO. 5

Met Ser Gln Ser Lys Asp Leu Gln Gly Gly Lys Ala Phe Gly Leu

Leu Lys Ala Gln Gln Glu Glu Arg Leu Asp Gly Ile Asn Lys His

Phe Leu Asp Asp Pro Lys Tyr Ser Ser Asp Glu Asp Leu Gln Ser

Lys Leu Glu Ala Phe Lys Thr Lys Tyr Met Glu Phe Asp Leu Asn

Gly Asn Gly Asp Ile Asp Ile Met Ser Leu Lys Arg Met Leu Glu

Lys Leu Gly Val Pro Lys Thr His Leu Glu Leu Lys Lys Leu Ile

Arg Glu Val Ser Ser Gly Ser Glu Glu Thr Phe Ser Tyr Ser Asp

Phe Leu Arg Met Met Leu Gly Lys Arg Ser Ala Ile Leu Arg Met

Ile Leu Met Tyr Glu Glu Lys Asn Lys Glu His Gln Lys Pro Thr

Gly Pro Pro Ala Lys Lys Ala Ile Ser Glu Leu Pro

TABLE 7

SEQ. ID NO. 6

CACATCTTGC CATCCTGA

TABLE 8

SEQ ID NO. 7

CATGGTGCTT GAGAACAG

TABLE 9

SEQ ID NO. 8

GTTTAATGCA GAGAAATTTT ACCGAATAAA GACTGATCAC GCCAGGTAAG
TATGGGTAAT GGGGAAGAAG GAGCCTGAAT CTTACGATGG AATAATTACA
AATCAGAGAG GAATCACAAT CACAGCTCTT GGCGCAGACT GTATACCTAT
AGTCTTTGCA GATCCTGTGA AAAAAGCATG TGGGGCTGCT CACTCGGGCT
GGAAGGGCAC TTTGTTGGGC GTCGCTATGG CTACTGTGAA TGCTATGATA
GCAGAATATG GCTGTAATCT GGAGGACATC ATTGTTGTTC TGGGCCCTTC
AGTGGGATCT

TABLE 10

SEQ ID NO. 9

TTTTTTTTTC TTATATATAA ATTCTAACCT TTAATGTTTA TGTAAACATA
CATGTATATG GCTATGTAAA TCTGTGGGTA TAAGTGTGGA TAGGTGTTGA
AACTAGAAAG GGAACATAAA AGGGGATTGT GCAAGGGAGA ACAAAACACA
TGAGACAGGA AAGAGGGGCT TCTGCAGTGA AAGGGTACAC AAGGGGCCAG
GGAAAGGGAG AGCGAGGGCC AGAAAAACAT GGTGCTTGAG AACAGCATAA
GGAACCTGTA TTTATAAGGC AGTT

TABLE 11

SEQ ID NO. 10

CCGAGTCTCG CGTCTACCAG AGCTGCAAGA TGTCTGTGCT CCCTGGAATA
ATTGTCCTTG TGGGACGATC CTCATGTGCC TGGTGTGCCT GCTTGCTAGT
AGGAGGAATA ATACCGGTTC ATTCTCCTAC CGGAACACCA ATATGTATAT
GTGCATCGGC CCCAAGTCAT CATTGAAAAC ACAGTGTTCT CAAGTGGACA
AGACCTTCAC TGGATTGTTC AAGAGAGATC CAGCCTTACA AGAAGGAAAA
CTAGAGACCA AAATAAATCC TCTTCCTTCT CGATGGGTAT CATCTGCTTC
TTCTTCCTAA AAGACTGGGG GAGCTATCTC TCATAGTGAG TACATTCAGT
GTGCAAGTGG CTCTCAGAGT AGACTCAGTC CTTGCTTG

TABLE 12

SEQ ID NO. 11

TCGAGTTTTT TTTTTTTTTT TTTATATATA AATTCTAACC TTTAATGTTT

ATGTAAACAT ACATGTATAT GGCAATGTAA ATCTGTGGGT ATAAGTGTGG

ATAGGTGTTG AAACTAGAAA GGGAACATAA AAGGGGATTG TGCAAGGGAG

AACAAAACAC ATGACAGGAA AGAGGGGCTT CTGCAGTGAA AGGGTACACA

AGGGGCCAGG GAAAGGGAGA GCGGAGGGCC AGAAAAACAT GGTGCTTGAG

AACAGCATAA GGAAACCTGT ATTTTATAAG GCAGTTAAAA TATACATTTA

AAAGGAACG

TABLE 13

SEQ ID NO. 12

TTTTTTTTTT TTTTTTTTTT TTTTTTTTTT CTTATATATA AATTCTAACC

TTTAATGTTT ATGTAAACAT ACATGTATAT GGCTATGTAA ATCTGTGGGT

ATAAGTGTGG ATAGGTGTTG AAACTAGAAA GGGAACATAA AAGGGGATTG

TGCAAGGGAG AACAAAACAC ATGAGACAGG AAAGAGGGGC TTCTGCAGTG

AAAGGGTACA CAAGGGGCCA GGGAAAGGGA GACGGAGGGC CAGAAAAACA

TGGTGCTTGA GAACAGCATA AGGAAACCTG GTATTTTATA AGGCAGTTAA

AAATATACAT TTAAAAGGAA ACGTTTATCT CCCCTACTGC ATTTGATTCA

AATGAGAAGG TG

TABLE 14

SEQ ID NO. 13

GAAAAAGGTG CCTGACTGAA GAATGGCAGA AGCAGTCTTG ATAGATCTCT

CTGGTTTACA ATTGAACTCT CAGGAAAACT GTCATCAGAT GGTACTGAAG

ACGCTGGATG GTATTCACGA CCACCATGCC CCCAAGGCCA AGTTCCTTTG

TATAATATGT TGCAGCGATG CCACCAATGG AAAGGGTGGG GAATATGGCC

TCTGTGAACT GGAAGCAGGA AATGGCTTTT CAAGTCTCGC GGGAAAATTC

GAGACTGTTA GCCATCCAGC CTGGCTGCCT CTTTGTATTC AGTTAAACAA

AAATAGATGA GGAGGATCTG AGCCGCGTTA AGGTGATTGT GCCCGAG

TABLE 15

SEQ ID NO. 14

TTTTTTTTTT TTTTTTTTTT TTTTTTTTTT TTTTTTTTTT ACATACACAC

AGTATTTTAT TTAGCCATAA TGAAATTATC AAACTTATAG GAAAAATTGA

TGGATCTGGA ATTATTTTAT ATGAGCAAAA TAATCCAGAC TCAGAATAAG

AAACACCACA TGTTCTTTCT TATATATAAA TTCTAACCTT TAATGTTTAT

GTAAACATAC ATGTATATGG CTATGTAAAT CTGTGGGTAT AAGTGTGGAT

AGGTGTTGAA ACTAGAAAGG GAACATAAAA GGGGATTGTG CAAGGGAGAA

CAAAACATAT GAGACAGGAA AGAGGGGCTT CTGTAGTGAA AGGGTACCAA

TABLE 16

SEQ ID NO. 15

TCTCAGCTCA CTCAATCTTT TCAGTAGTTC CAAACGGAGA GATCCCAAAG

TGGTTGTTCA AGAAAACCTC CGCGGCCTGG CAAATGCTGC AGGGTTTAAT

GCAGAGAAAT TTTACCGAAT AAAGACTGAT CACGCCAGGT AAGTATGGGT

AATGGGGAAG AAGGAGCCTG AATCTTACGA TGGAATAATT ACAAATCAGA

GAGGAATCAC AATCACAGCT CTTGGCAGAC TGTATACCTA TAGTCTTTGC

AGATCCTGTG AAAAAAGCAT GTGGGCTGC TCACTCGGGC TGGAAGGGCA

CTTTGTTGGG CGT

TABLE 17

SEQ ID NO. 16

TTTTTTTTTT TTTTTTTTTT TTCTTATATA TAAATTCTAA CCTTTAATGT

TTATGTAAAC ATACATGTAT ATGGCTATGT AAATCTGTGG GTATAAGTGT

GGATAGGTGT TGAAACTAGA AAGGGAACAT AAAAGGGGAT TGTGCAAGGG

AGAACAAAAC ACATGAGACA GGAAAGAGGG GCTTCTGCAG TGAAAGGGTA

CACAAGGGGC CAGGGAAAGG GAGAGCGGAG GGCCAGAAAA ACATGGTGCT

TGAGAATAGC ATAAGGAAAC CTGGTATTTA TAAGGCAGTT AAAAA

TABLE 18

SEQ ID NO. 17

TCGGGCAGGA AGGGCACTTT GTTGGGCGTC GCTATGGCTA CTGTGAATGC

AGTGATAGCA GAATATGGCT GTAGTCTGGA GGACATCGTT GTTGTTCTGG

GCCCTTCAGT GGGATCTTGC TGCTTTACTC TTCCCAGAGA ATCAGCAACC

TCATTTCACA ATGTTCATCC TTCGTGTGTG AGACAGTTTG ACTCACCAAA

TCCCTGCGTT GACATCCGAA AAGCCACCAG GATTCTTCTA GAACGAGGAG

GAATTCTTCC ACAGAATATC AAGACCAGGA GGAAGATCTG ACCTCTGCAC

ATCTGCCATC TGAGAG

TABLE 19

SEQ ID NO. 18

TTTTTTTTTT TTTTTTTATA TAAAATTCT AACCATTTAA TGTTTACGTA

AACATACATG TATATGGCTA TGTAAATCTG TGGGTATAAG TGTGGATAGG

AGTTGAAACT AGAAAGGGAA CATAAAAGGG GATTGTGCAA GGGAGAACAA

AACACATGAG ACAGGAAAGA GGGGCTTCTG CAGTGAAAGG GTACACAAGG

GGCCAGGGAA AGGGAGAGCG GAGGGCCAGA AAACATGGT GCTTGAGAAC

AGCATAAGGA AACCTGGTAT TTTATAAGGC AGTTAAAAAT ATACATTTAA

AAGGAAACGT TTATCTCCCC

TABLE 20

SEQ ID NO. 19

CCGGGGCGCC GGCCGGCCGT GGCGGGAACA CCCGAACTCC GGTGCCCGGA

GGCCCGGACG CTGTGAGGCG GGCGAGCGGG CGGACCCGTT CGGGCGACTC

TGGGGTTCGT TCCCCGAGGC TGCAGCTCAC ACCCCAGCTC GCGGCCGCCG

AGGAGAGCGC GGGAAGCGCC CCGCGTGATT TGGCATAAAA GTCTTTGGGG

GAAAAAGGTG CCTGACTGAA GAATGGCAGA AGCAGTCTTG ATAGATCTCT

CTGGTTTACA ATTGAACTCT CAGGAAAACT GTCATCAGAT GGTACTGAAG

ACGCTGGATG GTATCAC

TABLE 21

SEQ ID NO. 20

TTTTTTTTTT TTTTTTTTTT ACAGTACATA CACACAGCAT TTTATTTAGC

CATAATGAAA TTATCAAACT TATAGGAAAA ATTGATGGAT CTGGAATTAT

TTATTATGAG CAAAATAATC CAGTCTCAGA ATAAGAAACA CCACATGTTC

TTTCTTATAT ATAAATTCTA ACCTTTAATG TTTATGTAAA CATACAGTAT

ATGGCTATGT AAATCAGTGG GTATAAGTGT GGATAGGTGT TGAAACTAGA

AAGGGAACAT AAAAGGGGAT TATCGAAGGG AGAACAAAAC ACATGAGACA

GGAAAGAGGG GCAATAGTAG TGAAAGGGAA TATAAGGGGC CAGGG

TABLE 22

SEQ ID NO. 21

CCTCCGCAGC TGGCAAATGC TGCAGGGTTT AATGCAGAGA AATTTTGCCG

AATAAAGACT GATCACGCCA GGTAAGTATG GGTAATGGGG AAGAAGGAGC

CTGAATCTTA GCATGGAATA ATTACAAATC AGAGAGGAAT CACAATCACA

GCTCTTGGCG CAGACTGTAT ACCTATAGTC TTTGCAGATC CTGTGAAAAA

AGCATGTGGG GCTGCTCACT CGGGCTGGAA GGGCACTTTG TTGGGCGTCG

CTATGGCTAC TGTGAATGCT ATGATAGCAG AATATGGCTG TAATCTGGAG

GACATCATTG TTGTTCTGGG CCCTTCAGT

TABLE 23

SEQ ID NO. 22

TTTTTTTTTT TTTTTTTTTT TACAGTACAT ACACACAGTA TTTTATTTAG

CCATAATGAA ATTATCAAAC TTATAGGAAA ATTGATGGA TCTGGAATTA

TTTATTATGA GCAAAATAAT CCAGACTCAG AATAAGAAAC ACCACATGTT

CTTTACTTAT ATATAAATTC TAACCTTTAA TGTTTATGTA AACATACATG

TATATGGCTA TGTAAATCTG TGGGTATAAG TGTGGATAGG TGTTGAAACT

AGAAAGGGAA CATAAAACGG GGATTATGCA AGGGAGAACA AAACACATGA

GACAGGAAAG AGGGGCTTCT G

TABLE 24

SEQ ID NO. 23

CCTCCGCAGG CTGGCAAATG CTGCAGGGTT TGGTGTAGAG AAATTTTACC

GAATAAAGAC TGATCATGTT AGTGAAGTAT GGGTAATGGG GAAGAAGGAG

CCTGAATCTT ACGATGGAAT AATTACAAAT CAGAGAGGAA TCACAATCAC

AGCTCTTGGC GCAGACTGTA TACCTATAGT CTTTGCAGAT CCTGTGAAAA

AAGCATGTGG GGCTGCTCAC TCGGGCTGGA AGGGCACTTT GTTGGGCGTC

GCTATGGCTA CTGTGAATGC TATGATAGCA

TABLE 25

SEQ ID NO. 24

GCAGATTTGG CATAAAAGTC TTTGGGGGAA AAAGGTGCCT GACTGAAGAA

TGGCAGAAGC AGTCTTGATA GATCTCTCTG GTTTACAATT GAACTCTCAG

GAAAACTGTC ATCAGATGGT ACTGAAGACG CAGGATGGTA TTCACGACCA

CCATGCCCCC AAGGCCAAGT TCCTTTGTAT AATATGTTGC AGCGATGCCA

CCAATGGAAA GGGTGGGGAA TATGGCCTCT GTGAACTGGA AGCAGGAAAT

GGCAAAACAA GTCACGCGGA AAATTCGAGA CTGTTAGCCG T

TABLE 26

SEQ ID NO. 25

TTTTTTTTTT TTTTTTTTAA ACAAGGAAAC AAAACTAGCA CTCATCGCTT

TTTAGACAAT ACATAATTAT TCAAAATTAA CTATTACCGG AAGGCAAGGG

GGCCATACTA ATGGGCCTTG TCTCACATGA GTGCATGTGG GTAGGTGCAG

GACGACTGAC ATTATGCAGA AACGAATTTT AATTTTTAAT CTTTAGTTTG

ATTTAAACAT TGCTTTTAGT ATGATGACAA CACCAGCTGT GCAGAAAGGG

CTCTGGAGAT GCGTTCATAG CAGCACACAC CTGCGGCTCT TCTTCGGTTC

TGGAGGCT

TABLE 27

SEQ ID NO. 26

CTCACACCCC AGCTCGCGGC CGCCGAGGAG AGCGCGGGAA GCGCCCCGCG

TGATTTGGCA TAAAAGTCTT TGGGGAAAA AGGTGCCTGA CTGAAGAATG

GCAGAAGCAG TCTTGATAGA TCTCTCTGGT TTACAATTGA ACTCTCAGGA

AAACTGTCAT CAGATGGTAC TGAAGACGCT GGATGGTATT CACGACCACC

ATGCCCCAA GGCCAAGTTC CTTTGTATAA TATGTTGCAG CGATGCCACC

AATGGAAAGG GTGGGGAATA TGGCCTCTGT GAACTGGAAG CAGGAATGGC

TABLE 28

SEQ ID NO. 27

TTTTTTTTTT TTTTTTTTTT TTTTTTTTTT TTTTTTTACA GTACATACAC

ACAGTATTTT ATTTAGCCAT AATGAAATTA TCAAACTTAT AGGAAAAATT

GATGGATCTG GAATTATTTA TTATGAGCAA AATAATCCAG ACTCAGAATA

AGAAACACCA CATGTTCTTT CTTATATATA AATTCTAACC TTTAATGTTT

ATGTAAACAT ACATGTATAT GGCTGTGTAA ATCTGTGGGT ATAAGTGTGG

ATGGGTGTTG AAACTAGAAA GGGAACATAA AAGGGGGATT GTGCAAGGGA

GAACAAAACA CATGAGACAG GAAAGAGGGG CTTCTGCGGT

---

We claim:

1. An isolated DNA encoding an allograft inflammatory factor-1 (AIF-1) comprising the amino acid sequence of SEQ ID NO:42.

2. The isolated DNA of claim 1, wherein said isolated DNA comprises the coding sequence of SEQ ID NO:43.

3. The isolated DNA of claim 1, wherein the transcription of said DNA is substantially greater in an allograft relative to a syngraft.

4. The isolated DNA of claim 1, wherein said DNA has the sequence of SEQ ID NO:43.

5. An isolated AIF-1 cDNA which hybridizes at high stringency to SEQ ID NO:1, 4, or 43.

6. A substantially pure preparation of a polypeptide comprising the amino acid sequence of human AIF-1 polypeptide (SEQ ID NO: 42).

7. The preparation of claim 6, wherein said polypeptide is human AIF-1 (SEQ ID NO:42).

8. The polypeptide of claim 6, wherein the expression of said polypeptide is substantially greater in an allograft relative to a syngraft.

* * * * *

SEQUENCE LISTING (1) GENERAL INFORMATION:

(iii) NUMBER OF SEQUENCES: 43

(2) INFORMATION FOR SEQ ID NO:1:

(i) SEQUENCE CHARACTERISTICS:
      (A) LENGTH: 331 base pairs
      (B) TYPE: nucleic acid
      (C) STRANDEDNESS: double
      (D) TOPOLOGY: linear (xi) SEQUENCE DESCRIPTION: SEQ ID NO:1:

GCTGCTGTCA TTAGAAGGTC CTCGGTCCCA CCGTGTTATA TCCACCTCCA ATTAGGGCAA   60

TACAGAAATA GCTTTCTTGG CTGGGGACC AGTTGGCTTC TGGTGTTCTT TGTTTTTCTC   120

CTCACACATC AGAATCATTC TCAAGATGGC AGATCTCTTG CCCAGCATCA TTCTGAGAAA   180

GTCAGAGTAA CTGAACGTCT CCTCGGAGCC ACTGGACACC TCTCTAATTA ATTTCTTCAG   240

CTCTAGATGG GTCTTGGGAA CCCAAGTTTC TCCAGCATTC GCTTCAAGGA CATAATATCG   300

ATATCTCCAT TGCCATTCAG ATCAACTCAT G   331

(2) INFORMATION FOR SEQ ID NO:2:

(i) SEQUENCE CHARACTERISTICS:
      (A) LENGTH: 129 base pairs
      (B) TYPE: nucleic acid
      (C) STRANDEDNESS: double
      (D) TOPOLOGY: linear (xi) SEQUENCE DESCRIPTION: SEQ ID NO:2:

ACGAGAATAT GGCTGTAATC TGGAGGACAT CATTGTTGTT CTGGGCCCTT CAGTGGGATC   60

TGCTGCTTTA CCTTCCAGAG AATCAGCAAC CTCATTTACC AAGTTCATCT GTGTGTGAGA   120

ACGTTGACT   129

(2) INFORMATION FOR SEQ ID NO:3:

(i) SEQUENCE CHARACTERISTICS:
      (A) LENGTH: 318 base pairs
      (B) TYPE: nucleic acid
      (C) STRANDEDNESS: double
      (D) TOPOLOGY: linear (xi) SEQUENCE DESCRIPTION: SEQ ID NO:3:

```
TTTTTTTTTT TTGCAGCCAT TGTAGAAGGA TACGGGAAGC ATTTATCGAA AATTCCAGAC      60

AAGAACCTCA TTCTCTAAGG GATATGAAGC CTATCTGTGT ACCGAAGTTA AGGCCATCAC     120

GGACATGGGA GAAAAACTTC TCAGGATGGC AAGATGTGCA GAGGTCAAGA TCTTCCTCCT    180

GGTCTTGAAT ATCTGTGGAA GAATTCCTCC TGCTTCTAGA GATCCTGTGC TTTTCGGATG    240

TCAACGTAGG GATTTGGTGA GTCAAACTGT CTCACACACG AAGGATGAAC ATTGTGAAAT    300

GAGGTTGCTG ATCTCTGG                                                  318
```

(2) INFORMATION FOR SEQ ID NO:4:

(i) SEQUENCE CHARACTERISTICS:
        (A) LENGTH: 627 base pairs
        (B) TYPE: nucleic acid
        (C) STRANDEDNESS: double
        (D) TOPOLOGY: linear (xi) SEQUENCE DESCRIPTION: SEQ ID NO:4:

```
GAGGAGCCAG CCAACACACT GCAGCCTCAT CGTCATCTCC CCACCTAAGG CCACCAGCGT      60

CTGAGGAGCT ATGAGCCAGA GCAAGGATTT GCAGGGAGGA AAAGCTTTTG CACTGCTGAA    120

AGCCCAGCAG GAAGAGAGGT TGGATGGGAT CAACAAGCAC TTCCTCGATG ATCCCAAGTA    180

CAGCAGTGAT GAGGATCTGC AGTCCAAACT GGAGGCCTTC AAGACGAAGT ACATGGAGTT    240

TGATCTGAAT GGCAATGGAG ATATCGATAT TATGTCCTTG AAGCGAATGC TGGAGAAACT    300

TGGGGTTCCC AAGACCCATC TAGAGCTGAA GAAATTAATT AGAGAGGTGT CCAGTGGCTC    360

CGAGGAGACG TTCAGTTACT CTGACTTTCT CAGAATGATG CTGGGCAAGA GATCTGCCAT    420

CTTGAGAATG ATTCTGATGT ATGAGGAGAA AAACAAAGAA CACCAGAAGC AACTGGTCCC    480

CCCAGCCAAG AAAGCTATTT CTGAGTTGCC CTAATTGGAG GTGGATATAA CACGGTGGGA    540

CCGAGGACCT TCTAATGACA GCAGCATGGG AAAAGAAGAA GCAGTTGTGA GCCAGAGTCA    600

AACTAAATAA ATAATGCTCC CTAGTGC                                        627
```

(2) INFORMATION FOR SEQ ID NO:5:

(i) SEQUENCE CHARACTERISTICS:
        (A) LENGTH: 147 amino acids
        (B) TYPE: amino acid
        (D) TOPOLOGY: linear (xi) SEQUENCE DESCRIPTION: SEQ ID NO:5:

```
Met Ser Gln Ser Lys Asp Leu Gln Gly Gly Lys Ala Phe Gly Leu Leu
 1               5                  10                  15

Lys Ala Gln Gln Glu Glu Arg Leu Asp Gly Ile Asn Lys His Phe Leu
                20                  25                  30

Asp Asp Pro Lys Tyr Ser Ser Asp Glu Asp Leu Gln Ser Lys Leu Glu
            35                  40                  45

Ala Phe Lys Thr Lys Tyr Met Glu Phe Asp Leu Asn Gly Asn Gly Asp
        50                  55                  60

Ile Asp Ile Met Ser Leu Lys Arg Met Leu Glu Lys Leu Gly Val Pro
65                  70                  75                  80

Lys Thr His Leu Glu Leu Lys Lys Leu Ile Arg Glu Val Ser Ser Gly
                85                  90                  95

Ser Glu Glu Thr Phe Ser Tyr Ser Asp Phe Leu Arg Met Met Leu Gly
               100                 105                 110

Lys Arg Ser Ala Ile Leu Arg Met Ile Leu Met Tyr Glu Glu Lys Asn
           115                 120                 125
```

```
Lys Glu His Gln Lys Pro Thr Gly Pro Pro Ala Lys Lys Ala Ile Ser
    130                 135                 140

Glu Leu Pro
145

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:6:

CACATCTTGC CATCCTGA                                                      18

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:7:

CATGGTGCTT GAGAACAG                                                      18

(2) INFORMATION FOR SEQ ID NO:8:

(i) SEQUENCE CHARACTERISTICS:
        (A) LENGTH: 310 base pairs
        (B) TYPE: nucleic acid
        (C) STRANDEDNESS: double
        (D) TOPOLOGY: linear (xi) SEQUENCE DESCRIPTION: SEQ ID NO:8:

GTTTAATGCA GAGAAATTTT ACCGAATAAA GACTGATCAC GCCAGGTAAG TATGGGTAAT         60

GGGGAAGAAG GAGCCTGAAT CTTACGATGG AATAATTACA AATCAGAGAG GAATCACAAT        120

CACAGCTCTT GGCGCAGACT GTATACCTAT AGTCTTTGCA GATCCTGTGA AAAAAGCATG        180

TGGGGCTGCT CACTCGGGCT GGAAGGGCAC TTTGTTGGGC GTCGCTATGG CTACTGTGAA        240

TGCTATGATA GCAGAATATG GCTGTAATCT GGAGGACATC ATTGTTGTTC TGGGCCCTTC        300

AGTGGGATCT                                                              310

(2) INFORMATION FOR SEQ ID NO:9:

(i) SEQUENCE CHARACTERISTICS:
        (A) LENGTH: 274 base pairs
        (B) TYPE: nucleic acid
        (C) STRANDEDNESS: double
        (D) TOPOLOGY: linear (xi) SEQUENCE DESCRIPTION: SEQ ID NO:9:

TTTTTTTTTC TTATATATAA ATTCTAACCT TTAATGTTTA TGTAAACATA CATGTATATG         60

GCTATGTAAA TCTGTGGGTA TAAGTGTGGA TAGGTGTTGA AACTAGAAAG GGAACATAAA        120

AGGGGATTGT GCAAGGGAGA ACAAAACACA TGAGACAGGA AGAGGGGCT TCTGCAGTGA        180

AAGGGTACAC AAGGGGCCAG GGAAAGGGAG AGCGAGGGCC AGAAAAACAT GGTGCTTGAG        240

AACAGCATAA GGAACCTGTA TTTATAAGGC AGTT                                   274

(2) INFORMATION FOR SEQ ID NO:10:
```

(i) SEQUENCE CHARACTERISTICS:
    (A) LENGTH: 388 base pairs
    (B) TYPE: nucleic acid
    (C) STRANDEDNESS: double
    (D) TOPOLOGY: linear (xi) SEQUENCE DESCRIPTION: SEQ ID NO:10:

```
CCGAGTCTCG CGTCTACCAG AGCTGCAAGA TGTCTGTGCT CCCTGGAATA ATTGTCCTTG      60

TGGGACGATC CTCATGTGCC TGGTGTGCCT GCTTGCTAGT AGGAGGAATA ATACCGGTTC     120

ATTCTCCTAC CGGAACACCA ATATGTATAT GTGCATCGGC CCCAAGTCAT CATTGAAAAC     180

ACAGTGTTCT CAAGTGGACA AGACCTTCAC TGGATTGTTC AAGAGAGATC CAGCCTTACA     240

AGAAGGAAAA CTAGAGACCA AAATAAATCC TCTTCCTTCT CGATGGGTAT CATCTGCTTC     300

TTCTTCCTAA AAGACTGGGG GAGCTATCTC TCATAGTGAG TACATTCAGT GTGCAAGTGG     360

CTCTCAGAGT AGACTCAGTC CTTGCTTG                                        388
```

(2) INFORMATION FOR SEQ ID NO:11:

(i) SEQUENCE CHARACTERISTICS:
        (A) LENGTH: 309 base pairs
        (B) TYPE: nucleic acid
        (C) STRANDEDNESS: double
        (D) TOPOLOGY: linear (xi) SEQUENCE DESCRIPTION: SEQ ID NO:11:

```
TCGAGTTTTT TTTTTTTTTT TTTATATATA AATTCTAACC TTTAATGTTT ATGTAAACAT      60

ACATGTATAT GGCAATGTAA ATCTGTGGGT ATAAGTGTGG ATAGGTGTTG AAACTAGAAA     120

GGGAACATAA AAGGGGATTG TGCAAGGGAG AACAAAACAC ATGACAGGAA AGAGGGCTT      180

CTGCAGTGAA AGGGTACACA AGGGGCCAGG GAAAGGGAGA GCGGAGGGCC AGAAAAACAT     240

GGTGCTTGAG AACAGCATAA GGAAACCTGT ATTTTATAAG GCAGTTAAAA TATACATTTA     300

AAAGGAACG                                                             309
```

(2) INFORMATION FOR SEQ ID NO:12:

(i) SEQUENCE CHARACTERISTICS:
        (A) LENGTH: 362 base pairs
        (B) TYPE: nucleic acid
        (C) STRANDEDNESS: double
        (D) TOPOLOGY: linear (xi) SEQUENCE DESCRIPTION: SEQ ID NO:12:

```
TTTTTTTTTT TTTTTTTTTT TTTTTTTTTT CTTATATATA AATTCTAACC TTTAATGTTT      60

ATGTAAACAT ACATGTATAT GGCTATGTAA ATCTGTGGGT ATAAGTGTGG ATAGGTGTTG     120

AAACTAGAAA GGGAACATAA AAGGGGATTG TGCAAGGGAG AACAAAACAC ATGAGACAGG     180

AAAGAGGGGC TTCTGCAGTG AAAGGGTACA CAAGGGGCCA GGGAAAGGGA GACGGAGGGC     240

CAGAAAAACA TGGTGCTTGA GAACAGCATA AGGAAACCTG GTATTTTATA AGGCAGTTAA     300

AAATATACAT TTAAAAGGAA ACGTTTATCT CCCCTACTGC ATTTGATTCA AATGAGAAGG     360

TG                                                                    362
```

(2) INFORMATION FOR SEQ ID NO:13:

(i) SEQUENCE CHARACTERISTICS:
        (A) LENGTH: 347 base pairs
        (B) TYPE: nucleic acid
        (C) STRANDEDNESS: double
        (D) TOPOLOGY: linear (xi) SEQUENCE DESCRIPTION: SEQ ID NO:13:

```
GAAAAAGGTG CCTGACTGAA GAATGGCAGA AGCAGTCTTG ATAGATCTCT CTGGTTTACA      60

ATTGAACTCT CAGGAAAACT GTCATCAGAT GGTACTGAAG ACGCTGGATG GTATTCACGA     120

CCACCATGCC CCCAAGGCCA AGTTCCTTTG TATAATATGT TGCAGCGATG CCACCAATGG     180

AAAGGGTGGG AATATGGCC TCTGTGAACT GGAAGCAGGA AATGGCTTTT CAAGTCTCGC      240

GGGAAAATTC GAGACTGTTA GCCATCCAGC CTGGCTGCCT CTTTGTATTC AGTTAAACAA     300

AAATAGATGA GGAGGATCTG AGCCGCGTTA AGGTGATTGT GCCCGAG                   347
```

(2) INFORMATION FOR SEQ ID NO:14:

(i) SEQUENCE CHARACTERISTICS:
        (A) LENGTH: 350 base pairs
        (B) TYPE: nucleic acid
        (C) STRANDEDNESS: double
        (D) TOPOLOGY: linear (xi) SEQUENCE DESCRIPTION: SEQ ID NO:14:

```
TTTTTTTTTT TTTTTTTTTT TTTTTTTTTT TTTTTTTTTT ACATACACAC AGTATTTTAT      60

TTAGCCATAA TGAAATTATC AAACTTATAG GAAAAATTGA TGGATCTGGA ATTATTTTAT     120

ATGAGCAAAA TAATCCAGAC TCAGAATAAG AAACACCACA TGTTCTTTCT TATATATAAA     180

TTCTAACCTT TAATGTTTAT GTAAACATAC ATGTATATGG CTATGTAAAT CTGTGGGTAT     240

AAGTGTGGAT AGGTGTTGAA ACTAGAAAGG GAACATAAAA GGGGATTGTG CAAGGGAGAA     300

CAAAACATAT GAGACAGGAA AGAGGGGCTT CTGTAGTGAA AGGGTACCAA                350
```

(2) INFORMATION FOR SEQ ID NO:15:

(i) SEQUENCE CHARACTERISTICS:
        (A) LENGTH: 313 base pairs
        (B) TYPE: nucleic acid
        (C) STRANDEDNESS: double
        (D) TOPOLOGY: linear (xi) SEQUENCE DESCRIPTION: SEQ ID NO:15:

```
TCTCAGCTCA CTCAATCTTT TCAGTAGTTC CAAACGGAGA GATCCCAAAG TGGTTGTTCA      60

AGAAAACCTC CGCGGCCTGG CAAATGCTGC AGGGTTTAAT GCAGAGAAAT TTTACCGAAT     120

AAAGACTGAT CACGCCAGGT AAGTATGGGT AATGGGAAG AAGGAGCCTG AATCTTACGA      180

TGGAATAATT ACAAATCAGA GAGGAATCAC AATCACAGCT CTTGGCAGAC TGTATACCTA     240

TAGTCTTTGC AGATCCTGTG AAAAAAGCAT GTGGGCTGC TCACTCGGGC TGGAAGGGCA      300

CTTTGTTGGG CGT                                                       313
```

(2) INFORMATION FOR SEQ ID NO:16:

(i) SEQUENCE CHARACTERISTICS:
        (A) LENGTH: 295 base pairs
        (B) TYPE: nucleic acid
        (C) STRANDEDNESS: double
        (D) TOPOLOGY: linear (xi) SEQUENCE DESCRIPTION: SEQ ID NO:16:

```
TTTTTTTTTT TTTTTTTTTT TTCTTATATA TAAATTCTAA CCTTTAATGT TTATGTAAAC      60

ATACATGTAT ATGGCTATGT AAATCTGTGG GTATAAGTGT GGATAGGTGT TGAAACTAGA     120

AAGGGAACAT AAAAGGGGAT TGTGCAAGGG AGAACAAAAC ACATGAGACA GGAAAGAGGG     180

GCTTCTGCAG TGAAAGGGTA CACAAGGGGC CAGGGAAAGG GAGAGCGGAG GGCCAGAAAA     240
```

ACATGGTGCT TGAGAATAGC ATAAGGAAAC CTGGTATTTA TAAGGCAGTT AAAAA        295

(2) INFORMATION FOR SEQ ID NO:17:

(i) SEQUENCE CHARACTERISTICS:
        (A) LENGTH: 316 base pairs
        (B) TYPE: nucleic acid
        (C) STRANDEDNESS: double
        (D) TOPOLOGY: linear (xi) SEQUENCE DESCRIPTION: SEQ ID NO:17:

TCGGGCAGGA AGGGCACTTT GTTGGGCGTC GCTATGGCTA CTGTGAATGC AGTGATAGCA    60

GAATATGGCT GTAGTCTGGA GGACATCGTT GTTGTTCTGG GCCCTTCAGT GGGATCTTGC   120

TGCTTTACTC TTCCCAGAGA ATCAGCAACC TCATTTCACA ATGTTCATCC TTCGTGTGTG   180

AGACAGTTTG ACTCACCAAA TCCCTGCGTT GACATCCGAA AAGCCACCAG GATTCTTCTA   240

GAACGAGGAG GAATTCTTCC ACAGAATATC AAGACCAGGA GGAAGATCTG ACCTCTGCAC   300

ATCTGCCATC TGAGAG                                                  316

(2) INFORMATION FOR SEQ ID NO:18:

(i) SEQUENCE CHARACTERISTICS:
        (A) LENGTH: 320 base pairs
        (B) TYPE: nucleic acid
        (C) STRANDEDNESS: double
        (D) TOPOLOGY: linear (xi) SEQUENCE DESCRIPTION: SEQ ID NO:18:

TTTTTTTTTT TTTTTTATA TATAAATTCT AACCATTTAA TGTTTACGTA AACATACATG     60

TATATGGCTA TGTAAATCTG TGGGTATAAG TGTGGATAGG AGTTGAAACT AGAAAGGGAA   120

CATAAAAGGG GATTGTGCAA GGGAGAACAA AACACATGAG ACAGGAAAGA GGGGCTTCTG   180

CAGTGAAAGG GTACACAAGG GGCCAGGGAA AGGGAGAGCG GAGGGCCAGA AAAACATGGT   240

GCTTGAGAAC AGCATAAGGA AACCTGGTAT TTTATAAGGC AGTTAAAAAT ATACATTTAA   300

AAGGAAACGT TTATCTCCCC                                              320

(2) INFORMATION FOR SEQ ID NO:19:

(i) SEQUENCE CHARACTERISTICS:
        (A) LENGTH: 317 base pairs
        (B) TYPE: nucleic acid
        (C) STRANDEDNESS: double
        (D) TOPOLOGY: linear (xi) SEQUENCE DESCRIPTION: SEQ ID NO:19:

CCGGGGCGCC GGCCGGCCGT GGCGGGAACA CCCGAACTCC GGTGCCCGGA GGCCCGGACG    60

CTGTGAGGCG GGCGAGCGGG CGGACCCGTT CGGGCGACTC TGGGGTTCGT TCCCCGAGGC   120

TGCAGCTCAC ACCCCAGCTC GCGGCCGCCG AGGAGAGCGC GGGAAGCGCC CCGCGTGATT   180

TGGCATAAAA GTCTTTGGGG GAAAAAGGTG CCTGACTGAA GAATGGCAGA AGCAGTCTTG   240

ATAGATCTCT CTGGTTTACA ATTGAACTCT CAGGAAAACT GTCATCAGAT GGTACTGAAG   300

ACGCTGGATG GTATCAC                                                 317

(2) INFORMATION FOR SEQ ID NO:20:

(i) SEQUENCE CHARACTERISTICS:
        (A) LENGTH: 345 base pairs
        (B) TYPE: nucleic acid
        (C) STRANDEDNESS: double
        (D) TOPOLOGY: linear (xi) SEQUENCE DESCRIPTION: SEQ ID NO:20:

TTTTTTTTTT TTTTTTTTTT ACAGTACATA CACACAGCAT TTTATTTAGC CATAATGAAA      60

TTATCAAACT TATAGGAAAA ATTGATGGAT CTGGAATTAT TTATTATGAG CAAAATAATC     120

CAGTCTCAGA ATAAGAAACA CCACATGTTC TTTCTTATAT ATAAATTCTA ACCTTTAATG     180

TTTATGTAAA CATACAGTAT ATGGCTATGT AAATCAGTGG GTATAAGTGT GGATAGGTGT     240

TGAAACTAGA AAGGGAACAT AAAAGGGGAT TATCGAAGGG AGAACAAAAC ACATGAGACA     300

GGAAAGAGGG GCAATAGTAG TGAAAGGGAA TATAAGGGGC CAGGG                    345

(2) INFORMATION FOR SEQ ID NO:21:

(i) SEQUENCE CHARACTERISTICS:
        (A) LENGTH: 329 base pairs
        (B) TYPE: nucleic acid
        (C) STRANDEDNESS: double
        (D) TOPOLOGY: linear (xi) SEQUENCE DESCRIPTION: SEQ ID NO:21:

CCTCCGCAGC TGGCAAATGC TGCAGGGTTT AATGCAGAGA AATTTTGCCG AATAAAGACT      60

GATCACGCCA GGTAAGTATG GGTAATGGGG AAGAAGGAGC CTGAATCTTA GCATGGAATA     120

ATTACAAATC AGAGAGGAAT CACAATCACA GCTCTTGGCG CAGACTGTAT ACCTATAGTC     180

TTTGCAGATC CTGTGAAAAA AGCATGTGGG GCTGCTCACT CGGGCTGGAA GGGCACTTTG     240

TTGGGCGTCG CTATGGCTAC TGTGAATGCT ATGATAGCAG AATATGGCTG TAATCTGGAG     300

GACATCATTG TTGTTCTGGG CCCTTCAGT                                      329

(2) INFORMATION FOR SEQ ID NO:22:

(i) SEQUENCE CHARACTERISTICS:
        (A) LENGTH: 321 base pairs
        (B) TYPE: nucleic acid
        (C) STRANDEDNESS: double
        (D) TOPOLOGY: linear (xi) SEQUENCE DESCRIPTION: SEQ ID NO:22:

TTTTTTTTTT TTTTTTTTTT TACAGTACAT ACACACAGTA TTTTATTTAG CCATAATGAA      60

ATTATCAAAC TTATAGGAAA AATTGATGGA TCTGGAATTA TTTATTATGA GCAAAATAAT     120

CCAGACTCAG AATAAGAAAC ACCACATGTT CTTTACTTAT ATATAAATTC TAACCTTTAA     180

TGTTTATGTA AACATACATG TATATGGCTA TGTAAATCTG TGGGTATAAG TGTGGATAGG     240

TGTTGAAACT AGAAAGGGAA CATAAAACGG GGATTATGCA AGGGAGAACA AAACACATGA     300

GACAGGAAAG AGGGGCTTCT G                                              321

(2) INFORMATION FOR SEQ ID NO:23:

(i) SEQUENCE CHARACTERISTICS:
        (A) LENGTH: 280 base pairs
        (B) TYPE: nucleic acid
        (C) STRANDEDNESS: double
        (D) TOPOLOGY: linear (xi) SEQUENCE DESCRIPTION: SEQ ID NO:23:

CCTCCGCAGG CTGGCAAATG CTGCAGGGTT TGGTGTAGAG AAATTTTACC GAATAAAGAC      60

TGATCATGTT AGTGAAGTAT GGGTAATGGG GAAGAAGGAG CCTGAATCTT ACGATGGAAT     120

AATTACAAAT CAGAGAGGAA TCACAATCAC AGCTCTTGGC GCAGACTGTA TACCTATAGT     180

CTTTGCAGAT CCTGTGAAAA AAGCATGTGG GGCTGCTCAC TCGGGCTGGA AGGGCACTTT     240

GTTGGGCGTC GCTATGGCTA CTGTGAATGC TATGATAGCA                         280

(2) INFORMATION FOR SEQ ID NO:24:

(i) SEQUENCE CHARACTERISTICS:
       (A) LENGTH: 291 base pairs
       (B) TYPE: nucleic acid
       (C) STRANDEDNESS: double
       (D) TOPOLOGY: linear (xi) SEQUENCE DESCRIPTION: SEQ ID NO:24:

GCAGATTTGG CATAAAAGTC TTTGGGGGAA AAAGGTGCCT GACTGAAGAA TGGCAGAAGC    60

AGTCTTGATA GATCTCTCTG GTTTACAATT GAACTCTCAG GAAAACTGTC ATCAGATGGT   120

ACTGAAGACG CAGGATGGTA TTCACGACCA CCATGCCCCC AAGGCCAAGT TCCTTTGTAT   180

AATATGTTGC AGCGATGCCA CCAATGGAAA GGGTGGGGAA TATGGCCTCT GTGAACTGGA   240

AGCAGGAAAT GGCAAAACAA GTCACGCGGA AAATTCGAGA CTGTTAGCCG T            291

(2) INFORMATION FOR SEQ ID NO:25:

(i) SEQUENCE CHARACTERISTICS:
       (A) LENGTH: 308 base pairs
       (B) TYPE: nucleic acid
       (C) STRANDEDNESS: double
       (D) TOPOLOGY: linear (xi) SEQUENCE DESCRIPTION: SEQ ID NO:25:

TTTTTTTTTT TTTTTTTTAA ACAAGGAAAC AAAACTAGCA CTCATCGCTT TTTAGACAAT    60

ACATAATTAT TCAAAATTAA CTATTACCGG AAGGCAAGGG GGCCATACTA ATGGGCCTTG   120

TCTCACATGA GTGCATGTGG GTAGGTGCAG GACGACTGAC ATTATGCAGA AACGAATTTT   180

AATTTTTAAT CTTTAGTTTG ATTTAAACAT TGCTTTTAGT ATGATGACAA CACCAGCTGT   240

GCAGAAAGGG CTCTGGAGAT GCGTTCATAG CAGCACACAC CTGCGGCTCT TCTTCGGTTC   300

TGGAGGCT                                                           308

(2) INFORMATION FOR SEQ ID NO:26:

(i) SEQUENCE CHARACTERISTICS:
       (A) LENGTH: 300 base pairs
       (B) TYPE: nucleic acid
       (C) STRANDEDNESS: double
       (D) TOPOLOGY: linear (xi) SEQUENCE DESCRIPTION: SEQ ID NO:26:

CTCACACCCC AGCTCGCGGC CGCCGAGGAG AGCGCGGGAA GCGCCCCGCG TGATTTGGCA    60

TAAAAGTCTT TGGGGAAAA AGGTGCCTGA CTGAAGAATG GCAGAAGCAG TCTTGATAGA   120

TCTCTCTGGT TTACAATTGA ACTCTCAGGA AAACTGTCAT CAGATGGTAC TGAAGACGCT   180

GGATGGTATT CACGACCACC ATGCCCCCAA GGCCAAGTTC CTTTGTATAA TATGTTGCAG   240

CGATGCCACC AATGGAAAGG GTGGGGAATA TGGCCTCTGT GAACTGGAAG CAGGAATGGC   300

(2) INFORMATION FOR SEQ ID NO:27:

(i) SEQUENCE CHARACTERISTICS:
       (A) LENGTH: 340 base pairs
       (B) TYPE: nucleic acid
       (C) STRANDEDNESS: double
       (D) TOPOLOGY: linear (xi) SEQUENCE DESCRIPTION: SEQ ID NO:27:

TTTTTTTTTT TTTTTTTTTT TTTTTTTTTT TTTTTTTACA GTACATACAC ACAGTATTTT     60

ATTTAGCCAT AATGAAATTA TCAAACTTAT AGGAAAAATT GATGGATCTG GAATTATTTA    120

TTATGAGCAA ATAATCCAG ACTCAGAATA AGAAACACCA CATGTTCTTT CTTATATATA    180

AATTCTAACC TTTAATGTTT ATGTAAACAT ACATGTATAT GGCTGTGTAA ATCTGTGGGT    240

ATAAGTGTGG ATGGGTGTTG AAACTAGAAA GGGAACATAA AAGGGGATT GTGCAAGGGA    300

GAACAAAACA CATGAGACAG GAAAGAGGGG CTTCTGCGGT                          340

(2) INFORMATION FOR SEQ ID NO:28:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:28:

AGCCAGCGAA                                                           10

(2) INFORMATION FOR SEQ ID NO:29:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:29:

AATCGGGCTG                                                           10

(2) INFORMATION FOR SEQ ID NO:30:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:30:

TCTGTGCTGG                                                           10

(2) INFORMATION FOR SEQ ID NO:31:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:31:

CCTAGAAACC CTGAGAAC                                                  18

(2) INFORMATION FOR SEQ ID NO:32:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:32:

GAGTGCCGCT TATTGTAG                                                  18

(2) INFORMATION FOR SEQ ID NO:33:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (xi) SEQUENCE DESCRIPTION: SEQ ID NO:33:

GTCAATTCGC TATGAGCCAG AGCAAG                                              26

(2) INFORMATION FOR SEQ ID NO:34:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (xi) SEQUENCE DESCRIPTION: SEQ ID NO:34:

GAAGAAGCAG TTGTGAGCGT CGACCAA                                             27

(2) INFORMATION FOR SEQ ID NO:35:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:35:

ATCCCAAGTA CAGCAGTGAT GAGG                                                24

(2) INFORMATION FOR SEQ ID NO:36:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:36:

GTCCCCCAGC CAAGAAAGCT ATTT                                                24

(2) INFORMATION FOR SEQ ID NO:37:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (xi) SEQUENCE DESCRIPTION: SEQ ID NO:37:

CTCGCGCTAC TCTCTCTTTC TGG                                                 23

(2) INFORMATION FOR SEQ ID NO:38:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:38:

TTAAGTGGGA TCGAGACATG TAAGC                                               25

(2) INFORMATION FOR SEQ ID NO:39:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:39:

TGAGAAAGTC AGGGTAGCT                                                    19

(2) INFORMATION FOR SEQ ID NO:40:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:40:

ACCTCTACCA GCATCTGC                                                     18

(2) INFORMATION FOR SEQ ID NO:41:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:41:

TGAAGGGAAA AGGGATGATG G                                                 21

(2) INFORMATION FOR SEQ ID NO:42:

(i) SEQUENCE CHARACTERISTICS:
        (A) LENGTH: 147 amino acids
        (B) TYPE: amino acid
        (D) TOPOLOGY: linear (xi) SEQUENCE DESCRIPTION: SEQ ID NO:42:

Met Ser Gln Thr Arg Asp Leu Gln Gly Gly Lys Ala Phe Gly Leu Leu
 1               5                  10                  15

Lys Ala Gln Gln Glu Glu Arg Leu Asp Glu Ile Asn Lys Gln Phe Leu
                20                  25                  30

Asp Asp Pro Lys Tyr Ser Ser Asp Glu Asp Leu Pro Ser Lys Leu Glu
            35                  40                  45

Gly Phe Lys Glu Lys Tyr Met Glu Phe Asp Leu Asn Gly Asn Gly Asp
        50                  55                  60

Ile Asp Ile Met Ser Leu Lys Arg Met Leu Glu Lys Leu Gly Val Pro
65                  70                  75                  80

Lys Thr His Leu Glu Leu Lys Lys Leu Ile Gly Glu Val Ser Ser Gly
                85                  90                  95

Ser Gly Glu Thr Phe Ser Tyr Pro Asp Phe Leu Arg Met Met Leu Gly
               100                 105                 110

Lys Arg Ser Ala Ile Leu Lys Met Ile Leu Met Tyr Glu Glu Lys Ala
           115                 120                 125

Arg Glu Lys Glu Lys Pro Thr Gly Pro Pro Ala Lys Lys Ala Ile Ser
       130                 135                 140

Glu Leu Pro
145

(2) INFORMATION FOR SEQ ID NO:43:

-continued

```
    (i) SEQUENCE CHARACTERISTICS:
        (A) LENGTH: 491 base pairs
        (B) TYPE: nucleic acid
        (C) STRANDEDNESS: double
        (D) TOPOLOGY: linear (xi) SEQUENCE DESCRIPTION: SEQ ID NO:43:

ACCTCTACCA GCATCTGCTG AGCTATGAGC CAAACCAGGG ATTTACAGGG AGGAAAAGCT      60

TTCGGACTGC TGAAGGCCCA GCAGGAAGAG AGGCTGGATG AGATCAACAA GCAATTCCTA     120

GACGATCCCA AATATAGCAG TGATGAGGAT CTGCCCTCCA AACTGGAAGG CTTCAAAGAG     180

AAATACATGG AGTTTGACCT TAATGGAAAT GGCGATATTG ATATCATGTC CCTGAAACGA     240

ATGCTGGAGA AACTTGGAGT CCCCAAGACT CACCTAGAGC TAAAGAAATT AATTGGAGAG     300

GTGTCCAGTG GCTCCGGGGA GACGTTCAGC TACCCTGACT TTCTCAGGAT GATGCTGGGC     360

AAGAGATCTG CCATCCTAAA AATGATCCTG ATGTATGAGG AAAAAGCGAG AGAAAAGGAA     420

AAGCCAACAG GCCCCCCAGC CAAGAAAGCT ATCTCTGAGT TGCCCTGATT TGAAGGGAAA     480

AGGGATGATG G                                                         491
```